(12) United States Patent
Shekhar et al.

(10) Patent No.: US 11,225,689 B2
(45) Date of Patent: Jan. 18, 2022

(54) METHOD FOR DETERMINATION AND IDENTIFICATION OF CELL SIGNATURES AND CELL MARKERS

(71) Applicants: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

(72) Inventors: Karthik Shekhar, Cambridge, MA (US); Sylvain Lapan, Cambridge, MA (US); Irene Whitney, Cambridge, MA (US); Evan Macosko, Cambridge, MA (US); Steven McCarroll, Cambgridge, MA (US); Constance Cepko, Cambridge, MA (US); Aviv Regev, Cambridge, MA (US); Joshua Sanes, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 575 days.

(21) Appl. No.: 15/680,127

(22) Filed: Aug. 17, 2017

(65) Prior Publication Data
US 2018/0127823 A1    May 10, 2018

Related U.S. Application Data

(60) Provisional application No. 62/376,356, filed on Aug. 17, 2016.

(51) Int. Cl.
*G01N 33/48* (2006.01)
*G01N 33/50* (2006.01)
(Continued)

(52) U.S. Cl.
CPC ......... *C12Q 1/6881* (2013.01); *C12N 5/0621* (2013.01); *C12Q 1/6841* (2013.01);
(Continued)

(58) Field of Classification Search
CPC ............ C12Q 1/6841; C12Q 2600/158; C12Q 1/6881; G16B 40/00; C12N 5/0621; G01N 33/56966; G01N 2800/164
See application file for complete search history.

(56) References Cited

U.S. PATENT DOCUMENTS

| 4,816,567 A | 3/1989 | Cabilly et al. |
| 5,270,163 A | 12/1993 | Gold et al. |

(Continued)

FOREIGN PATENT DOCUMENTS

| WO | 96/40281 A2 | 12/1996 |
| WO | 2014/210353 A2 | 12/2014 |

(Continued)

OTHER PUBLICATIONS

Zhu, et al., "Inhibition of Vascular Endothelial Growth Factor-induced Receptor Activation with Anti-Kinase Insert Domain-containing Receptor Single-Chain Antibodies from a Phage Display Library", Cancer Research, vol. 58, No. 15, Aug. 1, 1998, 3209-3214.

(Continued)

*Primary Examiner* — Russell S Negin
(74) *Attorney, Agent, or Firm* — Johnson, Marcou, Isaacs & Nix, LLC; F. Brent Nix, Esq.; Michael B. Scher, Esq.

(57) ABSTRACT

The present invention provides for methods of identifying cell types and cell subtypes from a biological sample or
(Continued)

population of target cells. The methods further provide for determining cell type or cell subtype signatures. The method further provides for bipolar cell subtypes and markers and cell signatures thereof.

12 Claims, 66 Drawing Sheets

(51) Int. Cl.

| | |
|---|---|
| C12Q 1/6881 | (2018.01) |
| C12Q 1/6841 | (2018.01) |
| C12N 5/079 | (2010.01) |
| G01N 33/569 | (2006.01) |
| G16B 40/00 | (2019.01) |
| G16B 25/00 | (2019.01) |
| G16B 25/10 | (2019.01) |
| G16B 40/30 | (2019.01) |
| G16B 40/20 | (2019.01) |

(52) U.S. Cl.
CPC ....... *G01N 33/56966* (2013.01); *G16B 25/00* (2019.02); *G16B 25/10* (2019.02); *G16B 40/00* (2019.02); *G16B 40/20* (2019.02); *G16B 40/30* (2019.02); *C12Q 2600/158* (2013.01); *G01N 2800/164* (2013.01)

(56) References Cited

U.S. PATENT DOCUMENTS

| | | | |
|---|---|---|---|
| 5,811,097 A | 9/1998 | Allison et al. | |
| 2005/0090646 A1* | 4/2005 | Sullivan | A61K 48/0058 530/350 |
| 2005/0233359 A1* | 10/2005 | Masure | C07K 14/475 435/6.16 |
| 2008/0310692 A1* | 12/2008 | Robinson | G06T 7/0012 382/128 |
| 2014/0148350 A1* | 5/2014 | Spetzler | G01N 33/574 506/9 |
| 2014/0206546 A1* | 7/2014 | Chenchik | C12N 15/1072 506/2 |

FOREIGN PATENT DOCUMENTS

| | | | | |
|---|---|---|---|---|
| WO | WO-2015069827 A2 * | 5/2015 | ........... | G06K 9/0014 |
| WO | WO-2015168026 A2 * | 11/2015 | ......... | G06K 9/00147 |
| WO | 2016/040476 A1 | 3/2016 | | |
| WO | 2016/168584 A1 | 10/2016 | | |

OTHER PUBLICATIONS

Koester, et al., "Functional Classes of Cortical Projection Neurons Develop Dendritic Distinctions by Class-Specific Sculpting of an Early Common Pattern", Journal of Neuroscience, vol. 12, No. 4, Apr. 1, 1992, 1382-1393.
Kohler, et al., "Continuous Cultures of Fused Cells Secreting Antibody of Predefined Specificity", Journal of mmunology, vol. 174, 2005, 2453-2455.
Koide, et al., "Monobodies: Antibody Mimics Based on the Scaffold of the Fibronectin Type III Domain", Methods in Molecular Biology, vol. 352, 2007, 95-109.
Kolmar, et al., "Alternative Binding Proteins: Biological Activity And Therapeutic Potential of Cystine-knot Miniproteins", The FEBS Journal, vol. 275, No. 11, Jun. 2008, 2684-2690.
Krishnaswamy, et al., "Sidekick 2 Directs Formation of a Retinal Circuit that Detects Differential Motion", Nature, vol. 524, No. 7566, Aug. 27, 2015, 466-470.
Levine, et al., "Data-Driven Phenotypic Dissection of AML Reveals Progenitor-like Cells that Correlate with Prognosis", Cell, vol. 162, No. 1, Jul. 2, 2015, 184-197.

Liautard, et al., "Specific Inhibition of IL-6 Signalling with Monoclonal Antibodies Against the gp130 Recepto", Cytokine, vol. 9, No. 4, Apr. 1997, 233-241.
Lois, et al., "Germline Transmission and Tissue-Specific Expression of Transgenes Delivered by Lentiviral Vectors", Science, vol. 295, Issue 5556, Feb. 2002, 868-872.
Ma, et al., "Heterogeneous Expression of Voltage-Dependent Na+ and K+ Channels in Mammalian Retinal Bipolar Dells", Visual Neuroscience, vol. 22, Issue 2, Mar. 2005, 119-133.
Macosko, et al., "Highly Parallel Genome-Wide Expression Profiling of Individual Cells Using Nanoliter Droplets", Dell, vol. 161, No. 5, May 21, 2015, 1202-1214.
Marks, et al., "By-passing Immunization: Human Antibodies from V-gene Libraries Displayed on Phage", Journal of Molecular Biology, vol. 222,1991, 581-597.
Masu, et al., "Specific Deficit of the ON Response in Visual Transmission by Targeted Disruption of the mGluR6 Gene", Cell, vol. 80, No. 5, Mar. 10, 1995, 757-765.
Mataruga, et al., "Type 3a and Type 3b OFF One Bipolar Cells Provide for the Alternative Rod Pathway in the Mouse Retina", The Journal of Comparative Neurology, vol. 502, Issue 6, Jun. 20, 2007, 1123-1137.
McDavid, et al., "Data Exploration, Quality Control and Testing in Single-Cell qPCR-based Gene Expression Experiments", Bioinformatics, vol. 29, Issue 4, 2013, 461-467.
Muller, et al., "VEGF and the Fab Fragment of a Humanized Neutralizing Antibody: Crystal Structure of the Complex at 2.4 A Resolution and Mutational Analysis of the Interface", Structure, vol. 6, No. 9, Sep. 15, 1998, 1153-1167.
Vaquero, et al. "Protein Kinase C Localization in the Synaptic Terminal of Rod Bipolar Cells Neuroreport", vol. 7, No. 13, 1996, 2176-2180.
Nygren, "Alternative Binding Proteins: Affibody Binding Proteins Developed From a Small Three-helix Bundle Scaffold", The FEBS Journal, vol. 275, No. 11, Jun. 2008, 2668-2676.
Pang, et al., "Achromatopsia as a Potential Candidate for Gene Therapy", Advances in Experimental Medicine and Biology, vol. 664, 2010, 639-646.
Picelli, et al., "Full-Length RNA-Seq From Single Cells Using Smart-seq2", Nature Protocols,vol. 9, No. 1, 2014, 171-181.
Pitard, et al., "Production and Characterization of Monoclonal Antibodies Against the Leukemia Inhibitory Factor Low Affinity Receptor, gp190", Journal of Immunological Methods, vol. 205, No. 2, Jul. 1, 1997, 177-190.
Pollen, et al., "Low-Coverage Single-Cell mRNA Sequencing Reveals Cellular Heterogeneity and Activated Signaling Pathways in Developing Cerebral Cortex", Nature Biotechnology, vol. 32, Issue 10, Aug. 2014, 1053-1058.
Prat, et al., "Agonistic Monoclonal Antibodies Against the Met Receptor Dissect the Biological Responses to HGF", Journal of Cell Science, vol. 111, Jan. 1998, 237-247.
Puller, et al., "OFF Bipolar Cells Express Distinct Types of Dendritic Glutamate Receptors in the Mouse Retina", Neuroscience, vol. 243, 2013, 136-148.
Puthussery, et al., "Immunohistochemical Identification and Synaptic Inputs to the Diffuse Bipolar Cell Type DB1 in Macaque Retina", The Journal of Comparative Neurology, vol. 519, No. 118, Dec. 15, 2011, 3640-3656.
Roesch, et al., "The Transcriptome of Retinal Muller Glial Cells", The Journal of Comparative Neurology, vol. 509, No. 2, Jul. 10, 2008, 225-238.
Rosenberg, et al., "Scaling Single Cell Transcriptomics Through Split Pool Barcoding", Science, vol. 360, No. 6385, Feb. 2, 2017, 13 pages.
Rosvall, et al., "Maps of Random Walks on Complex Networks Reveal Community Structure", Proceedings of the National Academy of Sciences of the United States of America, vol. 105, No. 4, Jan. 29, 2008, 1118-1123.
Rowan, et al., "Genetic Analysis of the Homeodomain Transcription Factor Chx10 in the Retina Using a Novel Multifunctional BAC Transgenic Mouse Reporter", Developmental Biology, vol. 271, Issue. 2, Jul. 15, 2004, 199-205.

(56) References Cited

OTHER PUBLICATIONS

Sanes, et al., "The Types of Retinal Ganglion Cells: Current Status and Implications for Neuronal Classification", Annual Review of Neuroscience, vol. 38, Mar. 31, 2015, 221-246.
Satija, et al., "Spatial Reconstruction of Single-Cell Gene Expression", Nature Biotechnology, vol. 33, No. 5, May 2015, 495-502.
Schubert, et al., "Development of Presynaptic Inhibition Onto Retinal Bipolar Cell Axon Terminals Is Subclass-Specific", Journal of Neurophysiology, vol. 100, No. 1, Jul. 2008, 304-316.
Shields, et al., "Microfluidic Cell Sorting: A Review of the Advances in the Separation of Cells from Debulking to Rare Cell Isolation", Laboratory on a Chip, vol. 15, No. 5, Mar. 7, 2015, 1230-1249.
Siegert, et al., "Transcriptional Code and Disease Map for Adult Retinal Cell Types", Nature Neuroscience, vol. 15, Issue 3, Jan. 22, 2012, 487-495.
Silverman, et al., "Multivalent Avimer Proteins Evolved by Exon Shuffling of a Family of Human Receptor Domains", Nature Biotechnology, vol. 23, No. 12, Dec. 2005, 1556-1561.
Skerra, "Alternative Binding Proteins: Anticalins Harnessing the Structural Plasticity of the Lipocalin Ligand Pocket to Engineer Novel Binding Activities", The FEBS Journal, vol. 275, No. 11, Jun. 2008, 2677-2683.
Skerra, "Alternative Non-Antibody Scaffolds for Molecular Recognition", Current Opinion in Biotechnology, vol. 18, Issue 4, Aug. 2007, 295-304.
Skerra, "Engineered Protein Scaffolds for Molecular Recognition", Journal of Molecular Recognition, vol. 13, No. 4, Jul. 2000, 167-187.
Star, et al., "Regulation of Retinal Interneuron Subtype Identity by the Iroquois Homeobox Gene Irx6", Development, vol. 139, 2012, 4644-4655.
Stumpp, "Darpins: A New Generation of Protein Therapeutic", Drug Discovery Today, vol. 13, Aug. 2008, 695-701.
Sumbul, et al., "A Genetic and Computational Approach to Structurally Classify Neuronal Types", Nature Communications, vol. 5, No. 3512, Sep. 24, 2014, 26 pages.
Swiech, et al., "In Vivo Interrogation of Gene Function in the Mammalian Brain Using CRISPR-Cas9", Nature Biotechnology, vol. 33, No. 1, Jan. 2015, 102-106.
Tanimoto, et al., "BK Channels Mediate Pathway-Specific Modulation of Visual Signals in the In Vivo Mouse Retina", Journal of Neuroscience, vol. 32, No. 14, Apr. 4, 2012, 4861-4866.
Tasic, et al., "Adult Mouse Cortical Cell Taxonomy Revealed by Single Cell Transcriptomics", Nature Neuroscience, vol. 19, No. 2, Feb. 2016, 335-346.
Trimarchi, et al., "Molecular Heterogeneity of Developing Retinal Ganglion and Amacrine Cells Revealed Through Single Cell Gene Expression Profiling", The Journal of Comparative Neurology, vol. 502, No. 6, Jun. 20, 2007, 1047-1065.
Tuerk, et al., "Systematic Evolution of Ligands by Exponential Enrichment: RNA Ligands to Bacteriophage T4 DNA Polymerase", Science, vol. 249, No. 4968, Aug. 3, 1990, 505-510.
Ueda, et al., "Dystrophin in Rod Spherules; Submembranous Dense Regions Facing Bipolar Cell Processes", Histochemistry and Cell Biology, vol. 108, No. 3, Sep. 1997, 243-248.
Usoskin, et al., "Unbiased Classification of Sensory Neuron Types by Large-Scale Single-cell RNA Sequencing", Nature Neuroscience, vol. 18, No. 1, Jan. 2015, 145-153.
Van Der Maaten, et al., "Visualizing Data Using t-SNE", Journal of Machine Learning Research, vol. 9, 2008, 2579-2605.
Vardi, "Alpha Subunit of Go Localizes in the Dendritic Tips of ON Bipolar Cells", The Journal of Comparative Neurology, vol. 395, 1998, 43-52.
Zilionis, et al., "Single-cell Barcoding and Sequencing Using Droplet Microfluidics", Nature Protocols, vol. 12, No. 1, Jan. 2017, 44-73.
Vercelli, et al., "Emergence of Callosally Projecting Neurons with Stellate Morphology in the Visual Cortex of the Kitten", Experimental Brain Research, vol. 90, Issue 2, Aug. 1992, 346-358.

Wagner, "GO-PCA: An Unsupervised Method to Explore Gene Expression Data Using Prior Knowledge", Pios One, vol. 10, No. 11, 2015, 26 pages.
Wang, et al., "Genetic Screens in Human Cells Using the CRISPR/Cas9 System", Science, vol. 343, No. 6166, Jan. 3, 2014, 80-84.
Wassle, et al., "Cone Contacts, Mosaics, and Territories of Bipolar Cells in the Mouse Retina", Journal of Neuroscience, vol. 29, No. 1, Jan. 7, 2009, 106-117.
Yoon, et al., "Antibodies to Domains II and III of the IL-1 Receptor Accessory Protein Inhibit IL-1 Beta Activity but not Binding: Regulation of IL-1 Responses is via Type I Receptor, Not the Accessory Protein", Journal of Immunology, vol. 160, No. 7, Apr. 1, 1998, 3170-3179.
Young, "Cell Differentiation in the Retina of the Mouse", The Anatomical Record, vol. 212, No. 2, Jun. 1985, 199-205.
Zeisel, et al., "Cell Types in the Mouse Cortex and Hippocampus Revealed by Single-cell RNA-seq", Science, vol. 347, Issue 6226, Mar. 6, 2015, 1138-1142.
Zheng, et al., "Haplotyping Germline and Cancer Genomes with High-Throughput Linked-Read Sequencing", Nature Biotechnology, vol. 34, No. 3, Mar. 2016, 303-311.
Zheng, et al., "Massively Parallel Digital Transcriptional Profiling of Single Cells", Nature Communication, vol. 8, No. 14049, Jan. 16, 2017, 12 pages.
Baas, et al., "The Subcellular Localization of Otx2 is Cell-Type Specific and Developmentally Regulated in the Mouse Retina", Brain Research Reviews, vol. 78, No. (1-2), May 31, 2000, 26-37.
Baden, et al., "The Functional Diversity of Retinal Ganglion Cells in the Mouse", Nature, vol. 529, No. 7586, Jan. 21, 2016, 345-350.
Bartunek, et al., "Avian Stem Cell factor (SCF): Production and Characterization of the Recombinant His-tagged SCF of Chicken and its Neutralizing Antibody", Cytokine, vol. 8, No. 1, Jan. 1996, 14-20.
Binz, et al., "Engineering Novel Binding Proteins from Nonimmunoglobulin Domains", Nature Biotechnology, vol. 23, 2005, 1257-1268.
Blondel, et al., "Fast Unfolding of Communities in Large Networks", Journal of Statistical Mechanics: Theory and Experiment, vol. 2008, Oct. 9, 2008, 12 pages.
Borghuis, et al., "Kainate Receptors Mediate Signaling in Both Transient and Sustained OFF Bipolar Cell Pathways in Mouse Retina", Journal of Neuroscience, vol. 34, No. 18, Apr. 30, 2014, 6128-6139.
Breuninger, et al., "Chromatic Bipolar Cell Pathways in the Mouse Retina", The Journal of Neuroscience, vol. 31, No. 17, Apr. 27, 2011, 6504-6517.
Burmeister, et al., "Ocular Retardation Mouse Caused by Chx10 Homeobox Null Allele: Impaired Retinal Progenitor Proliferation and Bipolar Cell Differentiation", Nature Genetics, vol. 12, No. 4, Apr. 1996, 3766-384.
Cadwell, et al., "Electrophysiological, Transcriptomic and Morphologic Profiling of Single Neurons using Patch-Seq", Nature Biotechnology, vol. 34, No. 2, Feb. 2016, 199-203.
Dai, et al., "New Tools for the Brainbow Toolbox", Nature Methods, vol. 10, No. 6, May 5, 2013, 540-547.
Callaway, et al., "Developmental Sculpting of Dendritic Morphology of Layer 4 Neurons in Visual Cortex: Influence of Retinal Input", Journal of Neuroscience, vol. 31, No. 20, May 18, 2011, 7456-7470.
Cao, et al., "Comprehensive Single Cell Transcriptional Profiling of a Multicellular Organism by Combinatorial Indexing", Science, vol. 357, No. 6352, Aug. 17, 2018, 661-667.
Carlson, et al., "Identification of Amino Acids in the Glutamate Receptor, GluR3, Important for Antibody-binding and Receptor-specific Activation", Journal of Biological Chemistry, vol. 272, No. 17, Apr. 25, 1997, 11295-11301.
Cepko, "Intrinsically Different Retinal Progenitor Cells Produce Specific Types of Progeny", Nature Reviews Neuroscience, vol. 15, No. 9, Sep. 2014, 615-627.
Cheng, et al., "The Iroquois Homeobox Gene, Irx5, is required for Retinal Cone Bipolar Cell Development", Developmental Biology, vol. 287, 2005, 48-60.

(56) References Cited

OTHER PUBLICATIONS

Chow, et al., "Control of Late Off-Center Cone Bipolar Cell Differentiation and Visual Signaling by the Homeobox Gene Vsx1", Proceedings of the National Academy of Sciences, vol. 101, No. 6, Feb. 10, 2004, 1754-1759.
Clackson, et al., "Making Antibody Fragments using Phage Display Libraries", Nature, vol. 352, 1991, 624-628.
Darmanis, et al., "A Survey of Human Brain Transcriptome Diversity at the Single Cell Level", Proceedings of the National Academy of Sciences, vol. 112, No. 23, Jun. 9, 2015, 7285-7290.
Deng, et al., "An Agonist Murine Monoclonal Antibody to the Human c-Mpl Receptor Stimulates Megakaryocytopoiesis", Blood, vol. 92, No. 6, 1998, 1981-1988.
Dobin, et al., "STAR: Ultrafast Universal RNA-Seq Aligner", Nature Neuroscience, vol. 15, No. 12, Dec. 2012, 1621-1623.
Duan, et al., "Identification of Spinal Circuits Transmitting and Gating Mechanical Pain", Cell, vol. 159, No. 6, Dec. 4, 2014, 1417-1432.
Ellington, et al., "In Vitro Selection of RNA Molecules that Bind Specific Ligand", Nature, vol. 346, Aug. 30, 1990, 818-822.
Elshatory, et al., "Expression of the LIM-Homeodomain Protein Isl1 in the Developing and Mature Mouse Retina", The Journal of Comparative Neurology, vol. 503, No. 1, Jul. 1, 2007, 182-197.
Elshatory, et al., "Islet-1 Controls the Differentiation of Retinal Bipolar and Cholinergic Amacrine Cells", The Journal of Neuroscience, vol. 27, No. 46, Nov. 14, 2007, 12707-12720.
Emerson, et al., "Identification of a Retina-Specific Otx2 Enhancer Element Active in Immature Developing Photoreceptors", Developmental Biology, vol. 360, No. 1, Dec. 1, 2011, 241-255.
Euler, et al., "Retinal Bipolar Cells: Elementary Building Blocks of Vision", Nature Reviews Neuroscience, vol. 15, No. 8, Aug. 2014, 507-519.
Feng, et al., "Imaging Neuronal Subsets in Transgenic Mice Expressing Multiple Spectral Variants of GFP", Neuron, vol. 28, No. 1, Oct. 2000, 41-51.
Feng, et al., "Requirement for Bhlhb5 in the Specification of Amacrine and Cone Bipolar Subtypes in Mouse Retina", Development, vol. 133, No. 24, Sep. 28, 2006, 4815-4825.
Fox, et al., "Synaptotagmin I and II are Present in Distinct Subsets of Central Synapses", The Journal of Comparative Neurology, vol. 503, No. 2, Jul. 10, 2007, 280-296.
Fuzik, et al., "Integration of Electrophysiological Recordings with Single-cell RNA-seq Data Identifies Neuronal Subtypes", Nature Biotechnology, vol. 34, No. 2, Feb. 2016, 175-183.
Gebauer, et al., "Engineered Protein Scaffolds as next-Generation Antibody Therapeutics", Current Opinion in Chemical Biology, vol. 13, No. 3, Jun. 2009, 245-255.
Geiss, et al., "Direct Multiplexed Measurement of Gene Expression with Color-coded Probe Pairs", Nature Biotechnology, vol. 26, No. 3, Mar. 2008, 317-325.
Gill, et al., "Biopharmaceutical Drug Discovery Using Novel Protein Scaffolds", Current Opinion in Biotechnology vol. 17, Issue 6, Dec. 2006, 653-658.
Habib, et al., "Div-Seq: Single-Nucleus RNA-Seq Reveals Dynamics of Rare Adult Newborn Neurons", Science, vol. 353, No. 6302, 2016, 925-928.
Harrop, et al., "Antibodies to TR2 (Herpesvirus Entry Mediator), a New Member of the TNF Receptor Superfamily, Block T Cell Proliferation, Expression of Activation Markers, and Production of Cytokines", The Journal of Immunology, vol. 161, No. 4, 1998, 1786-1794.
Hatakeyama, et al., "Roles of Homeobox and bHLH Genes in Specification of a Retinal Cell Type", Development, vol. 128, No. 8, Apr. 2001, 1313-1322.
Haverkamp, et al., "Diversity of Glycine Receptors in the Mouse Retina: Localization of the α3 Subunit", The Journal of Comparative Neurology, vol. 465, No. 4, Oct. 27, 2003, 524-539.
Haverkamp, et al., "Type 4 OFF Cone Bipolar Cells of the Mouse Retina Express Calsenilin and Contact Cones as well as Rods", The Journal of Comparative Neurology, vol. 507, Issue 1, Mar. 1, 2008, 1087-1101.
Head, et al., "Library Construction for Next-Generation Sequencing: Overviews and Challenges", Biotechniques, vol. 56, No. 2, Feb. 1, 2014, 61-77.
Hellmer, et al., "Morphological and Physiological Analysis of Type-5 and other Bipolar Cells in the Mouse Retina", Neuroscience, vol. 315, Feb. 19, 2016, 246-258.
Helmstaedter, et al., "Connectomic Reconstruction of the Inner Plexiform Layer in the Mouse Retina", Nature, vol. 500, No. 7461, Aug. 8, 2013, 168-174.
Horwell, "The 'Peptoid' Approach to the Design of Non-Peptide, Small Molecule Agonists and Antagonists of Neuropeptides", Trends in Biotechnology, vol. 13, No. 4, Apr. 1, 1995, 132-134.
Ichinose, et al., "Differential Signalling and Glutamate Receptor Compositions in the OFF Bipolar Cell Types in the Mouse Retina", The Journal of Physiology, vol. 594, No. 4, 2016, 883-894.
Ichinose, et al., "Roles of ON Cone Bipolar Cell Subtypes in Temporal Coding in the Mouse Retina", Journal of Neuroscience, vol. 34, No. 26, Jun. 25, 2014, 8761-8771.
Jeon, et al., "The Major Cell Populations of the Mouse Retina", The Journal of Neuroscience, vol. 18, No. 21, Nov. 1, 1998, 8936-8946.
Jin, et al., "Early B-Cell Factors are Required for Specifying Multiple Retinal Cell Types and Subtypes from Postmitotic Precursors", The Journal of Neuroscience, vol. 30, No. 36, Septembers, 2010, 11902-11916.
Kay, et al., "Retinal Ganglion Cells with Distinct Directional Preferences Differ in Molecular Identity, Structure, and Central Projections", Journal of Neuroscience, vol. 31, No. 21, May 25, 2011, 7753-7762.
Kim, et al., "Identification of Molecular Markers of Bipolar Cells in the Murine Retina", The Journal of Comparative Neurology, vol. 507, No. 5, Apr. 10, 2008, 1795-1810.
Kim, et al., "Laminar Restriction of Retinal Ganglion Cell Dendrites and Axons: Subtype-Specific Developmental Patterns Revealed with Transgenic Markers", Journal of Neuroscience, vol. 30, No. 4, Jan. 27, 2010, 1452-1462.
Klein, et al., "Droplet Barcoding for Single-Cell Transcriptomics Applied to Embryonic Stem Cells", Cell, vol. 161, No. 5, May 21, 2015, 1187-1201.

\* cited by examiner

K

A

F

G

M

METHOD FOR DETERMINATION AND IDENTIFICATION OF CELL SIGNATURES AND CELL MARKERS

CROSS-REFERENCE TO RELATED APPLICATIONS

This application claims the benefit of U.S. Provisional Application No. 62/376,356, filed Aug. 17, 2016. The entire contents of the above-identified priority application is hereby fully incorporated herein by reference.

STATEMENT REGARDING FEDERALLY SPONSORED RESEARCH

This invention was made with government support under grant number MH105960 granted by the National Institutes of Health. The government has certain rights in the invention.

TECHNICAL FIELD

The subject matter disclosed herein is generally directed to methods for determination and identification of cell signatures and cell perturbations.

BACKGROUND

Investigations into tissue or organ development, function, and disease increasingly depend upon accurate identification and categorization of different cell types. For example investigations into brain, tissue, organ development, function, and disease depend upon identification and categorization of cell types. Assignment of roles, genes, or pathologies to specific types allows fundamental processes to be understood with greater precision than when they are assigned to organ or tissue regions, e.g., brain regions, or broad classes of cells. Moreover, molecular identifiers of specific types enable comparison of results obtained at different times, in different laboratories, or following experimental perturbations. In model organisms, they also enable genetic access, allowing cells, e.g., neurons to be marked and manipulated. Accordingly, numerous methods have been developed to attribute discrete and reproducible features to individual cell types for example neuronal types (Seung and Sumbul, 2014).

Despite methodological advances, the enterprise of cell type categorization remains challenging for both technical and conceptual reasons. Conceptually, the very definition of a "cell type" is contentious. A cell type is a classification used to distinguish between morphologically or phenotypically distinct cell forms within a species. A multicellular organism may contain a number of widely differing and specialized cell types, such as muscle cells and skin cells in humans, that differ both in appearance and function yet are genetically identical. Cells are able to be of the same genotype, but different cell type due to the differential regulation of the genes they contain. Classification of a specific cell type is often done through the use of microscopy and (such as those from the cluster of differentiation family that are commonly used for this purpose in immunology). Existing taxonomies for example represent cells such as neurons as a hierarchy of types whose distinctions reflect one or more criteria, including morphology, physiology, expression of specific molecules, and connectivity to synaptic partners (Sanes and Masland, 2015). While distinctions at the upper levels of this hierarchy are easily agreed upon (e.g. sensory neurons vs. motor neurons), divisions at the lower levels are less obvious, as the putative types share multiple features (e.g. multiple types of direction-selective retinal ganglion cells). Furthermore, it remains unclear whether different ways of defining cell types—for example distinctions based on morphological, molecular, or physiological properties—would in fact agree with each other. It is also possible that some critical distinctions will be graded rather than categorical. As a result, there are few, if any, cases in which a diverse vertebrate neuronal class has been comprehensively and definitively partitioned into types.

A taxonomy based on molecular features of cells is an attractive solution to these challenges. Single-cell RNA sequencing (scRNA-seq) presents the opportunity to categorize individual cells, then to group these into types based on gene expression signatures in a quantitative and unbiased fashion. Several recent studies have combined this method with computational analysis to identify transcriptionally distinct neuronal types (Darmanis et al., 2015; Macosko et al., 2015; Pollen et al., 2014; Tasic et al., 2016; Usoskin et al., 2015; Zeisel et al., 2015). However, few if any of these studies have been able to conclusively determine whether each of the predicted groups represents a distinct type, and whether the proposed classifications encompass all cell types in the population of interest. Among the many obstacles, two stand out. First, it is likely that the number of cells profiled to date, typically ranging from a hundred to a few thousand, is short of the number needed for complete categorization of resident cell types. Even in the mouse retina for example, from which 45,000 cells were analyzed from whole tissue (Macosko et al., 2015), retinal ganglion cells were represented by fewer than 450 cells (~1%, as expected from microscopy), which was insufficient for the computational methods used to dissect (in an unsupervised manner) this diverse neuronal class, which includes at least 30 types (Baden et al., 2016; Sanes and Masland, 2015). Second, optimizing molecular and computational methods to ensure that populations are neither under-sampled nor over-clustered requires a highly scalable method for in vivo validation against an orthogonal criterion of cell type.

To address these challenges a comprehensive, validated classification scheme for a diverse class of cells for example for a diverse class of interneurons, e.g., the bipolar cells (BCs) of the mouse retina was generated. BCs have been studied intensively by morphological, and physiological methods in many species, including mouse (Euler et al., 2014; Helmstaedter et al., 2013; Wassle et al., 2009). They receive synaptic input from rod and cone photoreceptors, process it in diverse ways, and transmit it to retinal ganglion cells (RGCs), which in turn send axons through the optic nerve to the rest of the brain. BCs are divided into rod and cone types, based on the photoreceptor type from which they receive their predominant synaptic input. They are also divisible into ON and OFF types based on whether they are excited (depolarized) by increases or decreases in illumination level. There is only a single known rod bipolar cell (RBC) type, but cone BCs have been divided into 9-12 types. These types were first defined by morphological features, which were later related to physiological properties and, in some cases, to endogenous or transgenic molecular markers (Euler et al., 2014; Helmstaedter et al., 2013; Wassle et al., 2009). This prior knowledge is useful for evaluating computational methods, and provides a set of benchmarks for validating novel markers and potentially novel types.

SUMMARY

In some aspects the disclosure refers to a method of identifying a cell or cell marker, comprising; a) isolating target cells based on a marker specifically expressed in the cell or by label-free imaging flow cytometry; b) quantifying gene expression in the target cells by sequencing, and c) clustering the target cells based on the gene expression by application of one or more algorithms, d) optionally determining a transcription signature for each cluster based at least in part on identifying differentially expressed genes between two or more clusters and between each cluster and the remaining cells as background, and e) optionally validating gene expression against cellular morphology. In certain example embodiments, the sequencing is single-cell sequencing. In certain embodiments, the single cell sequencing may comprise sequencing 5,000 or more single cells. In certain embodiments, the single cell sequencing depth may be about 10,000 or less reads per cell. In certain embodiments, the marker may be a fluorescent transgene specifically expressed by the target cells. Not being bound by a theory, a marker can be expressed from a cell type specific regulatory sequence (e.g., promoter).

In other aspects the disclosure is directed to a method of determining transcription signatures for cell types or cell sub-types, comprising identifying cell types and/or cell sub-types by applying one or more clustering algorithms to a set of sequenced transcript reads from a population of cells, wherein each resulting cluster of sequenced transcript reads identifies a particular cell type or cell sub-type; and determining a transcription signature for each identified cell type or cell sub-type based at least in part on identifying differentially expressed transcripts between the identified cell type or cell sub-type.

In further aspects the disclosure relates to a method of identifying retinal cell types or retinal cell sub-types present in biological samples, comprising detecting one or more retinal cell transcription signatures in a sample comprising a cell population comprising retinal cells using single cell sequencing, wherein each transcription signature identifies a particular retinal cell type or retinal cell sub-type.

In other aspects the disclosure refers to a method for cell perturbation screening, comprising exposing a test cell population to one or more perturbations; detecting one or more cell transcription signatures in a sample by single cell sequencing of transcripts expressed in the cell population, wherein the one or more transcription signatures indicates an absence or presence of a particular cell type or cell sub-type in the sample.

In some examples of these aspects the one or more perturbation(s) comprise(s) exposing the sample to one or more chemical agents, a concentration range of one or more chemical agents, or both.

In other examples of these aspects the absence or presence of a particular cell type or cell sub-type indicates a propensity of the one or more perturbations to cause blindness.

In further aspects the disclosure is directed to a bipolar cell for example a bipolar cell BC1A characterized by expression of Pcdh17 and Fezf2; or to a bipolar cell BC1B characterized by expression of Pcdh10 and Fezf1; or to a bipolar cell BC5A characterized by expression of Sox6, B046251, Cntn5, Lrrtm1, Nnat, Htr3a, Kcng4, and Nfia; or to a bipolar cell BC5B characterized by expression of Pcdh17, Nfia, Cntn5, Gfra3, Chrm2, and Nnat; or to a bipolar cell BC5C characterized by expression of Pcdh17, Pcdh10, Cntn5, Slitrk5 and Areg; or to a bipolar cell BC5D characterized by expression of Nnat, B046251, Kirrel3, Htr3a and Kcng4, Lact1, Lrrtm1 and Nfia; or to a bipolar cell BC8 characterized by Serpini$^+$ Cpne$^-$; or to a bipolar cell BC9 characterized by Serpini$^+$ Cpne$^+$ and optionally an exclusion zone of 14.3 μm where no other Cpne$^+$ cells are positioned.

In further aspects the disclosure is directed to a method of identifying cell types or cell sub-types present in a biological sample, comprising: RNA sequencing 20,000 or more single cells from the biological sample, wherein the sequencing depth is about 10,000 or less reads per cell; and identifying cell types and/or cell sub-types by applying one or more clustering algorithms to the set of sequenced transcript reads from the single cells, wherein each resulting cluster of sequenced transcript reads identifies a particular cell type or cell sub-type. The method may further comprise determining a transcription signature for each identified cell type or cell sub-type based at least in part on identifying differentially expressed transcripts between the identified cell type or cell sub-type.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 1 is a sketch of retinal cross-section depicting major resident cell classes. Rod and cone photoreceptors detect and transduce light stimuli into chemical signals, relaying this information to rod and cone bipolar cells (BCs), respectively (turquoise and purple/orange). BCs synapse on retinal ganglion cells (whose axons form the optic nerve) in the inner plexiform layer (IPL) at varying depths that depend on the BC type.

FIG. 2 is an overview of experimental strategy. Retinas from Vsx2-GFP mice were dissociated, followed by FAC sorting for GFP+ cells. Single cell libraries were prepared using Drop-seq and sequenced. Raw reads were processed to obtain a digital expression matrix (genes×cells). PCA, followed by graph clustering was used to partition cells into clusters, and identify cluster-specific markers, which were validated in vivo using methods that detect gene expression and cellular morphology in combination.

FIG. 3, FIG. 4, and FIG. 5 are 2D visualizations of single cell clusters using the tSNE algorithm. Individual points correspond to single cells colored according to clusters identified by the Louvain-Jaccard algorithm (FIG. 3), the Infomap algorithm (FIG. 4), and numbered in decreasing order of size. Arrow indicates a BC cluster that was partitioned by Infomap (examined later in Panels A through F of FIG. 13). FIG. 5 shows the clustering output of Infomap when applied on cells from a single Drop-seq experiment (50% of the dataset). The tSNE representation was only used for visualization, and not for the identification of clusters.

FIG. 6 shows gene expression patterns (columns) of major retinal class markers (left panels) and known BC type markers (right panels) in BC (upper panels) and non-BC clusters (lower panels) based on the Louvain-Jaccard clusters in panel FIG. 3. Clusters with cell-doublet signatures, and that contained <50 cells are not shown. Putative cell type assignments, based on the expression of known genes, are indicated on the right. Nomenclature for BC types 1 and 5 is based on results in Panels A through G of FIG. 11 and Panels A through M of FIG. 12. The size of each circle depicts the percentage of cells in the cluster in which the marker was detected (≥1 transcript or UMI), and its color depicts the average transcript count in expressing cells (nTrans). MG=Müller glia, AC=amacrine cells, Rod PR=rod photoreceptors, and Cone PR=cone photoreceptors.

FIG. 7 is a hierarchical clustering of BC clusters based on average expression levels of genes within each cluster (euclidean distance metric, average linkage). The confidence level of each split was computed using bootstrap. Relatedness between clusters was used in prospective cluster assignment to BC type in the panel of FIG. 6.

FIG. 8 shows representative markers (columns) enriched in BC clusters (rows) predicted and validated in this study. Representation as shown in FIG. 6.

FIG. 9 shows validation of RBC-specific genes Vstm2b, Casp7, and Rpa1 by FISH combined with PKCα immunostaining, which marks RBCs.

FIG. 10 shows validation of new markers of BC3A, BC3B, BC4, BC6, and BC7 against cell morphology. Leftmost panels show representative drawings of these types based on EM reconstructions (Helmstaedter et al., 2013), middle panels show lentiviral labeling of single BCs combined with FISH for the indicated gene in retinal cross sections. Dashed lines are drawn from calretinin antibody labeling within sublaminae (S) 2, 3, and 4. Insets show localization of FISH signal within virus-labeled cell bodies. Rightmost panels show FISH stains on retinal whole mounts, showing labeling of cell bodies across a broad area of retina. To reduce background puncta in the GFP+ lentivirus labeled cells, an outlier removal noise filter was applied. Scale bars indicate 20 µm for main panels and 10 µm for insets.

DETAILED DESCRIPTION OF THE EXAMPLE EMBODIMENTS

General Definitions

Figure 1:
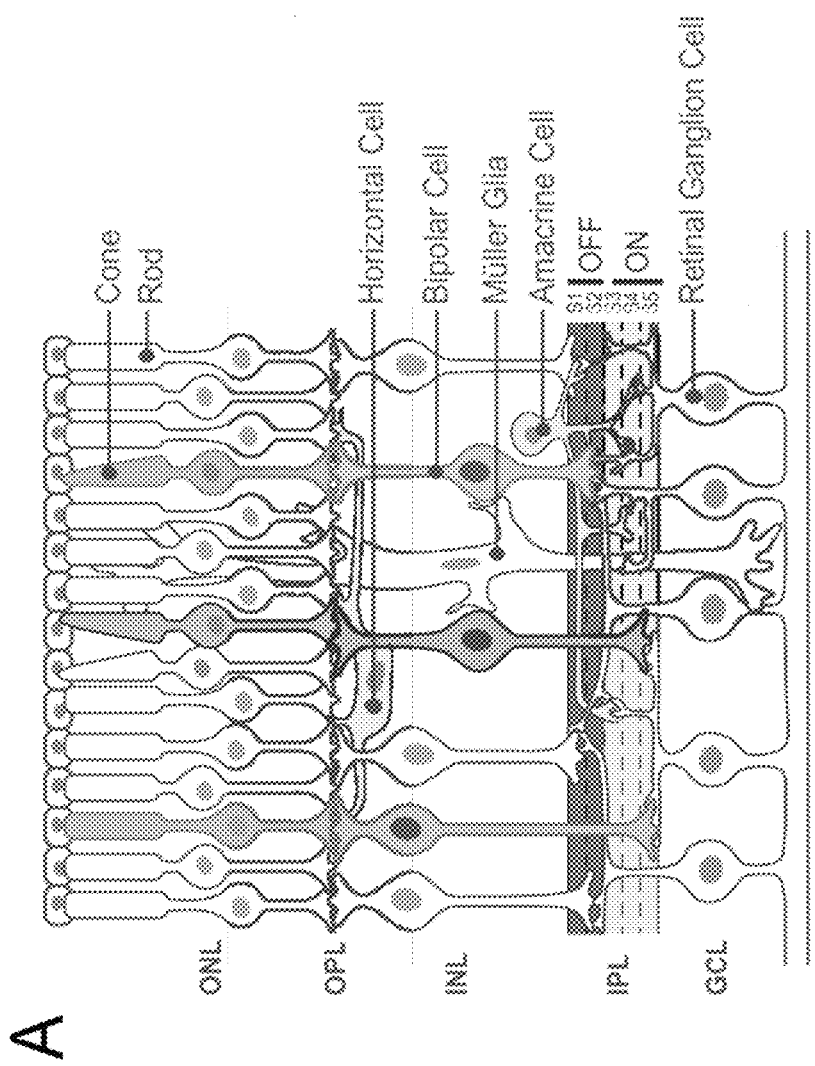
FIGS. 1-7 show the clustering of bipolar cells by Drop-seq.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited in this application are indicative of the level of skill in the art(s) to which the application pertains.

All publications, published patent documents, and patent applications cited herein are hereby incorporated by reference to the same extent as though each individual publication, published patent document, or patent application was specifically and individually indicated as being incorporated by reference.

In the following explanations and definitions, respectively, of relevant terms of the present disclosure are provided:

Cell type is a classification used to distinguish between morphologically and/or phenotypically distinct cell forms within a species. A multicellular organism may contain a number of widely differing and specialized cell types, such as muscle cells and skin cells in humans, that differ both in appearance and function yet are genetically identical. Cells are able to be of the same genotype, but different cell type due to the differential regulation of the genes they contain.

Cell sub-type belongs to the same cell type but differs in physiological and/or morphological characteristics and belongs to a secondary or subordinate type.

Cell marker is a biochemical and/or genetic characteristic which allows to distinguish between different types of cells, tissues, or organs, and/or different states of cells, tissues or organs.

Fluorescence in situ hybridization (FISH) is a cytogenetic technique that uses fluorescent probes that bind to only those parts of the chromosome with a high degree of sequence complementarity.

Morphology refers to the form and structure of a human being, an animal or plant or any of its parts.

Physiology refers to function and activity of a human being, an animal or plant and any of its parts (cell, tissue, organ) including physical and chemical processes.

Label-free imaging flow cytometry combines high-throughput capabilities of conventional flow cytometry with single-cell imaging. Unlabeled cells are scored for particular phenotypes by applying supervised or unsupervised machine learning to morphological features extracted from brightfield and the typically-ignored darkfield images of cells from an imaging cytometer.

Sample is an ex vivo or in vitro sample comprising biological material such as a cell, tissue or organ.

The present disclosure refers to each of these methods alone, or in combination with each other or in combination with any other computational method.

Overview

Patterns of gene expression can be used to characterize and classify cell types for example neuronal types. It is challenging, however, to generate taxonomies that fulfill the essential criteria of being comprehensive, harmonizing with conventional classification schemes, and lacking superfluous subdivisions of genuine types. To address these challenges, massively parallel single-cell transcriptomic profiling and optimized computational methods on a heterogeneous class of cells for example neurons such as mouse retinal bipolar cells (BCs) were used for the present disclosure. In an example derived from a population of about 25,000 BCs a molecular classification that identified 15 types of BCs including all 13 types observed previously, and two novel types, one of which has a noncanonical morphology and position. The classification scheme was validated in the present disclosure and dozens of novel markers using methods that match molecular expression to cell morphology were identified. This work provides a systematic methodology for achieving comprehensive molecular classification of cells for example neurons, identifies novel cell types, and uncovers transcriptional differences that distinguish types within a class.

To comprehensively profile cells for example BCs in a cost-effective manner Drop-seq, a recently developed high-throughput scRNA-seq method is used, which utilizes droplet microfluidics together with massive molecular barcoding of droplets (Macosko et al., 2015). Drop-seq enables profiling of over 10,000 cells in a single experiment at a low cost per cell. Thousands of cells such as 10,000 to 100,000 cells, for example from a transgenic animal line, that marks the specific cell type of interest are profiled and a high-quality subset of cells is selected for detailed analysis. In an example of the present disclosure about 45,000 cells from a transgenic mouse line that marks BCs were profiled and a high-quality subset of about 28,000 cells was selected for detailed analysis. This is some 10-30 fold more cells than the number of cells analyzed in recent studies of cortical, hippocampal or sensory neurons (Tasic et al., 2016; Usoskin et al., 2015; Zeisel et al., 2015), but at far lower sequencing coverage per cell.

Computational methods rooted in graph clustering to identify cell types in the data are applied. To assess the tradeoff between cell number and sequencing depth for resolving cell types, parallel experiments using conventional scRNA-seq, with the Smartseq2 protocol (Picelli et al., 2014) can be performed. To relate computationally defined clusters to known cell types for example BC types, use is made for example of previously described type-specific markers and transgenic lines. A generalizable validation method is developed, independent of reagent availability, which combines fluorescent in situ hybridization (FISH) with sparse viral labeling of cells such as BCs. Together, these approaches allow to match molecularly defined types with morphologically defined cell types.

The present disclosure addresses three key questions, two of which are rooted in technology: (1) how can one best use scRNA-seq to classify closely related cell types for example neuronal types, and (2) can large gene sets relevant for functional heterogeneity between cell types be identified from an unbiased inquiry? In answering these questions, a framework is provided that can be used as a starting point for analyses of other heterogeneous cell populations, for example in or outside of the nervous system. The third question is neurobiological: (3) what is the full cohort of the cell types for example of BC types? In answering this question, transcriptionally distinct cell types are identified. In an example of the present disclosure 15 transcriptionally distinct BC types were identified, including all types identified previously (Euler et al., 2014), as well as two types that have not previously been described. One of these types lacks morphological features that characterize other BCs, and has thereby escaped detection.

Further, the disclosure provides molecular markers for different cell types for example molecular markers for each BC type, including some for which no endogenous markers had previously been described. The vast majority of cells that were analyzed displayed the transcriptional profile of a single, discrete type, with scant evidence for the existence of intermediate cell types or a continuum of transcriptional identities.

Patterns of gene expression can be used to characterize and classify cell types, e.g., neuronal types. It is challenging according to the present disclosure however, to generate taxonomies that fulfill the essential criteria of being comprehensive, harmonizing with conventional classification schemes, and lacking superfluous subdivisions of genuine types. To address these challenges, massively parallel single-cell transcriptomic profiling and optimized computational methods are used on a heterogeneous class of cells, for example neurons such as mouse retinal bipolar cells (BCs).

In some aspects the present disclosure refers to a method of identifying a cell or cell marker, comprising: a) isolating target cells based on a marker specifically expressed in the cell or by label-free imaging flow cytometry; b) quantifying gene expression in the target cells by single cell sequencing, and c) clustering the target cells based on the gene expression by application of one or more algorithms, d) optionally determining a transcription signature for each cluster based at least in part on identifying differentially expressed genes between two or more clusters and between each cluster and the remaining cells as background, and e) optionally validating gene expression against cellular morphology.

Label-free imaging flow cytometry facilitates non-destructive monitoring of cells avoiding potentially confounding effects of fluorescent stains. It requires an annotated data set to train the machine-learning algorithm, either by staining a subset of the investigated cells with markers or by visual inspection and assignment of cell classes of interest.

Label-free imaging can likewise be used to determine histology of a "cell union" such as a tissue or an organ and thus, can be used to determine morphology. Also, here machine-learning algorithms are essential.

In other aspects the disclosure is directed to a method of determining transcription signatures for cell types or cell sub-types, comprising identifying cell types and/or cell sub-types by applying one or more clustering algorithms to a set of sequenced transcript reads from a population of cells, wherein each resulting cluster of sequenced transcript reads identifies a particular cell type or cell sub-type; and determining a transcription signature for each identified cell type or cell sub-type based at least in part on identifying differentially expressed transcripts between the identified cell type or cell sub-type.

Biomarkers and Signatures

In further aspects, the invention relates to a signature or set of biomarkers that may be detected in combination (e.g., cell markers determined by the methods disclosed herein). The terms "marker," "cell marker" and "biomarker" may be used interchangeably throughout this specification. The signature detected in combination may be a gene signature, protein signature, and/or other genetic or epigenetic signature of a particular cell (sub)population (e.g., retinal cells, immune cells). In certain embodiments, further markers (e.g., protein, and/or other genetic or epigenetic markers) may be determined for cell types identified by the present invention.

The term "biomarker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. Biomarkers as intended herein may be nucleic acid-based or peptide-, polypeptide- and/or protein-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or complementary DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilization of the cells.

Unless otherwise apparent from the context, reference herein to any marker, such as a peptide, polypeptide, protein, or nucleic acid, may generally also encompass modified forms of said marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native protein, such as, e.g., amino acid deletions, additions and/or substitutions. The term contemplates both full-length proteins and protein parts or fragments, e.g., naturally-occurring protein parts that ensue from processing of such full-length proteins.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually. The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500 or ≥600 consecutive amino acids of the corresponding full-length peptide, polypeptide, or protein.

The term "fragment" as used throughout this specification with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., ≥40 consecutive nucleotides, such as for example ≥50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

Cells such as bipolar cells as disclosed herein may in the context of the present specification be said to "comprise the expression" or conversely to "not express" one or more markers, such as one or more genes or gene products; or be described as "positive" or conversely as "negative" for one or more markers, such as one or more genes or gene products; or be said to "comprise" a defined "gene or gene product signature".

Such terms are commonplace and well-understood by the skilled person when characterizing cell phenotypes. By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

The present invention is also directed to signatures and uses thereof. As used herein a "signature" may encompass any gene or genes, protein or proteins, or epigenetic element(s) whose expression profile or whose occurrence is associated with a specific cell type, sub-type, or cell state of a specific cell type or sub-type within a population of cells (e.g., retinal cells, immune cells, tumor cells). In certain embodiments, the expression of the signatures are dependent on epigenetic modification of the genes or regulatory elements associated with the genes. Thus, in certain embodiments, use of signature genes includes epigenetic modifications that may be detected or modulated. For ease of discussion, when discussing gene expression, any gene or genes, protein or proteins, or epigenetic element(s) may be substituted. Reference to a gene name throughout the specification encompasses the human gene, mouse gene and all other orthologues as known in the art in other organisms. As used herein, the terms "signature", "expression profile", or "expression program" may be used interchangeably. It is to be understood that also when referring to proteins (e.g. differentially expressed proteins), such may fall within the definition of "gene" signature. As used herein, the term "transcriptional signature" may refer to the expression of genes or markers in a cell, tissue or organ under specific conditions. Levels of expression or activity or prevalence may be compared between different cells in order to characterize or identify for instance signatures specific for cell (sub)populations. Increased or decreased expression or activity of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or sub-type. A gene signature as used herein, may also refer to any set of up- and down-regulated genes between different cells or cell (sub)populations derived from a gene-expression profile. For example, a gene signature may comprise a list of genes differentially expressed in a distinction of interest (e.g., a pattern of gene expression).

The signature as defined herein (being it a gene signature, protein signature or other genetic or epigenetic signature) can be used to indicate the presence of a cell type, a sub-type of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. transgenic animals expressing cell specific markers in target cells, tissue samples, diseased tissue samples, populations of immune cells, tumor samples), thus allowing the discovery of novel cell subtypes or cell states that were previously invisible or unrecognized. The presence of sub-types or cell states may be determined by sub-type specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell sub-types having a particular signature may indicate an outcome. Not being bound by a theory, the signatures can be used to deconvolute the network of cells present in a particular pathological condition. Not being bound by a theory the presence of specific cells and cell sub-types are indicative of a particular response to treatment, such as including increased or decreased susceptibility to treatment. The signature may indicate the presence of one particular cell type.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular cell or cell (sub)population if it is upregulated or only present, detected or detectable in that particular cell or cell (sub)population, or alternatively is downregulated or only absent, or undetectable in that particular cell or cell (sub)population. In this context, a signature consists of one or more differentially expressed genes/proteins or differential epigenetic elements when comparing different cells or cell (sub)populations, including comparing different immune cell or immune cell (sub)populations, as well as comparing immune cell or immune cell (sub)populations with non-immune cell or non-immune cell (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population or subpopulation level, refer to genes that are differentially expressed in all or substantially all cells of the population or subpopulation (such as at least 80%, preferably at least 90%, such as at least 95% of the individual cells). This allows one to define a particular subpopulation of cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least two, at least three, at least four, at least five, at least six, or all genes/proteins and/or epigenetic elements of the signature.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In certain example embodiments, the signature genes may be used to deconvolute the network of cells present in a population of cells based on comparing them to data from bulk analysis of a sample (e.g., tumor sample). In certain example embodiments, the presence of specific cells and cell sub-types (e.g., immune cells) may be indicative of an outcome (e.g., tumor growth, invasiveness and/or resistance to treatment). In one example embodiment, detection of one or more signature genes may indicate the presence of a particular cell type or cell types.

Detection, Quantification and Isolation of Cell Types

In further aspects the disclosure relates to a method of identifying cell types or cell sub-types present in biological samples (e.g., classifying cell types). In certain embodiments, the disclosure relates to a method of identifying retinal cell types or retinal cell sub-types present in biological samples, comprising detecting one or more retinal cell transcription signatures in a sample comprising a cell population comprising retinal cells using single cell sequencing, wherein each transcription signature identifies a particular retinal cell type or retinal cell sub-type.

In certain embodiments, the present invention provides for a method comprising detecting or quantifying cells in a biological sample (e.g., retinal cell types). The presence of the cells in a sample may be detected after cells are broken (e.g., lysed, destroyed) or fixed and permeabilized. In an exemplary embodiment, cells are analyzed by single cell RNA sequencing (e.g., scRNA-seq) and the cells are sorted in silico based on gene expression attributed to each single cell. In another exemplary embodiment, fixed and permeabilized cells are analyzed by microscopy (e.g., fluorescent microscopy). In other embodiments, fixed and permeabilized cells may be detected and quantified using FACS. Thus, the specific cells may be detected in a biological sample and cell types quantitated even though the cells have been destroyed. In other embodiments, cells are detected or quantified from a sample using non-destructive methods, such as by using an affinity reagent specific to a cell surface marker.

In certain embodiments, the present invention provides for a method comprising isolating cells from a biological sample (e.g., retinal cell types). In certain embodiments, cells are isolated from a sample by using an affinity reagent specific to a cell surface marker.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or at least 60%, or at least 70%, or at least 80%, at least 90% or more, up to and including a 100% decrease (i.e., absent level as compared to a reference sample), or any decrease between 10-100% as compared to a reference level, as that.

In certain embodiments, the biological sample may comprise ex vivo or in vitro cells. The ex vivo or in vitro biological sample may be treated with a differentiation agent(s). The differentiating agent may be a cytokine or combination of cytokines. Not being bound by a theory, the ex vivo or in vitro biological sample may be differentiated to comprise certain types of cells. The ex vivo or in vitro biological sample may be treated with a perturbation (e.g., test agent). The test agent may be any agent predicted to affect the function or gene expression of any of the cells described herein. The agent may affect the ratio of cells in a population of cells (i.e., in the ex vivo or in vitro biological sample). In certain embodiments, the biological sample is assayed to determine the quantity or changes in composition of cells in the sample after treatment.

The terms "sample" or "biological sample" as used throughout this specification include any biological specimen obtained from a subject. Particularly useful samples are those known to comprise, or expected or predicted to comprise the cells as taught herein. Preferably, a sample may be readily obtainable by minimally invasive methods, such as blood collection or tissue biopsy, allowing the removal/isolation/provision of the sample from the subject. Examples of particularly useful samples include without limitation whole blood or a cell-containing fraction of whole blood, such as serum, white blood cells, or peripheral blood mononuclear cells (PBMC), lymph, lymphatic tissue, inflammation fluid, tissue specimens, or tissue biopsies. The term "tissue" as used throughout this specification refers to any animal tissue types including, but not limited to, bone, bone marrow, neural tissue, fibrous connective tissue, cartilage, muscle, vasculature, skin, adipose tissue, blood and glandular tissue or other non-bone tissue. The tissue may be healthy or affected by pathological alterations, e.g., tumor tissue or tissue affected by a disease comprising an immune component. The tissue may be from a living subject or may be cadaveric tissue. The tissue may be autologous tissue or syngeneic tissue or may be allograft or xenograft tissue. A biological sample may also include cells grown in tissue culture, such as cells used for screening drugs or primary cells grown in culture for expansion.

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value >second value; or decrease: first value <second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or ±1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

The terms "isolating" or "purifying" as used throughout this specification with reference to a particular component of a composition or mixture (e.g., the tested object such as the biological sample) encompass processes or techniques whereby such component is separated from one or more or (substantially) all other components of the composition or mixture (e.g., the tested object such as the biological sample). The terms do not require absolute purity. Instead, isolating or purifying the component will produce a discrete environment in which the abundance of the component relative to one or more or all other components is greater than in the starting composition or mixture (e.g., the tested object such as the biological sample). A discrete environment may denote a single medium, such as for example a single solution, dispersion, gel, precipitate, etc. Isolating or purifying the specified cells from the tested object such as the biological sample may increase the abundance of the specified cells relative to all other cells comprised in the tested object such as the biological sample, or relative to other cells of a select subset of the cells comprised in the tested object such as the biological sample. By means of example, isolating or purifying the specified cells from the tested object such as the biological sample may yield a cell population, in which the specified cells constitute at least 40% (by number) of all cells of said cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of said cell population.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of the specified cells in, or to isolate the specified cells from, a tested object (e.g., a cell population, tissue, organ, organism, or a biological sample of a subject). Such methods allow to detect, quantify or isolate the specified cells in or from the tested object (e.g., a cell population, tissue, organ, organism, or a biological sample of a subject) substantially to the exclusion of other cells comprised in the tested object. Such methods may allow to detect, quantify or isolate the specified cells with sensitivity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%, and/or with specificity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%. By means of example, at least 40% (by number), for example at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells detected, quantified or isolated by such methods may correspond to the specified immune cells.

Isolated Cells

In another aspect, the present invention provides for isolated cells as described herein. The isolated cell sub-types may be isolated using any of the markers described herein. The isolated cell sub-types may be isolated from a human subject. The isolated cell may be isolated from an ex vivo sample (e.g., cells grown in culture).

In one aspect, the invention is directed to isolated cell populations comprising the cells described herein and/or as identified by the signatures defined herein. Accordingly, methods for detecting, quantifying or isolating the specified immune cells may be marker-based or gene or gene product signature-based, i.e., may involve isolation of cells expressing or not expressing marker(s) or combination(s) of markers the expression or lack of expression of which is taught herein as typifying or characterizing the specified cells, or may involve detection, quantification or isolation of cells comprising gene or gene product signature(s) taught herein as typifying or characterizing the specified cells.

In another aspect, the present invention provides for a population of cells comprising cells as defined in any embodiment herein or isolated according to a method of any embodiment herein. The isolated population may comprise greater than 30%, 40%, 50%, 60%, 70%, 80%, 90% or 95% of a cell as defined in any embodiment herein. In certain embodiments, the population of cells is less than 30% of any one cell type, such as when cells are directly isolated from a patient. Not being bound by a theory, a population of cells isolated from a patient will include a heterogeneous population of cells, such that specific cell sub-types make up less than a majority of the total cells (e.g., less than 30%, 20%, 10%, 5%, or 1%). In certain embodiments, a sub-type of cells is expanded or enriched ex vivo to obtain a non-naturally occurring cell population enriched for certain cell types. In certain embodiments, cells according to the present invention are depleted from a population of cells. The isolated population may comprise less than 5%, 1%, 0.1%, 0.01%, or 0.001%, or comprise 0% of a cell as defined in any embodiment herein. In certain embodiments, cell functions may be determined by depleting cell sub types.

The isolated cells or cell populations as disclosed throughout this specification may be suitably cultured or cultivated in vitro. The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v $CO_2$ and >95% humidity.

The term "medium" as used herein broadly encompasses any cell culture medium conducive to maintenance of cells, preferably conducive to proliferation of cells. Typically, the medium will be a liquid culture medium, which facilitates easy manipulation (e.g., decantation, pipetting, centrifugation, filtration, and such) thereof.

Typically, the medium will comprise a basal medium formulation as known in the art. Many basal media formulations (available, e.g., from the American Type Culture Collection, ATCC; or from Invitrogen, Carlsbad, Calif.) can be used, including but not limited to Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Liebovitz L-15, DMEM/F-12, Essential Modified Eagle's Medium (EMEM), RPMI-1640, Medium 199, Waymouth's MB 752/1 or Williams Medium E, and modifications and/or combinations thereof. Compositions of basal media are generally known in the art and it is within the skill of one in the art to modify or modulate concentrations of media and/or media supplements as necessary for the cells cultured.

Such basal media formulations contain ingredients necessary for mammalian cell development, which are known per se. By means of illustration and not limitation, these ingredients may include inorganic salts (in particular salts containing Na, K, Mg, Ca, Cl, P and possibly Cu, Fe, Se and Zn), physiological buffers (e.g., HEPES, bicarbonate), nucleotides, nucleosides and/or nucleic acid bases, ribose, deoxyribose, amino acids, vitamins, antioxidants (e.g., glutathione) and sources of carbon (e.g., glucose, sodium pyruvate, sodium acetate), etc.

For use in culture, basal media can be supplied with one or more further components. For example, additional supplements can be used to supply the cells with the necessary trace elements and substances for optimal growth and expansion. Furthermore, antioxidant supplements may be added, e.g., β-mercaptoethanol. While many basal media already contain amino acids, some amino acids may be supplemented later, e.g., L-glutamine, which is known to be less stable when in solution. A medium may be further supplied with antibiotic and/or antimycotic compounds, such as, typically, mixtures of penicillin and streptomycin, and/or other compounds, exemplified but not limited to, amphotericin, ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Lipids and lipid carriers can also be used to supplement cell culture media. Such lipids and carriers can include, but are not limited to cyclodextrin, cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulations.

Also contemplated is supplementation of cell culture media with mammalian plasma or sera. Plasma or sera often contain cellular factors and components that facilitate cell viability and expansion. Optionally, plasma or serum may be heat inactivated. Heat inactivation is used in the art mainly to remove the complement. Heat inactivation typically involves incubating the plasma or serum at 56° C. for 30 to 60 min, e.g., 30 min, with steady mixing, after which the plasma or serum is allowed to gradually cool to ambient temperature. A skilled person will be aware of any common modifications and requirements of the above procedure. Optionally, plasma or serum may be sterilized prior to storage or use. Usual means of sterilization may involve, e.g., filtration through one or more filters with pore size smaller than 1 μm, preferably smaller than 0.5 μm, e.g., smaller than 0.45 μm, 0.40 μm, 0.35 μm, 0.30 μm or 0.25 μm, more preferably 0.2 μm or smaller, e.g., 0.15 μm or smaller, 0.10 μm or smaller. Suitable sera or plasmas for use in media as taught herein may include human serum or plasma, or serum or plasma from non-human animals, preferably non-human mammals, such as, e.g., non-human primates (e.g., lemurs, monkeys, apes), fetal or adult bovine, horse, porcine, lamb, goat, dog, rabbit, mouse or rat serum or plasma, etc., or any combination of such. In certain preferred embodiments, a medium as taught herein may comprise bovine serum or plasma, preferably fetal bovine (calf) serum or plasma, more preferably fetal bovine (calf) serum (FCS or FBS). When culturing human cells, media may preferably comprise human serum or plasma, such as autologous or allogeneic human serum or plasma, preferably human serum, such as autologous or allogeneic human serum, more preferably autologous human serum or plasma, even more preferably autologous human serum.

In certain preferred embodiments, serum or plasma can be substituted in media by serum replacements, such as to provide for serum-free media (i.e., chemically defined media). The provision of serum-free media may be advantageous particularly with view to administration of the media or fraction(s) thereof to subjects, especially to human subjects (e.g., improved bio-safety). By the term "serum replacement" it is broadly meant any a composition that may be used to replace the functions (e.g., cell maintenance and growth supportive function) of animal serum in a cell culture medium. A conventional serum replacement may typically comprise vitamins, albumin, lipids, amino acids, transferrin, antioxidants, insulin and trace elements. Many commercialized serum replacement additives, such as KnockOut Serum Replacement (KOSR), N2, B27, Insulin-Transferrin-Selenium Supplement (ITS), and G5 are well known and are readily available to those skilled in the art.

Plasma or serum or serum replacement may be comprised in media as taught herein at a proportion (volume of plasma or serum or serum replacement/volume of medium) between about 0.5% v/v and about 40.0% v/v, preferably between about 5.0% v/v and about 20.0% v/v, e.g., between about 5.0% v/v and about 15.0% v/v, more preferably between about 8.0% v/v and about 12.0% v/v, e.g., about 10.0% v/v.

Methods of Detection and Isolation of Cells Using Biomarkers

In certain embodiments, cell sub-types may be detected, quantified or isolated using a technique selected from the group consisting of flow cytometry, mass cytometry, fluorescence activated cell sorting (FACS), fluorescence microscopy, affinity separation, magnetic cell separation, microfluidic separation, RNA-seq (e.g., bulk or single cell), quantitative PCR, MERFISH (multiplex (in situ) RNA FISH) and combinations thereof. The technique may employ one or more agents capable of specifically binding to one or more gene products expressed or not expressed by the cells, preferably on the cell surface of the cells. The one or more agents may be one or more antibodies. Other methods including absorbance assays and colorimetric assays are known in the art and may be used herein.

Depending on factors that can be evaluated and decided on by a skilled person, such as, inter alia, the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

n other example embodiments, detection of a marker may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (MA), Western blot, etc.

In certain example embodiments, detection of a marker or signature may include biochemical assay methods, including inter alia assays of enzymatic activity, membrane channel activity, substance-binding activity, gene regulatory activity, or cell signaling activity of a marker, e.g., peptide, polypeptide, protein, or nucleic acid.

In other example embodiments, detection of a marker may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)n (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)n; atmospheric pressure photoionization mass spectrometry (APPI-MS); APPI-MS/MS; and APPI-(MS)n. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

In other example embodiments, detection of a marker may include chromatography methods. In a one example embodiment, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography may be columnar. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilized metal affinity chromatography, and the like.

In certain embodiments, further techniques for separating, detecting and/or quantifying markers may be used in conjunction with any of the above described detection methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridization-based analysis, microarray expression analysis, digital gene expression profiling (DGE), RNA-in-situ hybridization (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (sc-RNA seq), or the like. By means of an example, methods to profile the RNA content of large numbers of individual cells have been developed. The cell of origin is determined by a cellular barcode. In certain embodiments, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from. In these regards, reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO 2014210353 A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; and Rosenberg et al., 2017, "Scaling single cell transcriptomics through split pool barcoding" bioRxiv preprint first posted online Feb. 2, 2017, doi: dx.doi.org/10.1101/105163, all the contents and disclosure of each of which are herein incorporated by reference in their entirety.

In certain embodiments, the invention involves single nucleus RNA sequencing, especially for identifying populations of cells that are difficult to obtain or isolate (e.g., neurons). In this regard, reference is made to Swiech et al., 2014, "In vivo interrogation of gene function in the mammalian brain using CRISPR-Cas9" Nature Biotechnology Vol. 33, pp. 102-106; and Habib et al., 2016, "Div-Seq: Single-nucleus RNA-Seq reveals dynamics of rare adult newborn neurons" Science, Vol. 353, Issue 6302, pp. 925-928, both of which are herein incorporated by reference in their entirety.

In certain embodiments, the invention involves targeted nucleic acid profiling (e.g., sequencing, quantitative reverse transcription polymerase chain reaction, and the like) (see e.g., Geiss G K, et al., Direct multiplexed measurement of gene expression with color-coded probe pairs. Nat Biotechnol. 2008 March; 26(3):317-25). In certain embodiments, sequencing may be performed by any method known in the art, for example, methods of high-throughput sequencing, also known as next generation sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others. Methods for constructing sequencing libraries are known in the art (see, e.g., Head et al., Library construction for next-generation sequencing: Overviews and challenges. Biotechniques. 2014; 56(2): 61-77).

In some aspects of the disclosure the single cell sequencing is a high-throughput single cell RNA sequencing. In certain embodiments, the single cell sequencing is a low cost high-throughput single cell RNA sequencing. Not being bound by a theory, the single cell RNA sequencing is capable of efficiently and cost effectively sequencing thousands to tens of thousands of single cells. In certain embodiments, single cell RNA sequencing comprises pairing single cells in droplets with oligonucleotides for reverse transcription, wherein the oligonucleotides are configured to provide cell-of-origin specific barcodes uniquely identifying transcripts from each cell and a unique molecular identifier (UMI) uniquely identifying each transcript. In certain embodiments, single cell RNA sequencing comprises pairing single cells in droplets with single microparticle beads coated with oligonucleotides for reverse transcription, wherein the oligonucleotides contain a bead-specific barcode uniquely identifying each bead and a unique molecular identifier (UMI) uniquely identifying each primer.

In some aspects of the disclosure, unbiased classifying of cells in a biological sample comprises sequencing the transcriptomes of thousands of cells, preferably tens of thousands of cells (e.g., greater than 1000 cells, preferably greater than 10,000 cells). Applicants show that the number of cells analyzed is a critical factor and deep sequencing at depths of 800,000 mapped reads per cell is not required for identifying cell types in a heterogeneous sample. Applicants show that a greater sequencing depth per cell is insufficient to compensate for the under representation of cell types. Not being bound by a theory, identifying cells that represent a low percentage of cells in the biological sample (e.g., 0.1%, 1%, 5%) require sequencing thousands of cells to allow a high probability that all cell types are sampled. Not being bound by a theory, identifying all cells in a biological sample requires sequencing thousands, preferably tens of thousands of cells to allow a high probability that all cell types are sampled and identified. In certain embodiments, cell types can be first identified by sequencing a high number of cells with low coverage, second isolated based on cell type specific markers and third further characterized using a plate-based near full-length RNA-seq method as described herein.

The terms "depth" or "coverage" as used herein refers to the number of times a nucleotide is read during the sequencing process. In regards to single cell RNA sequencing, "depth" or "coverage" as used herein refers to the number of mapped reads per cell. Depth in regards to genome sequencing may be calculated from the length of the original genome (G), the number of reads (N), and the average read length (L) as N×L/G. For example, a hypothetical genome with 2,000 base pairs reconstructed from 8 reads with an average length of 500 nucleotides will have 2× redundancy.

In certain embodiments, the method disclosed herein may allow to detect or conclude the presence or absence of the specified cells in a tested object (e.g., in a cell population, tissue, organ, organism, or in a biological sample of a subject). The method may also allow to quantify the specified cells in a tested object (e.g., in a cell population, tissue, organ, organism, or in a biological sample of a subject). The quantity of the specified cells in the tested object such as the biological sample may be suitably expressed for example as the number (count) of the specified cells per standard unit of volume (e.g., ml, µl or nl) or weight (e.g., g or mg or ng) of the tested object such as the biological sample. The quantity of the specified cells in the tested object such as the biological sample may also be suitably expressed as a percentage or fraction (by number) of all cells comprised in the tested object such as the biological sample, or as a percentage or fraction (by number) of a select subset of the cells comprised in the tested object such as the biological sample, e.g., as a percentage or fraction (by number) of bipolar cells comprised in the tested object such as the biological sample. The quantity of the specified cells in the tested object such as the biological sample may also be suitably represented by an absolute or relative quantity of a suitable surrogate analyte, such as a peptide, polypeptide, protein, or nucleic acid expressed or comprised by the specified cells.

Where a marker is detected in or on a cell, the cell may be conventionally denoted as positive (+) or negative (−) for the marker. Semi-quantitative denotations of marker expression in cells are also commonplace in the art, such as particularly in flow cytometry quantifications, for example, "dim" vs. "bright", or "low" vs. "medium"/"intermediate" vs. "high", or "−" vs. "+" vs. "++", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed as a percentage or fraction (by number) of cells comprised in said population that are positive for said marker, or as percentages or fractions (by number) of cells comprised in said population that are "dim" or "bright", or that are "low" or "medium"/"intermediate" or "high", or that are "−" or "+" or "++". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

In certain embodiments, methods for detecting, quantifying or isolating the specified cells may be single-cell-based, i.e., may allow to discretely detect, quantify or isolate the specified cells as individual cells. In other embodiments, methods for detecting, quantifying or isolating the specified cells may be cell population-based, i.e., may only allow to detect, quantify or isolate the specified cells as a group or collection of cells, without providing information on or allowing to isolate individual cells.

Methods for detecting, quantifying or isolating the specified cells may employ any of the above-described techniques for measuring markers, insofar the separation or the qualitative and/or quantitative measurement of the marker(s) can be correlated with or translated into detection, quantification or isolation of the specified cells. For example, any of the above-described biochemical assay methods, immunological assay methods, mass spectrometry analysis methods, chromatography methods, or nucleic acid analysis method, or combinations thereof for measuring markers, may be employed for detecting, quantifying or isolating the specified cells.

In certain embodiments, the cells are detected, quantified or isolated using a technique selected from the group consisting of flow cytometry, fluorescence activated cell sorting, mass cytometry, fluorescence microscopy, affinity separation, magnetic cell separation, microfluidic separation, and combinations thereof.

Flow cytometry encompasses methods by which individual cells of a cell population are analyzed by their optical properties (e.g., light absorbance, light scattering and fluorescence properties, etc.) as they pass in a narrow stream in single file through a laser beam. Flow cytometry methods include fluorescence activated cell sorting (FACS) methods by which a population of cells having particular optical properties are separated from other cells.

Elemental mass spectrometry-based flow cytometry, or mass cytometry, offers an approach to analyze cells by replacing fluorochrome-labelled binding reagents with mass tagged binding reagents, i.e., tagged with an element or isotope having a defined mass. In these methods, labeled particles are introduced into a mass cytometer, where they are individually atomized and ionized. The individual particles are then subjected to elemental analysis, which identifies and measures the abundance of the mass tags used. The identities and the amounts of the isotopic elements associated with each particle are then stored and analyzed. Due to the resolution of elemental analysis and the number of elemental isotopes that can be used, it is possible to simultaneously measure up to 100 or more parameters on a single particle.

Fluorescence microscopy broadly encompasses methods by which individual cells of a cell population are microscopically analyzed by their fluorescence properties. Fluorescence microscopy approaches may be manual or preferably automated.

Affinity separation also referred to as affinity chromatography broadly encompasses techniques involving specific interactions of cells present in a mobile phase, such as a suitable liquid phase (e.g., cell population in an aqueous suspension) with, and thereby adsorption of the cells to, a stationary phase, such as a suitable solid phase; followed by separation of the stationary phase from the remainder of the mobile phase; and recovery (e.g., elution) of the adsorbed cells from the stationary phase. Affinity separation may be columnar, or alternatively, may entail batch treatment, wherein the stationary phase is collected/separated from the liquid phases by suitable techniques, such as centrifugation or application of magnetic field (e.g., where the stationary phase comprises magnetic substrate, such as magnetic particles or beads). Accordingly, magnetic cell separation is also envisaged herein.

Microfluidic systems allow for accurate and high throughput cell detection, quantification and/or sorting, exploiting a variety of physical principles. Cell sorting on microchips provides numerous advantages by reducing the size of necessary equipment, eliminating potentially biohazardous aerosols, and simplifying the complex protocols commonly associated with cell sorting. The term "microfluidic system" as used throughout this specification broadly refers to systems having one or more fluid microchannels. Microchannels denote fluid channels having cross-sectional dimensions the largest of which are typically less than 1 mm, preferably less than 500 µm, more preferably less than 400 µm, more preferably less than 300 µm, more preferably less than 200 µm, e.g., 100 µm or smaller. Such microfluidic systems can be used for manipulating fluid and/or objects such as droplets, bubbles, capsules, particles, cells and the like. Microfluidic systems may allow for example for fluorescent label-based (e.g., employing fluorophore-conjugated binding agent(s), such as fluorophore-conjugated antibody(ies)), bead-based (e.g., bead-conjugated binding agent(s), such as bead-conjugated antibody(ies)), or label-free cell sorting (reviewed in Shields et al., Lab Chip. 2015, vol. 15: 1230-1249).

Use of Specific Binding Agents

In certain embodiments, the aforementioned methods and techniques may employ agent(s) capable of specifically binding to one or more gene products, e.g., peptides, polypeptides, proteins, or nucleic acids, expressed or not expressed by the cells as taught herein. In certain preferred embodiments, such one or more gene products, e.g., peptides, polypeptides, or proteins, may be expressed on the cell surface of the cells (i.e., cell surface markers, e.g., transmembrane peptides, polypeptides or proteins, or secreted peptides, polypeptides or proteins which remain associated with the cell surface). Hence, further disclosed are binding agents capable of specifically binding to markers, such as genes or gene products, e.g., peptides, polypeptides, proteins, or nucleic acids as taught herein. Binding agents as intended throughout this specification may include inter alia antibodies, aptamers, spiegelmers (L-aptamers), photoaptamers, protein, peptides, peptidomimetics, nucleic acids such as oligonucleotides (e.g., hybridization probes or amplification or sequencing primers and primer pairs), small molecules, or combinations thereof.

The term "aptamer" refers to single-stranded or double-stranded oligo-DNA, oligo-RNA or oligo-DNA/RNA or any analogue thereof that specifically binds to a target molecule such as a peptide. Advantageously, aptamers display fairly high specificity and affinity (e.g., KA in the order $1 \times 10^9$ $M^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

Binding agents may be in various forms, e.g., lyophilised, free in solution, or immobilised on a solid phase. They may be, e.g., provided in a multi-well plate or as an array or microarray, or they may be packaged separately, individually, or in combination.

The term "specifically bind" as used throughout this specification means that an agent (denoted herein also as "specific-binding agent") binds to one or more desired molecules or analytes (e.g., peptides, polypeptides, proteins, or nucleic acids) substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold, or at least about 1000-fold, or at least about 104-fold, or at least about 105-fold, or at least about 106-fold or more greater, than its affinity for a non-target molecule, such as for a suitable control molecule (e.g., bovine serum albumin, casein).

Preferably, the specific binding agent may bind to its intended target(s) with affinity constant (KA) of such binding $KA \geq 1 \times 10^6$ $M^{-1}$, more preferably $KA \geq 1 \times 10^7$ $M^{-1}$, yet more preferably $KA \geq 1 \times 10^8$ $M^{-1}$, even more preferably $KA \geq 1 \times 10^9$ $M^{-1}$, and still more preferably $KA \geq 1 \times 10^{10}$ $M^{-1}$ or $KA \geq 1 \times 10^{11}$ $M^{-1}$ or $KA \geq 1 \times 10^{12}$ $M^{-1}$, wherein $KA = [SBA\_T]/[SBA][T]$, SBA denotes the specific-binding agent, T denotes the intended target. Determination of KA can be carried out by methods known in the art, such as for example, using equilibrium dialysis and Scatchard plot analysis.

In certain embodiments, the one or more binding agents may be one or more antibodies. As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest, i.e., antigen-binding fragments), as well as multivalent and/or multi-specific composites of such fragments. The term "antibody" is not only inclusive of antibodies generated by methods comprising immunization, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo. Antibodies also encompasses chimeric, humanized and fully humanized antibodies.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments, single domain (sd) Fv, such as VH domains, VL domains and VHH domains; diabodies; linear antibodies; single-chain antibody molecules, in particular heavy-chain antibodies; and multivalent and/or multispecific antibodies formed from antibody fragment(s), e.g., diabodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromedarius*), llama (e.g., *Lama pacos, Lama glama* or *Lama vicugna*) or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbor Laboratory, New York, 1988; Harlow and Lane, "Using Antibodies: A Laboratory Manual", Cold Spring Harbor Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2): 237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptidomimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins—harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

Nucleic acid binding agents, such as oligonucleotide binding agents, are typically at least partly antisense to a target nucleic acid of interest. The term "antisense" generally refers to an agent (e.g., an oligonucleotide) configured to specifically anneal with (hybridize to) a given sequence in a target nucleic acid, such as for example in a target DNA, hnRNA, pre-mRNA or mRNA, and typically comprises, consist essentially of or consist of a nucleic acid sequence that is complementary or substantially complementary to said target nucleic acid sequence. Antisense agents suitable for use herein, such as hybridization probes or amplification or sequencing primers and primer pairs) may typically be capable of annealing with (hybridizing to) the respective target nucleic acid sequences at high stringency conditions, and capable of hybridizing specifically to the target under physiological conditions. The terms "complementary" or "complementarity" as used throughout this specification with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C-U-3'.

The reference to oligonucleotides may in particular but without limitation include hybridization probes and/or amplification primers and/or sequencing primers, etc., as commonly used in nucleic acid detection technologies.

Binding agents as discussed herein may suitably comprise a detectable label. The term "label" refers to any atom, molecule, moiety or biomolecule that may be used to provide a detectable and preferably quantifiable read-out or property, and that may be attached to or made part of an entity of interest, such as a binding agent. Labels may be suitably detectable by for example mass spectrometric, spectroscopic, optical, colorimetric, magnetic, photochemical, biochemical, immunochemical or chemical means. Labels include without limitation dyes; radiolabels such as $^{32}$P, $^{33}$P, $^{35}$S, $^{125}$I, $^{131}$I; electron-dense reagents; enzymes (e.g., horse-radish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that may suppress or shift emission spectra by fluorescence resonance energy transfer (FRET).

In some embodiments, binding agents may be provided with a tag that permits detection with another agent (e.g., with a probe binding partner). Such tags may be, for example, biotin, streptavidin, his-tag, myc tag, maltose, maltose binding protein or any other kind of tag known in the art that has a binding partner. Example of associations which may be utilised in the probe:binding partner arrangement may be any, and includes, for example biotin:streptavidin, his-tag:metal ion (e.g., Ni2+), maltose:maltose binding protein, etc.

The marker-binding agent conjugate may be associated with or attached to a detection agent to facilitate detection. Examples of detection agents include, but are not limited to, luminescent labels; colorimetric labels, such as dyes; fluorescent labels; or chemical labels, such as electroactive agents (e.g., ferrocyanide); enzymes; radioactive labels; or radiofrequency labels. The detection agent may be a particle. Examples of such particles include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles may be colloidal gold particles.

In certain embodiments, the one or more binding agents are configured for use in a technique selected from the group consisting of flow cytometry, fluorescence activated cell sorting, mass cytometry, fluorescence microscopy, affinity separation, magnetic cell separation, microfluidic separation, and combinations thereof.

In other aspects the disclosure refers to a method for cell perturbation screening, comprising exposing a test cell population to one or more perturbations; detecting one or more cell transcription signatures in a sample by single cell sequencing of transcripts expressed in the cell population, wherein the one or more transcription signatures indicates an absence or presence of a particular cell type or cell sub-type in the sample.

In some examples of these aspects the one or more perturbation(s) comprise(s) exposing the sample to one or more chemical agents, a concentration range of one or more chemical agents, or both. In other examples of these aspects the absence or presence of a particular cell type or cell sub-type indicates a propensity of the one or more perturbations to cause blindness. In other examples of these aspects, the method for cell perturbation screening forms the basis for a kit for testing pharmaceutical or chemical compounds, wherein the kit comprises for example a support such as a 96-well plate comprising retinal cells such as BCs.

In some examples of the previous aspects the transcription signatures identify a neuronal cell sub-type such as a bipolar cell sub-type. The bipolar cell is for example on the basis of type of glutamate receptor, acetylcholine receptors, potassium channels, transcription factors, and/or adhesion/recognition molecules.

In some examples of the previous aspects the transcription signature identifies a rod bipolar cell, or one of the following cone bipolar cells: BC1A, BC1B, BC2, BC3A, BC3B, BC4, BC5A, BC5B, BC5C, BC5D (XBC), BC6, BC7, BC8, and BC9. The transcription signature comprises for example at least one of Pcdh17, Pcdh10, Erbb4, Nnat, Col11a1, Sox6, Chrm2, Slitrk5, Lrrtm1, Cck, Lect1, Igfn1, Serpini1, Cpne9, Vstm2b, Casp7, Vsx1, Vsx2, Otx2, Scgn, Slc1a2, Slc6a9, Pax6, Tfap2a, Stx1b, Tacr3, Bhlhe23, Fat4, Fezf1, Fezf2, Wfdc2, Mylk, Hs3st2, Wls, Nxph1, Lhx3, Cabp5, Grm6, Kcng4, Cdh9, Htr3a, Hcn1, Hcn4, Nfia, Cntn5, BC046251, Gfra3, Areg, Kirrel3, Isl1, Spock3, Serpini1, Prkca, Car8, Sebox, Apoe, GluI, Aqp4, Cabp5, Syt2, Grik1, Prkar2b, Rcvrn, Irx6, Gad1, Rho, Pdc, Nrl, Pde6a, Pde6h, Arr3, Opn1mw, and Opn1sw.

If the transcription signature identifies a BC1A sub-type, it comprises for example one of more of Pcdh17, Pcdh10, Cpne9, Vsx2, Otx2, Scgn, Slc1a2, Tacr3, Bhlhe23, Fat4, Fezf2, Wfdc2, Mylk, Hs3st2, and Wls. If the transcription signature identifies a BC1B sub-type, it comprises for example one or more of Pcdh10, Vsx2, Otx2, Scgn, Slc1a2, Tacr3, Bhlhe23, Fat4, Pcdh17, Fezf2, Wls, Nxph1, Lhx3, and Fezf1. If the transcription signature identifies a BC2 sub-type, it comprises for example one or more of Chrm2, Vsx2, Otx2, Scgn, Tacr2, Syt2, and Rcvrn. If the transcription signature identifies a BC3A sub-type, it comprises for example one or more of Erbb4, Nnat, Vsx2, Otx2, Scgn, Irx6, and Hcn4. If the transcription signature identifies a BC3B sub-type, it comprises for example one or more of Nnat, Sox6, Vsx2, Otx2, Scgn, Grik1, and Prkar2b. If the transcription signature identifies a BC4 sub-type, it comprises for example one or more of Nnat, Col11a1, Vsx2, Otx2, Scgn, and Grik1. If the transcription signature identifies a BC5A sub-type, it comprises for example one or more of Nnat, Sox6, Lrrtm1, Vsx2, Otx2, Scgn, Grm6, Isl6, Cabp5, Hcn1, Kcng4, and Nf1a, Cntn5, and BC0465251. If the transcription signature identifies a BC5B sub-type, it comprises for example one or more of Pcdh17, Nnat, Chrm2, Vsx2, Otx2, Scgn, Grm6, Isl1, Cabp5, Hcn1, Nfia, Cntn5, and Gfra3. If the transcription signature identifies a BC5C sub-type, it comprises for example one or more of Pcdh17, Pcdh10, Slitrk5, Vsx2, Otx2, Scgn, Grm6, Isl1, Nfia, BC046251, Lrrtm1, Kirrel3, Slitrk5, and Areg. If the transcription signature identifies a BC5D sub-type, it comprises for example one or more of Nnat, Lrrtm1, Vsx2, Otx2, Isl1, Cabp5, Hcn1, and Kcng4. If the transcription signature identifies a BC6 sub-type, it comprises for example one or more of Cck, Lect1, Vsx2, Otx2, Scgn, Grm6, Isl1, Vsx1, and Syt2. If the transcription signature identifies a BC7 sub-type, it comprises for example one or more of Igfn1, Vsx2, Otx2, Grm6, Isl1, and Vsx1. If the transcription signature identifies a BC8/9 sub-type, it comprises for example one or more of Nnat, Serpini1, Cpn39, Vsx2, Otx2, Grm6, and Isl1. If the transcription signature identifies a rod bipolar cell sub-type, it comprises for example one or more of Vstm2b, Casp7, Rho, Pdc, Nrl, and Pde6a. If the transcription signature identifies a BC2 sub-type, it comprises for example Lhx3 alone or in addition to Tacr3 or Nxph1.

In other examples of the previous aspects the transcription signature identifies a BC1B sub-type and comprises at least Pcdh10. If the transcription signature identifies a BC2 sub-type, it comprises at least Chrm2. If the transcription signature identifies a BC3A sub-type, it comprises at least Erbb4 and Nnat. If the transcription signature identifies a BC3B sub-type, it comprises at least Nnat and Sox6. If the transcription signature identifies a BC4 sub-type, it comprises at least Nnat and Col11a1. If the transcription signature identifies a BC5A sub-type, it comprises at least Nnat, Sox6, and Lrrtm1. If the transcription signature identifies a BC5B sub-type, it comprises at least Pcdh17, Nnat, and Chrm2. If the transcription signature identifies a BC5C sub-type, it comprises at least Pcdh17, Pcdh10, and Slitrk5. If the transcription signature identifies a BC5D sub-type, it comprises at least Nnat, and Lrrtm1. If the transcription signature identifies a BC6 sub-type, it comprises at least Cck and Lect1. If the transcription signature identifies a BC7 sub-type, it comprises at least Igfn1. If the transcription signature identifies a BC8/9 sub-type and comprises at least Nnat, Serpini1, and Cpn39. If the transcription signature identifies a BC8 sub-type, it comprises for example at least Serpini1. If the transcription signature identifies a BC9 sub-type, it comprises for example at least Serpini1 and Cpne9.

In other examples of the previous aspects (optional) validating gene expression against cellular morphology comprises sparse labeling the cell to enhance the expression of a fluorescent protein in the cell and combining the sparse labeling with fluorescent in situ hybridization (FISH) to validate the marker against cellular morphology in step e). In examples of the previous aspects FISH is for example combined with a specific antibody, double FISH or a transgenic reporter mouse line directed to a previously identified marker in the cell. For example an enhancer element is inserted into a lentivirus or an adeno-associated virus (AAV) vector upstream of the fluorescent protein to enhance its expression.

In some examples of the present disclosure identifying differentially expressed transcripts comprises application of a supervised or unsupervised machine-learning model. A supervised machine learning model is for example selected from the group consisting of an analytical learning model, an artificial neural network model, a back propagation model, a boosting model, a Bayesian statistics model, a case-based model, a decision tree learning model, an inductive logic programming model, a Gaussian process regression model, a group method of data handling model, a kernel estimator model, a learning automata model, a minimum message length model, a multilinear subspace learning, a naïve bayes classifer model, a nearest neighbor model, a probably approximately correct (PAC) learning model, a ripple down rules model, a symbolic machine learning model, a subsymbolic machine learning model, a support vector machine learning model, a minimum complexity machine model, a random forest model, an ensemble of classifiers model, an ordinal classification model, a data pre-processing model, a handling imbalanced datasets model, a statistical relational learning model, a Proaftn model. An unsupervised machine learning model is for example selected from the group consisting of a k-means model, a mixture model, a hierarchical clustering model, an anomaly detection model, a neural network model, an expectation-maximization (EM) model, a method of moments model, or a blind signal separation technique.

These models are used separately or in combination with each other or in combination with any other machine-learning model, wherein a supervised model is combined with a supervised model, or an unsupervised model is combined with an unsupervised model or a supervised model is combined with an unsupervised model.

In further aspects the disclosure is directed to a bipolar cell for example a bipolar cell BC1A characterized by expression of Pcdh17 and Fezf2; or to a bipolar cell BC1B characterized by expression of Pcdh10 and Fezf1; or to a bipolar cell BC5A characterized by expression of Sox6, B046251, Cntn5, Lrrtm1, Nnat, Htr3a, Kcng4, and Nfia; or to a bipolar cell BC5B characterized by expression of Pcdh17, Nfia, Cntn5, Gfra3, Chrm2, and Nnat; or to a bipolar cell BC5C characterized by expression of Pcdh17, Pcdh10, Cntn5, Slitrk5 and Areg; or to a bipolar cell BC5D characterized by expression of Nnat, B046251, Kirrel3, Htr3a and Kcng4, Lact1, Lrrtm1 and Nfia; or to a bipolar cell BC8 characterized by Serpini$^+$ Cpne$^-$; or to a bipolar cell BC9 characterized by Serpini$^+$ Cpne$^+$ and optionally an exclusion zone of 14.3 μm where no other Cpne$^+$ cells are positioned.

Thus, the present disclosure provides in some aspects methods for the understanding of cell atlases of different tissues, from a molecular taxonomy of the cell type and its defining molecular component(s), to the regulatory circuits that generate this taxonomy, and that control cell differentiation and function. This provides genetic access to selectively label and manipulate specific cell types, enabling the unification of structural, physiological and molecular features, and is a starting point to link genetic associations defined by population studies to cellular mechanisms which for example underlay cellular disorders.

In the present disclosure an integrated strategy for building a comprehensive validated atlas of cell types, for example in the nervous system, is developed and applied. The following interrelated challenges were taken on which are associated with: (1) the need to harmonize different definitions of cell type (here, molecular and morphological); (2) a population containing both abundant and rare cell types; (3) the need for a scalable and robust computational approach to define cell types and molecular markers; and (4) the trade-off between the depth of profiling and the number of profiled cells, given fixed resources. Applicants optimized the strategy using mouse BCs. It is shown that the classification is comprehensive based on the example of BCs in covering all known types, and that associated transcriptional profiles are accurate, identifying the majority of known markers and new ones, many of which were validated. Two new BC types (including one with a non-canonical morphology) and generated an extensive resource for future studies in the retina. The present disclosure provides an experimental and computational framework for corresponding studies in other systems.

BCs are an ideal class for evaluating scRNA-seq: 1) BC types have been thoroughly classified morphologically at both light and electron microscopic levels (Helmstaedter et al., 2013; Wassle et al., 2009). These studies also introduced a stringent criterion for cell type—the tendency of single types to avoid arbor overlap, called tiling. 2) BCs are accessible to labeling by electroporation or viral infection. The Vsx2 enhancer was used for example, which drives expression specifically in BCs, to construct a lentivirus to sparsely label BCs and visualize their morphology (Emerson and Cepko, 2011). Coupling this experimental access with FISH allow to validate candidate marker expression with respect to morphological classifications of BC types. This genetic access has also facilitated studies of development (Wang et al., 2014), as well as manipulation of these cell types (Duan et al., 2014), and future genetic studies will benefit from the new markers identified here. 3) Endogenous and transgenic markers were already available for some BC types, aiding the validation of BC type assignment to each cluster and allowing us to assess the accuracy of computational approaches at an early stage of the analysis.

Figure 11:
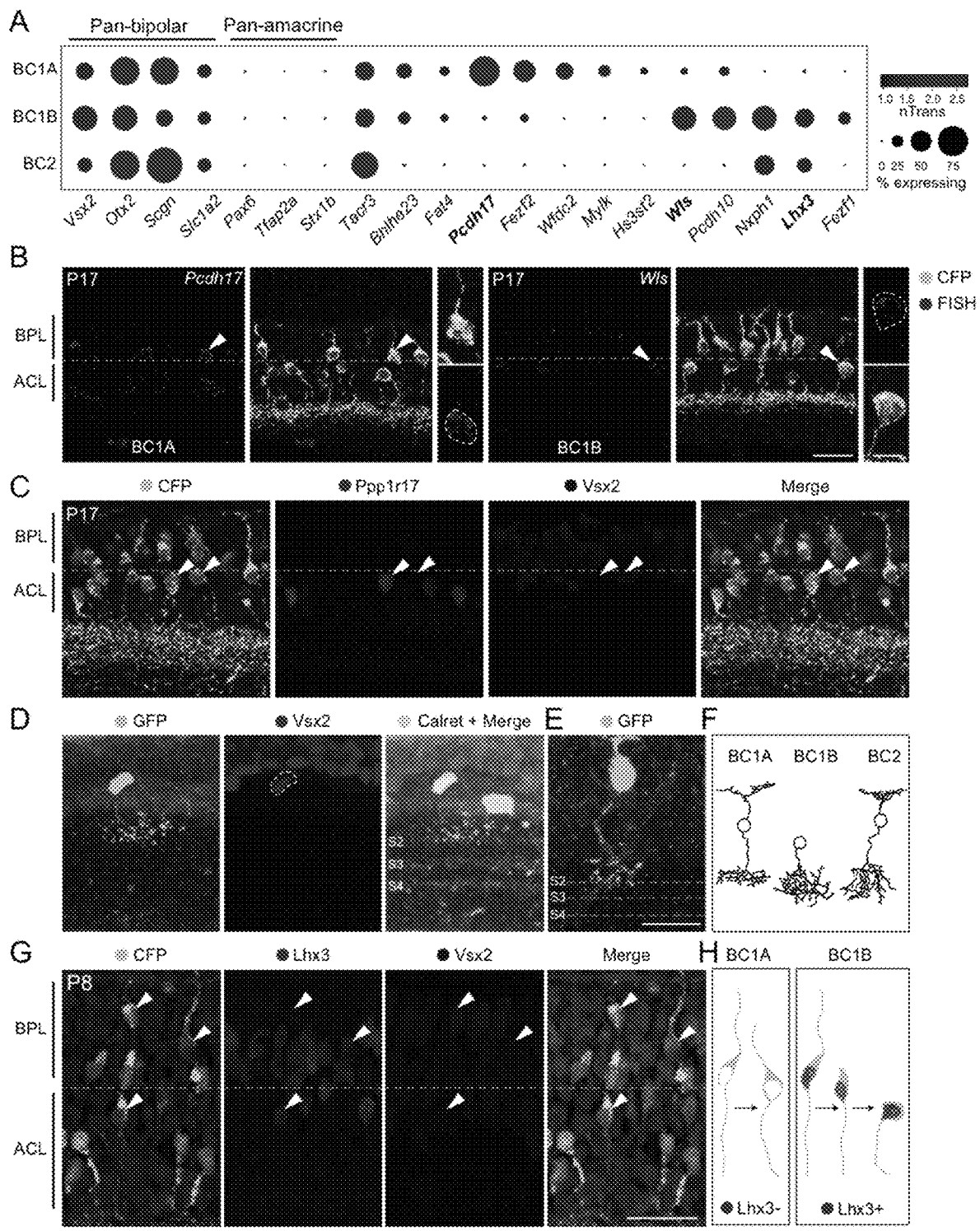
FIG. 11 shows that BC1B is a non-canonical bipolar type. Panel A of FIG. 11 depicts expression patterns of known BC and amacrine cell genes across BC1A, BC1B, and BC2 clusters, plus new BC1A and BC1B markers. Representation as shown in FIG. 6. Panel B of FIG. 11 shows that Pcdh17 (BC1A marker) and Wls (BC1B marker) label distinct populations of CFP positive cells in the MitoP line. Pcdh17 labels cells with a bipolar morphology positioned in the bipolar cell layer (BCL), whereas Wls labels cells that lack an upward process and are positioned in the amacrine cell layer (ACL) (dashed grey line denotes the division between these two layers). Insets show example cells with or without an upward process. Panel C of FIG. 11 depicts that BC1B cells (Vsx2+ Ppp1r17-) are distinct from nGnG amacrine cells (Vsx2- Ppp1r17+). Panels D-E of FIG. 11 refer to lentiviral labeling and Vsx2 immunostaining showing that BC1B cells lack an upward process and laminate in S1 (Panel D of FIG. 11), in contrast to other bipolar types that laminate at a similar depth in the IPL (Panel E of FIG. 11). Panel F of FIG. 11 depicts representative drawings based on EM reconstructions of BC1A, BC2, and BC1B (the latter identified post-hoc from (Helmstaedter et al., 2013)). Panels G-H of FIG. 11—show that BC1B cells lose their apical process, and translocate to the ACL (Panel G of FIG. 11). Both BC1A (Lhx3- Vsx2+) and BC1B (Lhx3+ Vsx2+) have a bipolar morphology at P8. See intermediate cell in the ACL in Panel G of FIG. 11 and diagram of developmental events in Panel H of FIG. 11. Scale bars indicate 20 µm for main panels and 10 µm for insets.

The present disclosure describes previously un-described BC types, identifies relationships among types, and associates these relationships with regulatory factors and key functional molecules. The identification of BC1B illustrates the power of scRNA-seq. BC1B cells appeared amacrine-like in morphology and position. Indeed, it seems likely that these features impeded their previous detection. However, molecular classification shows BC1B to be grouped with bipolar cells in adulthood, and they display a typical bipolar morphology during development (FIG. 11). Such morphological transitions during development have precedents within the CNS. In the mammalian cortex, for example, some pyramidal neurons maintain their morphology, while others subsequently retract their apical dendrite and become spiny stellate neurons (Callaway and Borrell, 2011; Koester and O'Leary, 1992; Vercelli et al., 1992). The presence of a cell type with morphological features of more than one classically defined type, which can be assigned to multiple distinct neuronal classes using different metrics, raises the possibility that morphology based classification of other types in the CNS may be significantly revised with application of molecular profiling.

Figure 14:
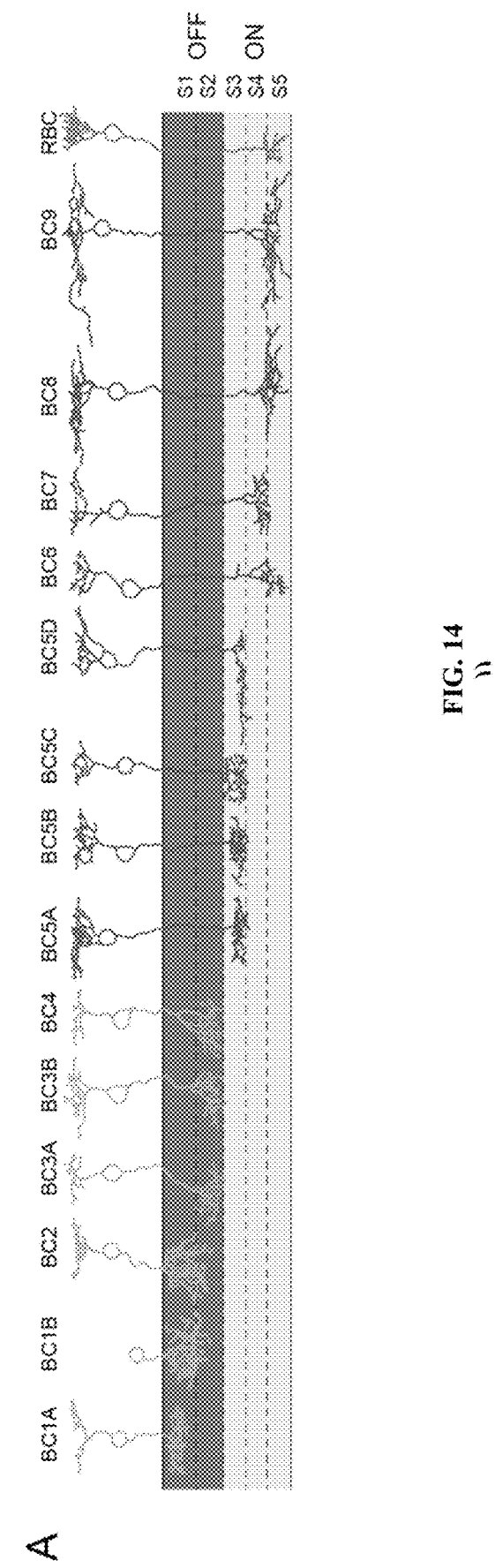
FIG. 14 depicts that drop-seq transcriptomes provide insights into BC function. Panel A of FIG. 14 shows representative drawings of BC types validated in this study, drawn from EM reconstructions (Helmstaedter et al., 2013). Panel B of FIG. 14 is a hierarchical clustering of BC clusters based on average expression levels of genes within each cluster, as shown in FIG. 7, now with identities of the BC1s, BC5s, and BC8 and 9 resolved based on results from FIG. 11, Panels A-L of FIGS. 12, and 13, respectively. Panel C of FIG. 14 shows enrichment patterns of Gene Ontology (GO) categories in BC clusters based on the GO-PCA algorithm. Rows correspond to significantly enriched GO terms, while columns correspond to random averages of single-cell gene expression signatures arranged by cluster (200 per cluster, averaging was performed to mitigate single-cell noise). Panels D-H of FIG. 14—are dotplots of functionally and developmentally relevant genes expressed by BC types. Representation as shown in FIG. 6. Panel D of FIG. 14 shows glutamate receptors and ON pathway components. Panel E of FIG. 14 depicts acetylcholine, GABA, and glycine receptors. Panel F of FIG. 14F shows potassium channel subunits. Panel G of FIG. 14 depicts transcription factors. Panel H of FIG. 14 shows adhesion/recognition molecules. In panels of Panels D-H of FIG. 14, only genes expressed in >20% of cells in at least one BC cluster are shown.
Figure 14:
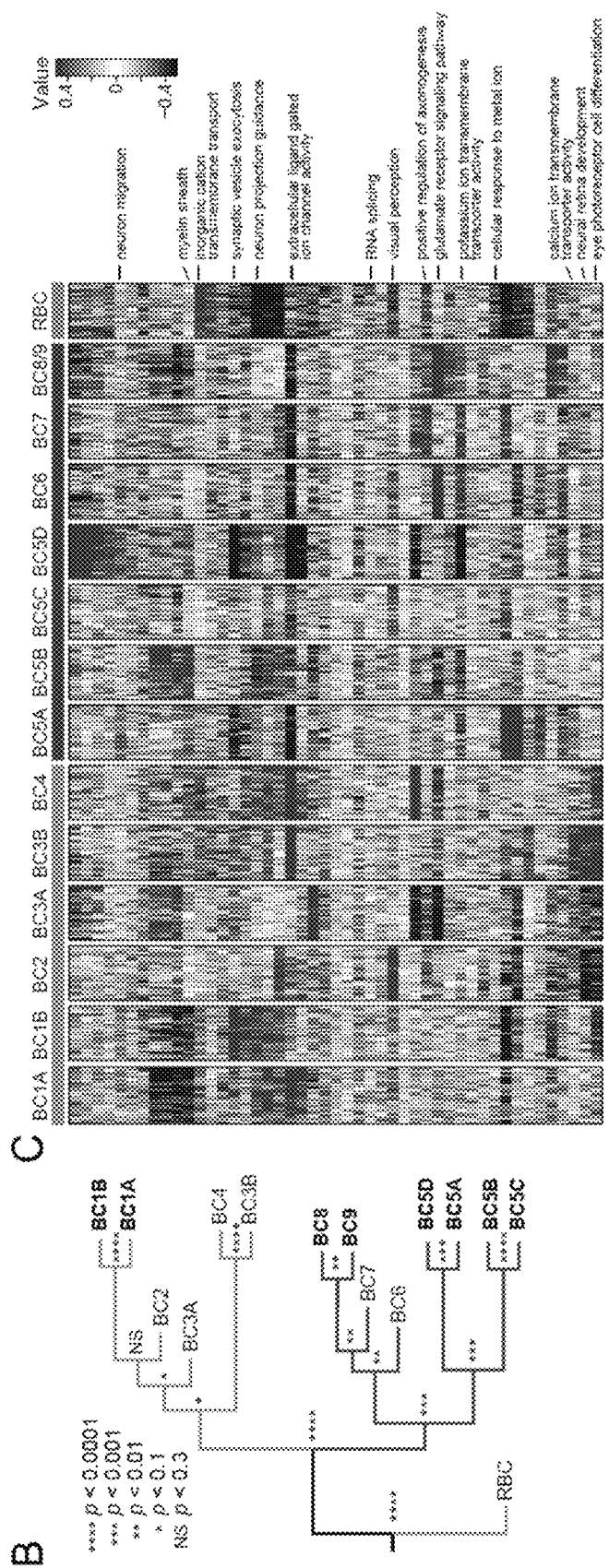
Figure 14:
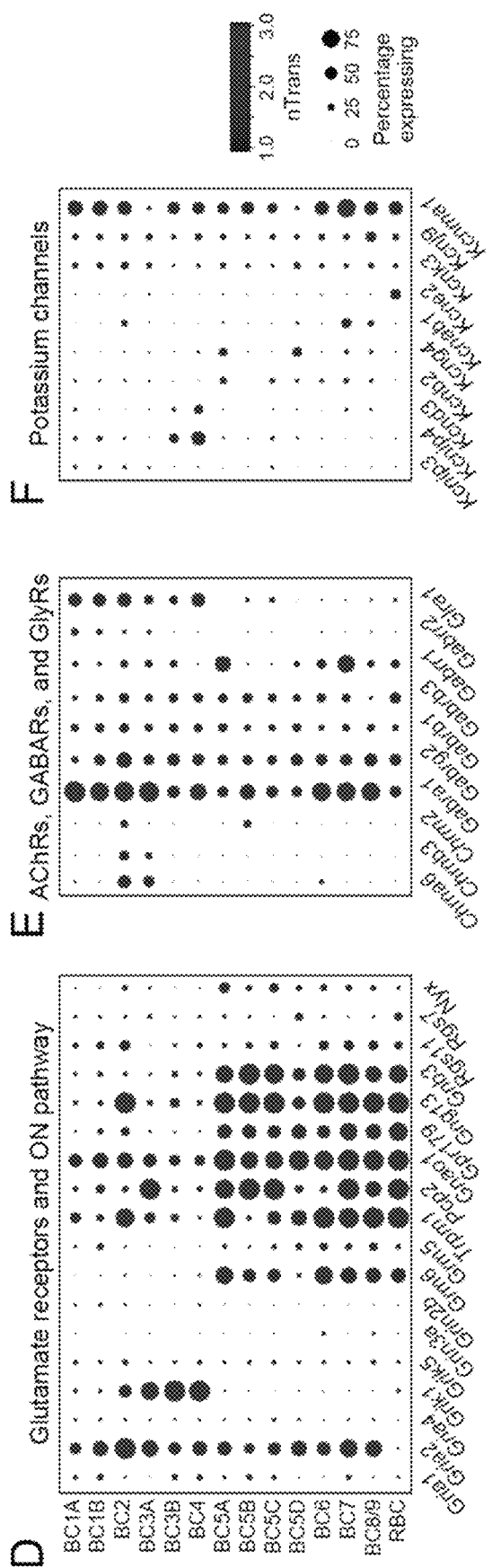
Figure 14:
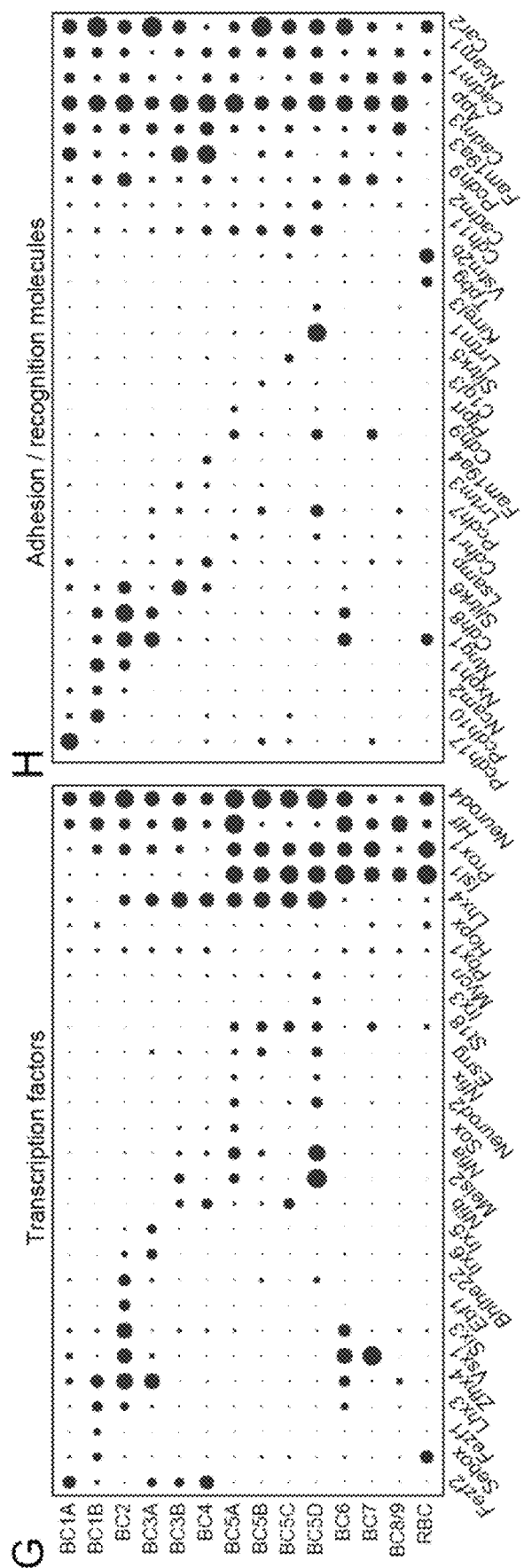

Hierarchical clustering of cell types for example BC types based on transcriptional profiles provides insight into the relationships among the cell types such as BCs. For example, the two main distinctions among BC types are rod vs. cone BCs and ON vs. OFF BCs. The ON-OFF distinction is associated with the signaling mechanism in dendrites (metabotropic vs ionotropic; Panel D of FIG. 14) and the level of axonal stratification (OFF in the upper strata and ON in the lower strata of the IPL). The rod-cone distinction is associated with synaptic input—predominantly (though not entirely) from rod vs. cone photoreceptors (Haverkamp et al., 2008; Mataruga et al., 2007; Pang et al., 2010). The first split in the cell type dendrogram (Panel B of FIG. 14) separates the rod from cone BCs, with a second split separating ON cone from OFF cone BCs. Thus, ON cone BCs are more similar to OFF cone BCs than to rod BCs, which are an ON type. This distinction might reflect a proposed late evolutionary addition of RBCs to the bipolar cell class (Cepko, 2014). Grouping of cone BC clusters shows lamination depth in the IPL to be a good correlate of relatedness. Although BC5D uniquely shares a wide axonal arbor morphology with BC8 and 9, it does not show a close relatedness to these types. Rather, the four clusters with cells laminating between S3 and S4, BC5A-D, were grouped together despite their varied arbor morphologies (Panel A of FIG. 14 and Panel B of FIG. 14). Likewise, BC6-9, which laminate lower in the IPL, were positioned together in the dendrogram. Within the BC5 group, BC5A and D are most closely related, and we now show that three transgenic lines previously reported to mark BC5 (Cdh9-lacZ, Kcng4-cre and Htr3a-GFP; (Duan et al., 2014; Haverkamp et al., 2009)) in fact label both BC5A and 5D, but not BC5B and 5C. One possible exception to this rule is BC2. Despite sharing lamination with BC1A and BC1B, BC2 did not cluster reliably with these types, instead displaying an unstable position, with only 70% of the bootstrap trials placing it in the OFF BC branch. In a large proportion of the other trials it was positioned in the ON branch next to BC6. Interestingly, BC2 expresses genes encoding components of the ON-type glutamate receptor signaling complex (Gng13, Nyx, and Trpm1) (Panel D of FIG. 14).

Figure 15:
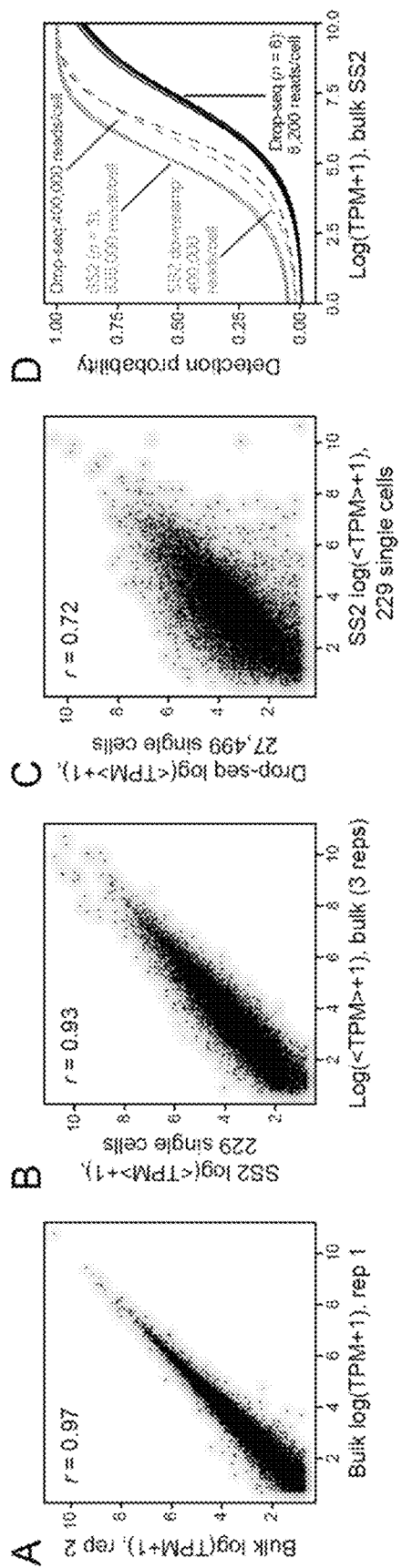
FIG. 15 depicts comparison of Drop-seq with Smart-seq2. Panel A of FIG. 15 shows bulk RNA-seq expression levels of 15,063 genes tightly correlate across two biological replicates (~10,000 cells each) processed using the Smart-seq2 method. Panel B of FIG. 15 shows gene expression levels averaged across 229 single cells (3 biological replicates) tightly correlate with the expression levels in the bulk libraries. Panel C of FIG. 15 shows single-cell averaged expression levels of Vsx2-GFP cells (log(Transcripts-per-million+1) units) correlate between Smart-seq2 and Drop-seq datasets. Panel D of FIG. 15 shows sensitivity of transcript detection in single cell libraries as a function of Smart-seq2 bulk expression levels. Curves show results for Smart-seq2 (3 replicates), Drop-seq (6 replicates) and deep-sequenced Drop-seq and downsampled Smart-seq2 data. Panel E of FIG. 15 is a clustering and tSNE visualization of Smart-seq2 single-cell data. Each cell is represented on the tSNE map by its random forest (RF) assigned cell type label. The RF model assigned one of 18 possible types including 14 BC types (1A-8/9), RBC, Müller glia (MG), Amacrine cells (A), rod photoreceptors (R), cone photoreceptors (C). Cells that could not be unambiguously assigned to one of these classes are labeled as "N". Panel F of FIG. 15 shows top 30 differentially expressed genes in each BC type computed using a post-hoc test on the Smart-seq2 data based on the RF-assigned labels. BC types with fewer than 3 cells detected in the data were excluded. Black bars on the right side-bar indicate genes that were also found to be differentially expressed in the Drop-seq data. Panel G of FIG. 15 is a tSNE visualization of Kcng4-GFP Smart-seq2 data (309 single cells). Each cell is represented on the tSNE map by its RF-assigned class label. Panels H-I of FIG. 15 depict violin plots showing expression of known and novel BCSA-D markers (identified in Drop-seq) in the BCSA, BCSD and BC7 clusters.
Figure 15:
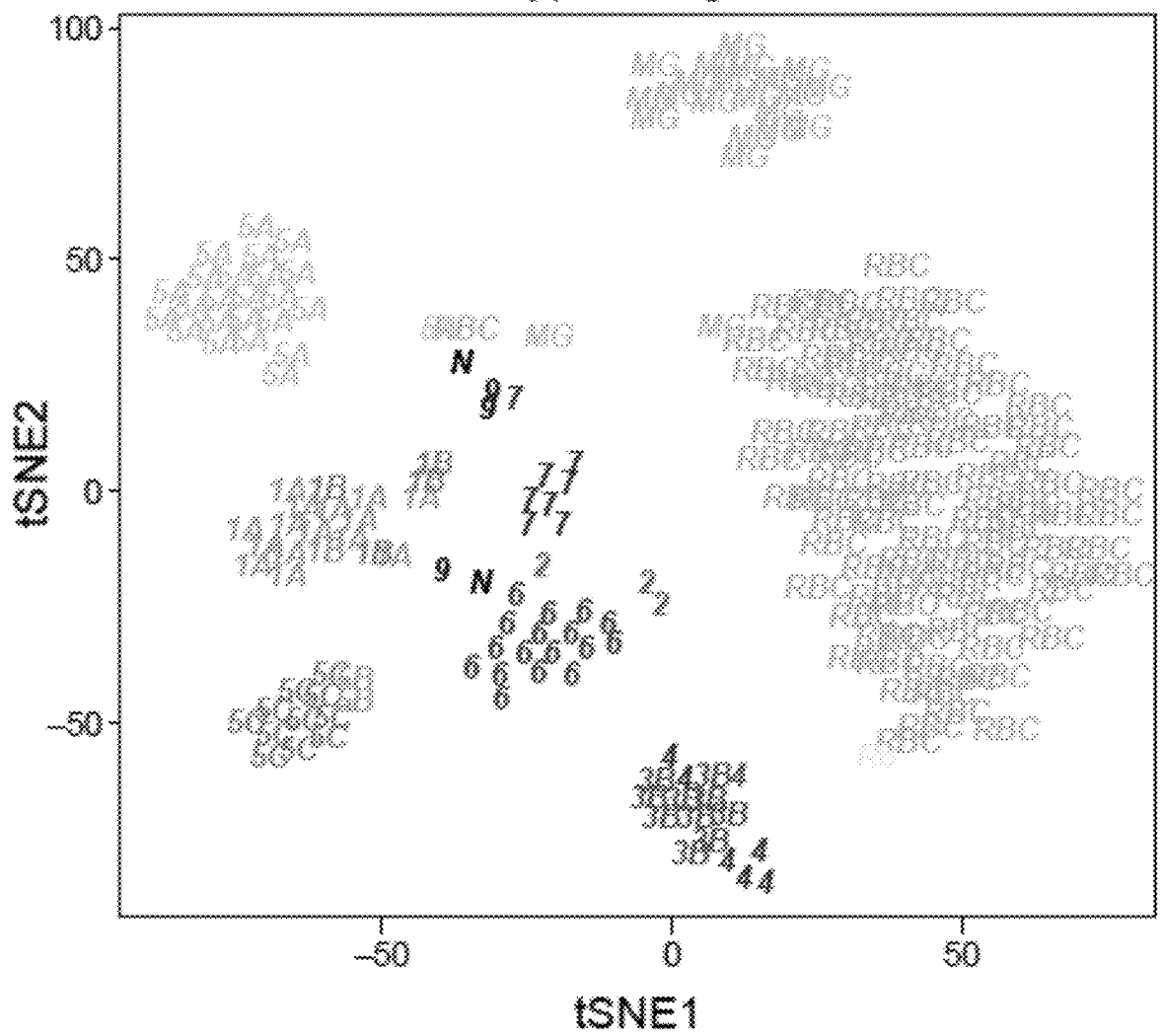
Figure 15:
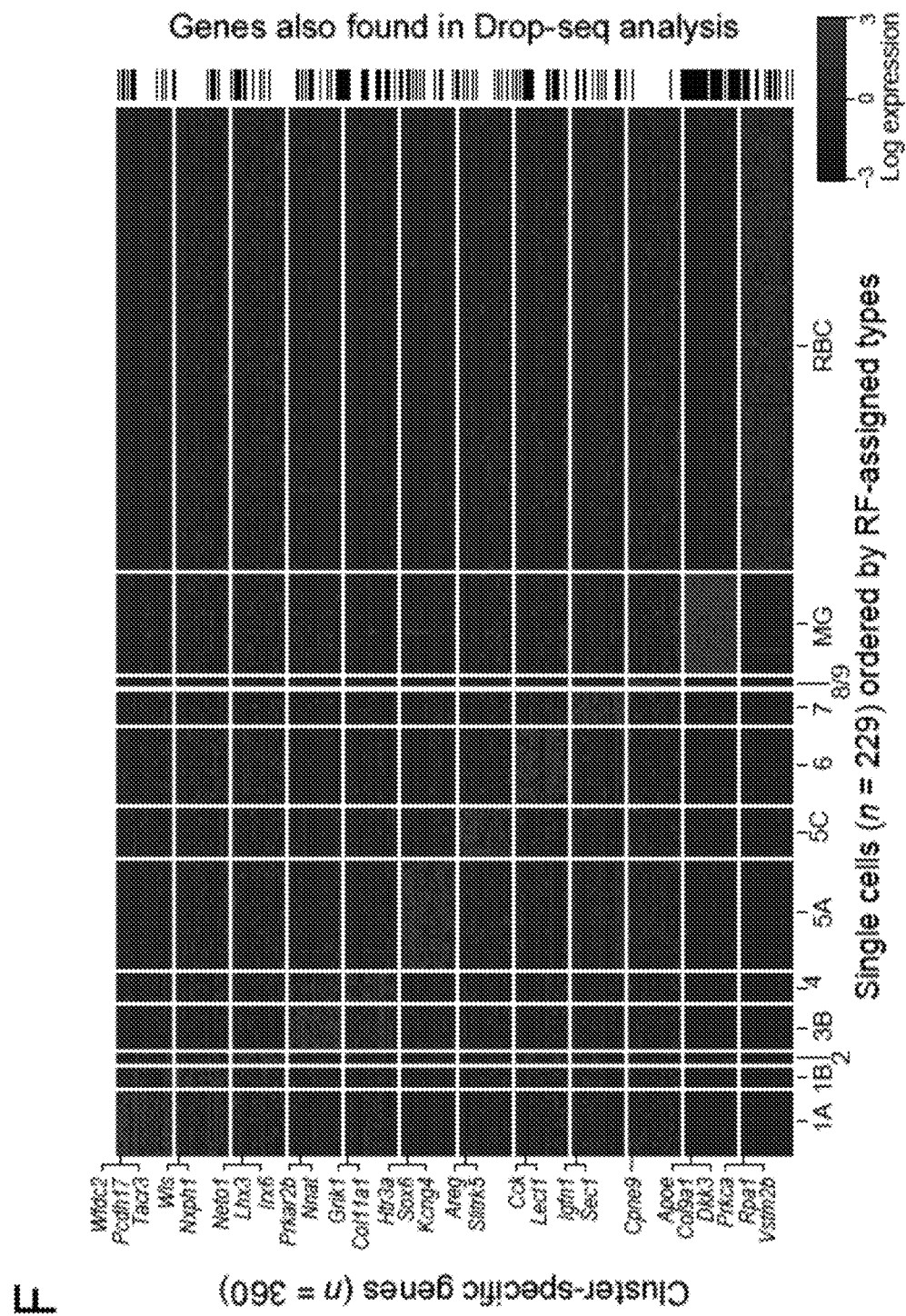
Figure 15:
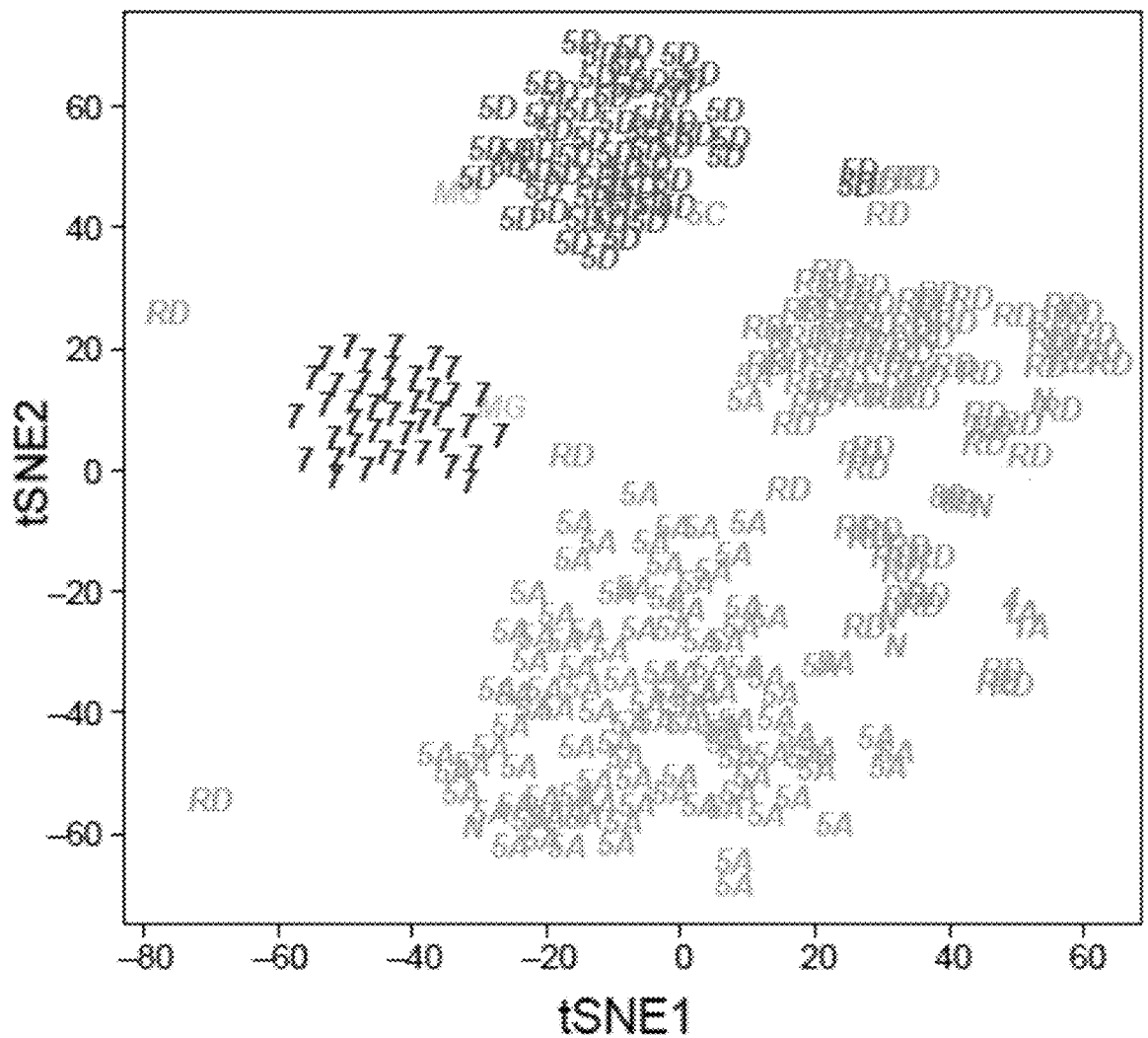
Figure 15:
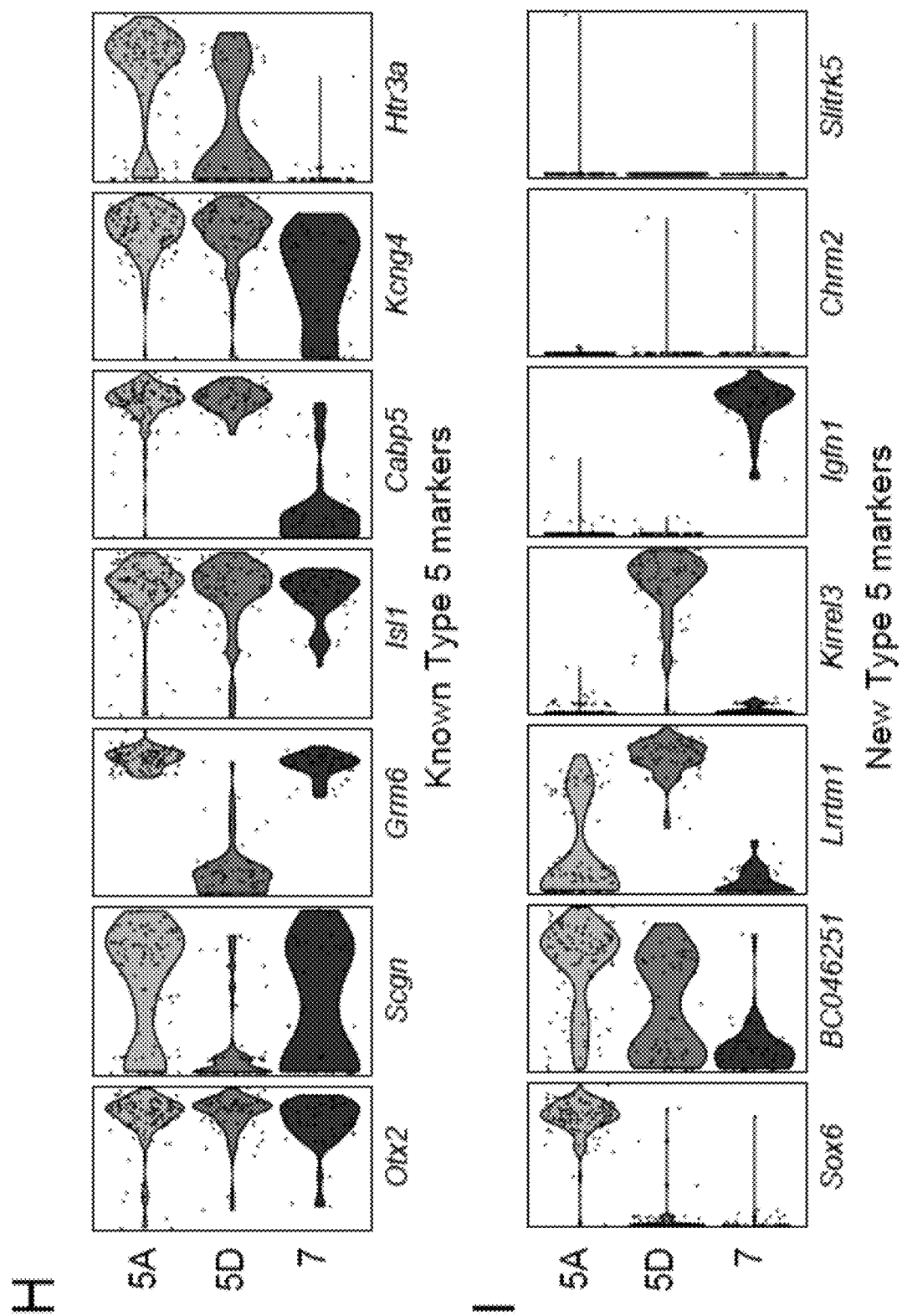

Each population of cells presents its own challenges and opportunities, but the present disclosure provides methods which can be adapted to the different needs. An attractive strategy is to first identify cell types using large numbers of cells profiled at shallow depth, and then, if desired, re-sequence a subset at higher coverage for a deeper analysis that is guided by a reliable classification (Panel D of FIG. 15). Nevertheless, even in those settings, relatively shallow sequencing, especially when combined with other attributes (Cadwell et al., 2016; Fuzik et al., 2016; Satija et al., 2015), may suffice to recover subtle signals, aided by the natural modularity of transcriptional programs.

The empirical analysis of downsampled (in cell number) Vsx2-GFP Drop-seq, full retina Drop-seq, and Smart-seq2 datasets (FIG. 15, FIG. 17 and FIG. 18) underscores the importance of large cell numbers for robust classification. BC types occurring at a frequency >200 cells in the Drop-seq datasets are resolved. Some non-BC types, like cone photoreceptors, were resolvable despite comprising <50 cells per cluster because of their transcriptional distinctiveness. This suggests that the minimum number of cells needed to resolve all cell types is a function of their frequency distribution, the extent of transcriptional differences among types (especially among rare types), and the depth of sequencing. In particular, comparison of Vsx2-GFP Drop-seq and Smart-seq2 data shows that deeper sequencing does not enable better classification when cell numbers are low. For example, BC3B and BC4 could not be resolved from each other in Smart-seq2 data (100× higher depth per cell, 120× fewer cells than Drop-seq) even though their proportions were higher in the Smartseq2 dataset (4.4%, 3%) than in Drop-seq (2.9%, 1.4%). The computational challenges separating the two rarest BC types, BC8 and BC9, in the Drop-seq data at various cell downsampling levels further underscores the need for large cell numbers in classifying rare, related types.

The advance of multiplexing technologies and decreasing sequencing costs allows profiling of larger numbers of cells at greater depth. Analysis of such datasets requires the development of scalable computational methods.

Deriving neuronal taxonomies from transcriptional profiling of single cells requires scalable validation methods. Prior to this work, BCs had been predominantly characterized morphologically, using the tiling of axonal arbors to define single cell types. The present disclosure employs detection by in situ hybridization in retinal whole mounts or combined with morphological labeling in section as a generalized method to assign gene expression to individual neuronal types. mRNA detection provides a direct readout of the transcriptome and is highly scalable, in contrast to antibodies and transgenic lines, whose low success rates and high costs are not tenable for large scale validation.

The invention is further described in the following examples, which do not limit the scope of the invention described in the claims.

EXAMPLES

Example 1: FACS Enrichment and Drop-Seq of Single Retinal Bipolar Neurons

Figure 2:
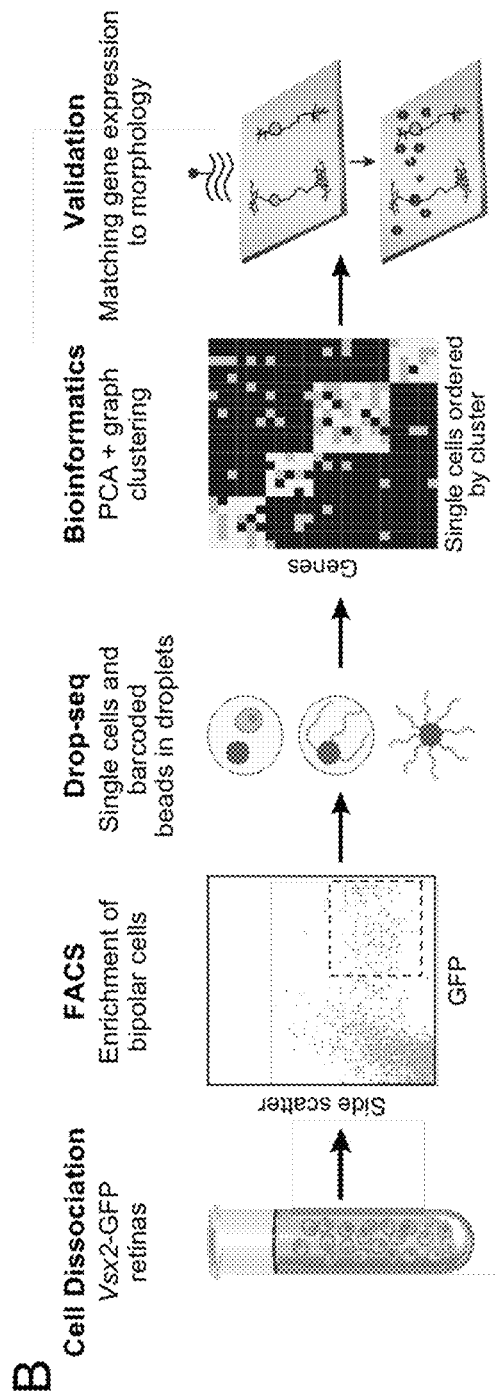

BCs comprise about 7% of all retinal cells in mice (Jeon et al., 1998; Young, 1985). To obtain an enriched population for molecular profiling, a transgenic line that expresses GFP in all BCs as well as in Müller glia (Vsx2-GFP) was used (Rowan and Cepko, 2004). Retinas were dissociated at postnatal day 17 (P17) and GFP-positive cells were collected by fluorescence activated cell sorting (FACS) (FIG. 2). scRNA-seq libraries were prepared using Drop-seq, wherein single cells are paired in droplets with single microparticle beads coated with oligonucleotides for reverse transcription (Macosko et al., 2015). These oligonucleotides contain a bead-specific barcode ("cell barcode") uniquely identifying each bead (cell), and a unique molecular identifier (UMI) uniquely identifying each primer; the latter, allows "amplification duplicates" to be recognized and thereby facilitates digital counting of individual transcripts. Thousands of beads can be pooled prior to reverse transcription, PCR-amplification and library preparation, dramatically reducing labor and reagent costs (Macosko et al., 2015). Data were obtained from a total of 45,000 cells collected in two independent experiments, and sequenced to a median depth of 8,200 mapped reads per cell (Panels A-H of FIG. 16). To quantify gene expression, sequencing reads were aligned to a reference transcriptome after excluding low quality reads. Then the cell barcodes and UMIs were used to group sequencing reads by their cell-of-origin and to digitally count transcripts, respectively. Only those genes were considered that were detected in at least 30 cells, and only those cells were considered in which >500 genes and >1,200 transcripts were detected (Panel A of FIG. 16), yielding a digital expression matrix of 13,166 genes across 27,499 cells.

Figure 3:
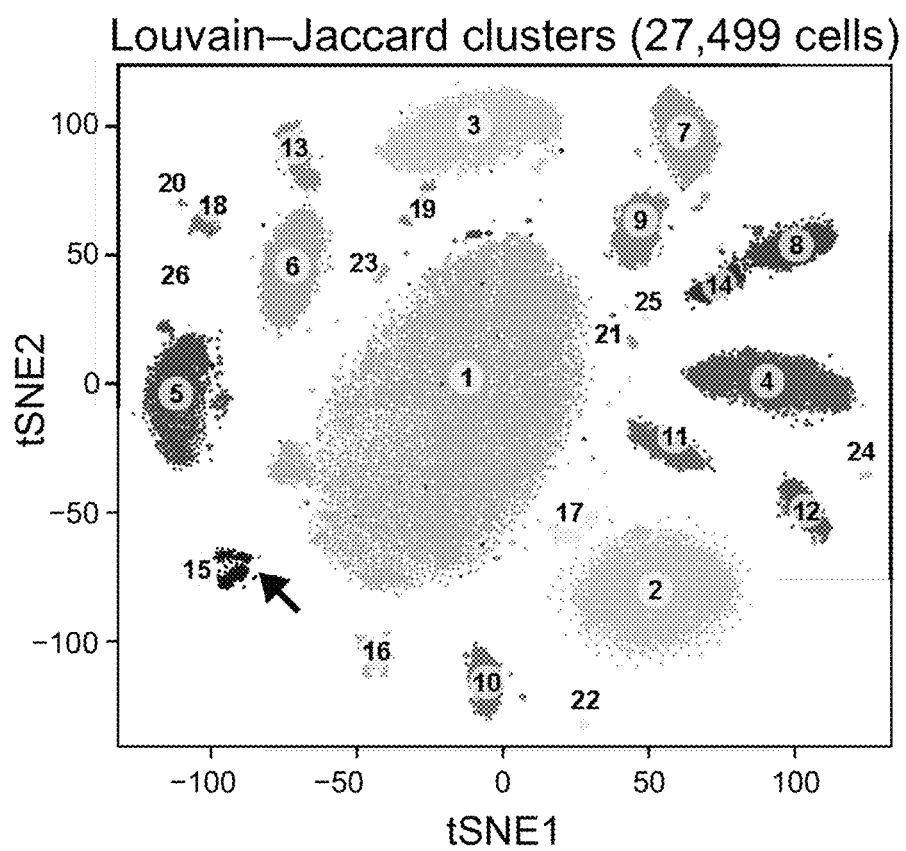
Figure 4:
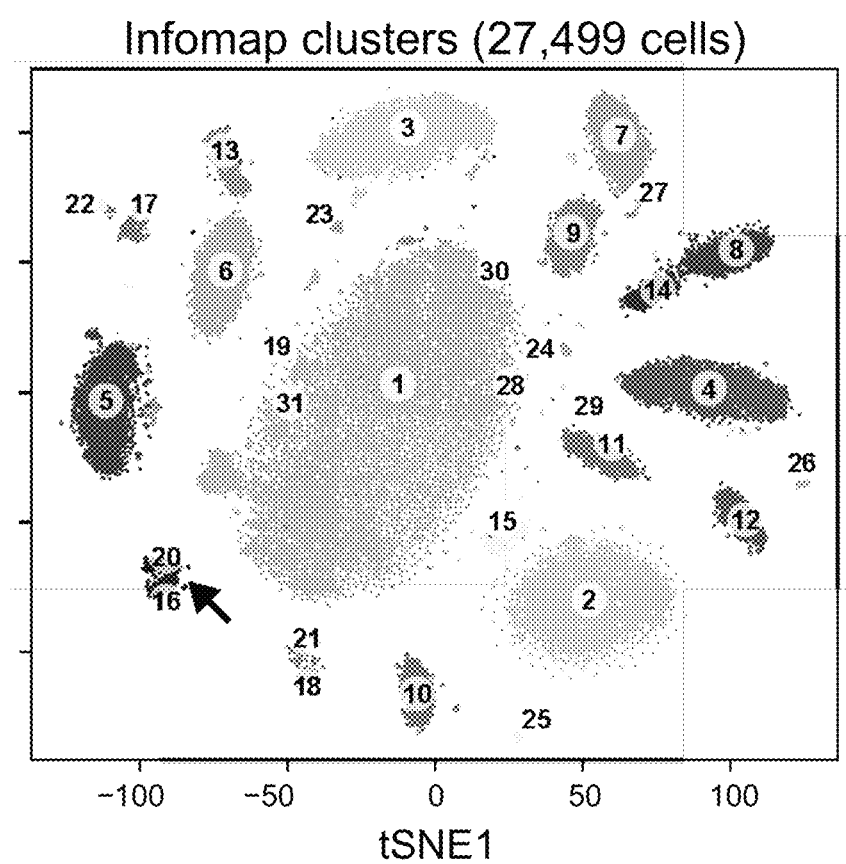
Figure 5:
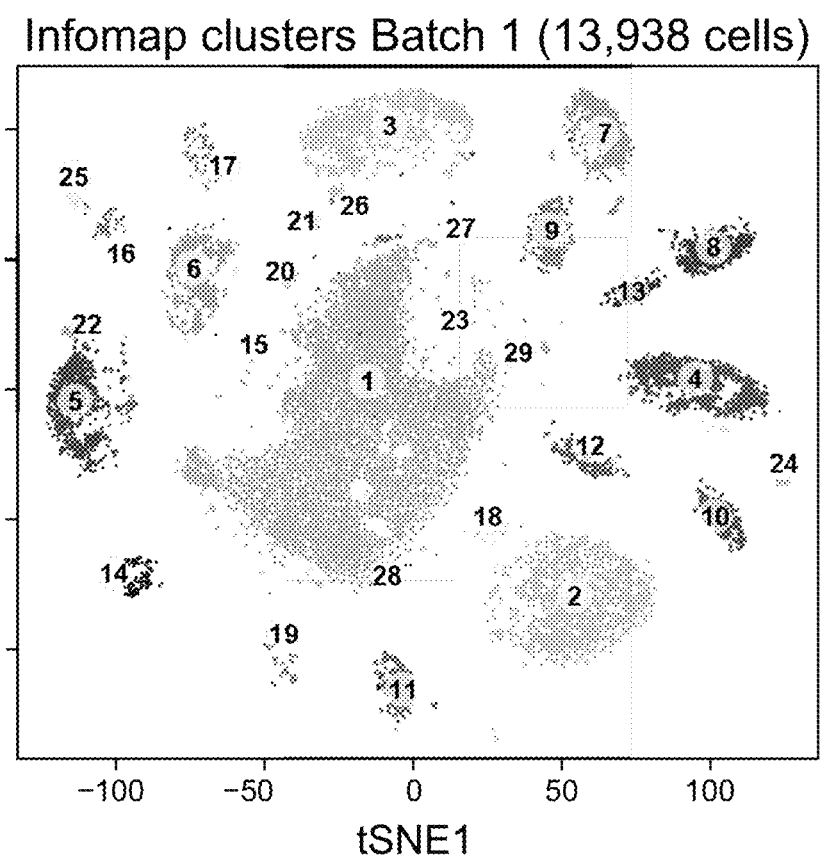
Figure 16:
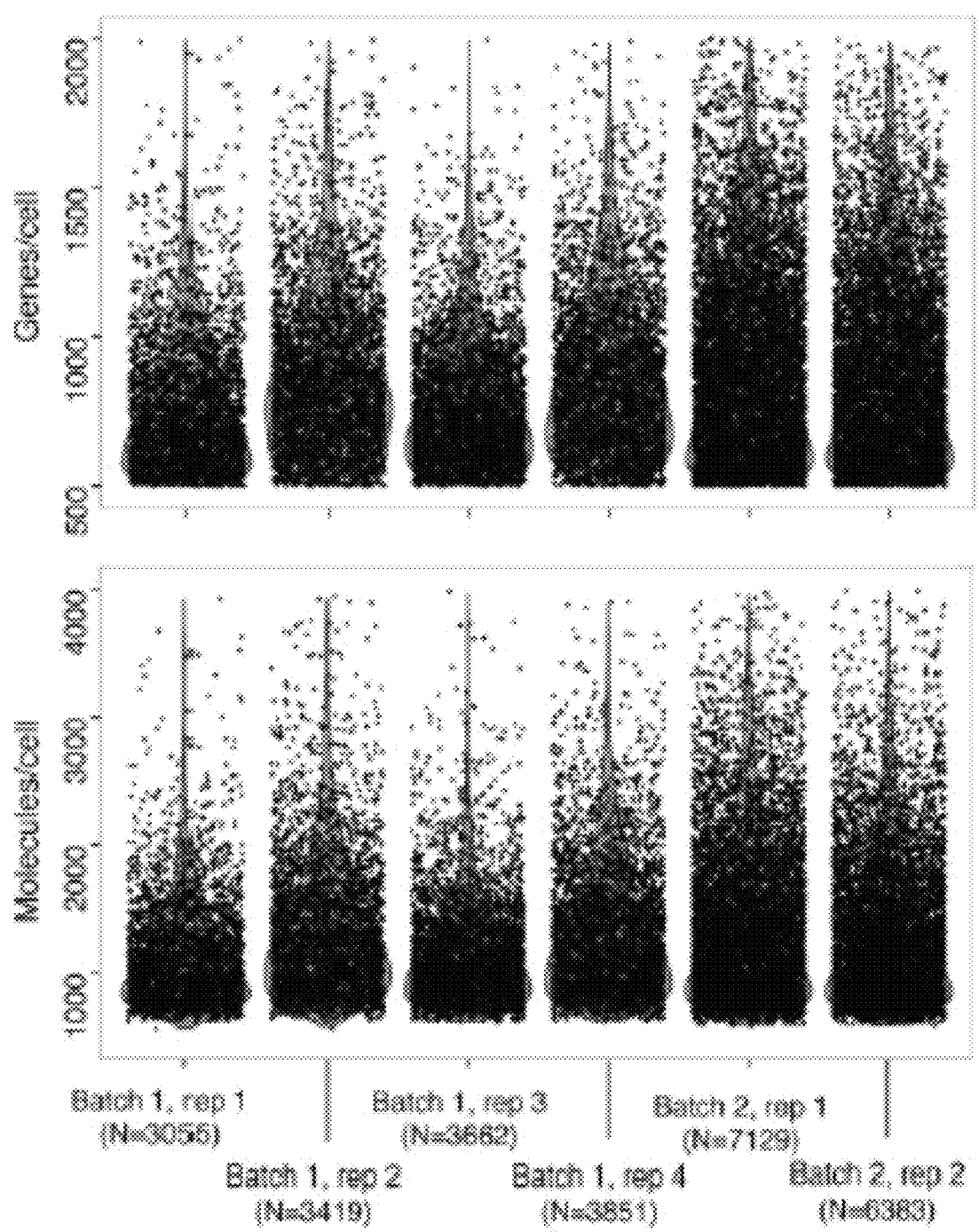
FIG. 16 shows library complexity metrics, correlation between replicates, PCA and tSNE, related to FIG. 1. Panel A of FIG. 16 depicts violin plots of genes/cell (upper) and transcripts/cell (lower) across the six experimental replicates. Only 27,994 cells filtered based on QC criteria are included (individual points). Panel B of FIG. 16 is a histogram of the ratio of the number of observed reads and the number of observed UMIs for the nonzero entries of the digital expression matrix (DGE). Dashed read line shows the median value. Both axes are represented in logarithmic units. Panel C of FIG. 16 is a histogram of the values of non-zero transcript counts observed in the DGE. Y-axis is represented in logarithmic units. Panel D of FIG. 16 is a scatter plot of gene expression values before batch correction (Eij units) between two cells randomly chosen from Batch 1 replicate 1. Each dot corresponds to a gene, and many genes have similar values because of the digital nature of the data. Panel E of FIG. 16 is a scatter plot of average gene expression values (across cells) between replicate 1 and replicate 4 of Batch 1 (Panel F of FIG. 16). Panel E of FIG. 16 shows same for replicate 1 and replicate 2 of Batch 2. Panel G of FIG. 16 shows same as Panel E of FIG. 16 for Batch 1, replicate 1 and Bach 2, replicate 1. Representative genes that are differentially expressed are indicated. Panel H of FIG. 16 is a sample-sample correlation (Pearson) of cell-average gene expression values (Eij, upper triangular), and of non-normalized cell-average transcript counts (lower triangular), before batch correction. For panels Panels E-H of FIG. 16, average expression values for every gene within a sample were computed by first averaging the normalized transcript counts Mij across all the cells, adding 1 and then taking the logarithm. Only 13,166 significantly expressed genes were considered. Panel I of FIG. 16 depicts scatter plots of PCA-scores for PC1-PC2, PC3-PC4 and PC9-PC10. Each dot corresponds to a single cell, and is colored based on its sample of origin (legend). Panel J of FIG. 16 shows a PCA-eigenvalue spectrum computed using the real expression matrix (upper) and randomized (n=500) expression matrices (lower). The theoretical spectrum based on the Marchenko-Pastur (MP) law is shown in red in the lower panel. The empirically observed (rand) and the predicted (MP) maximum and minimum eigenvalues $\lambda+$ and $\lambda-$ for the randomized data are indicated. Eigenvalues that are larger than the empirical-bound are indicated with red arrows (upper). Panel K of FIG. 16 is a 2D visualization of single cell variation using t-distributed stochastic neighbor embedding (tSNE), computed based on cell scores along 37 significant PCs. Single cells are colored based on their sample of origin and the scheme is the same as in the panel of Panel I of FIG. 16.
Figure 16:
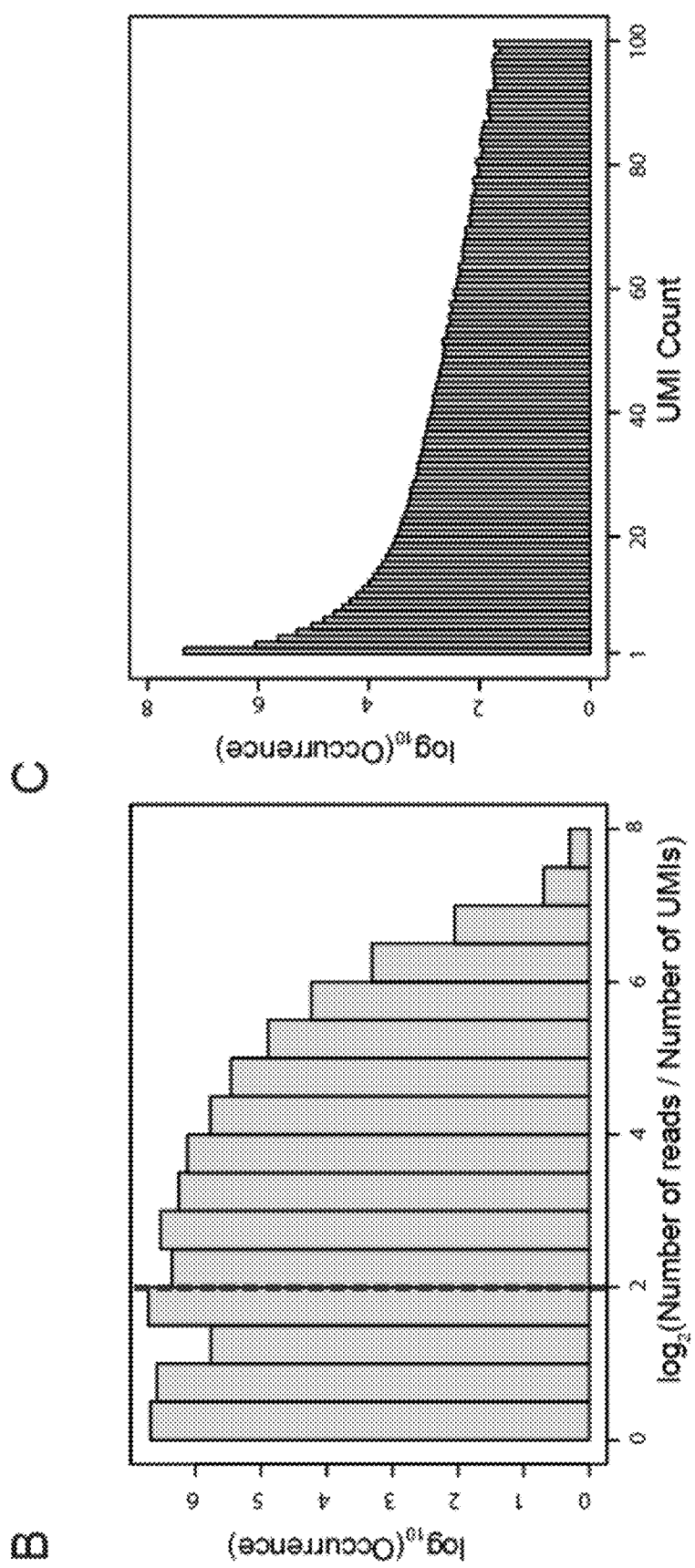
Figure 16:
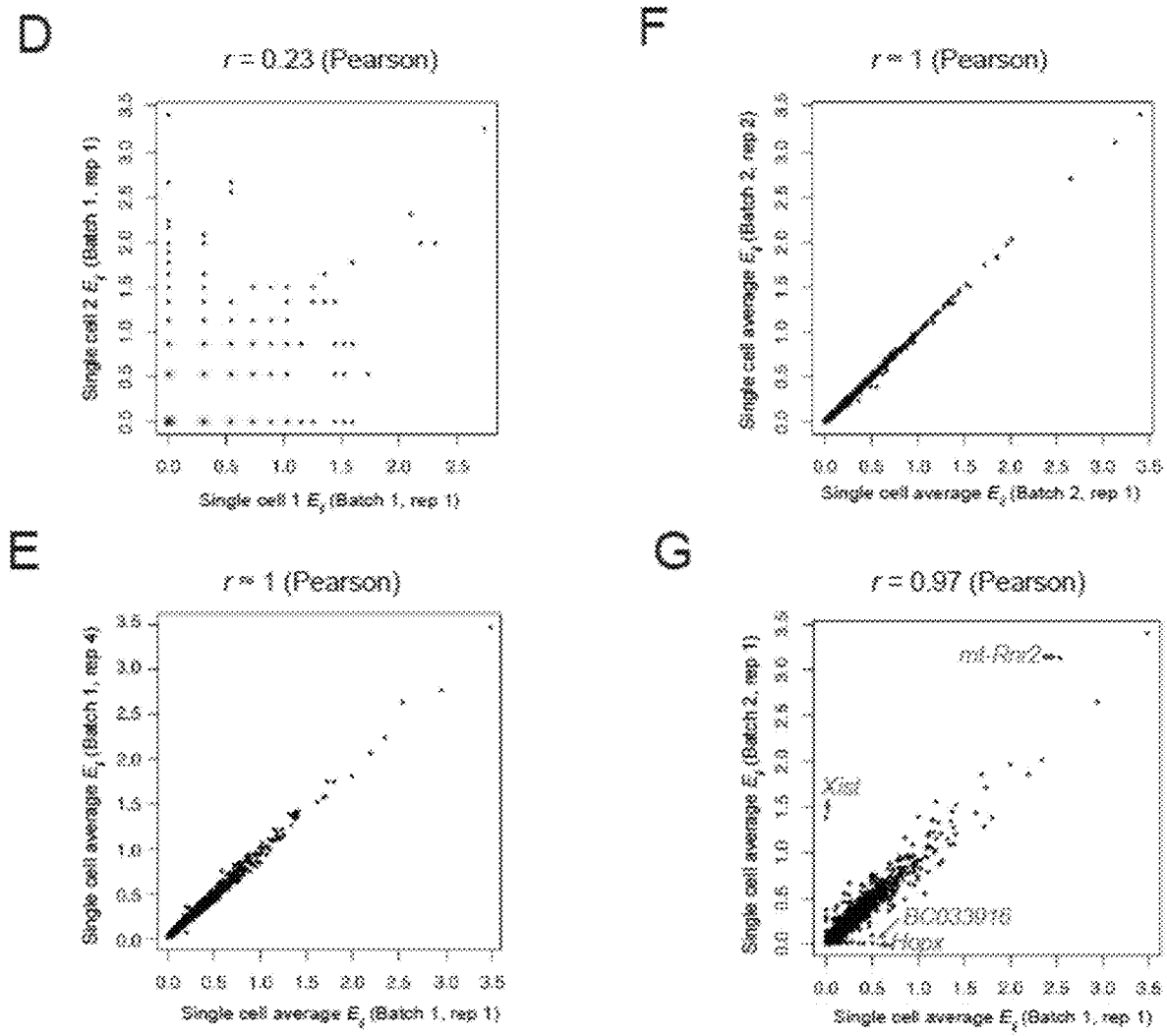
Figure 16:
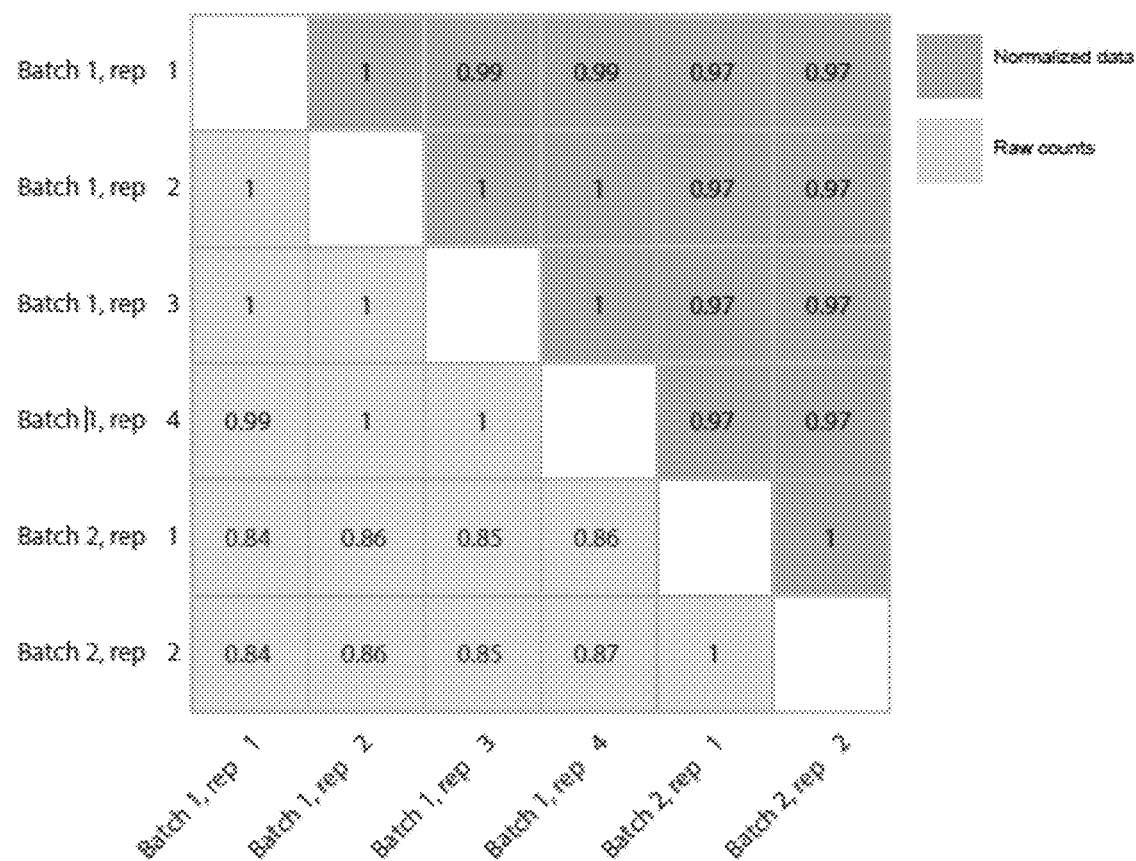
Figure 16:
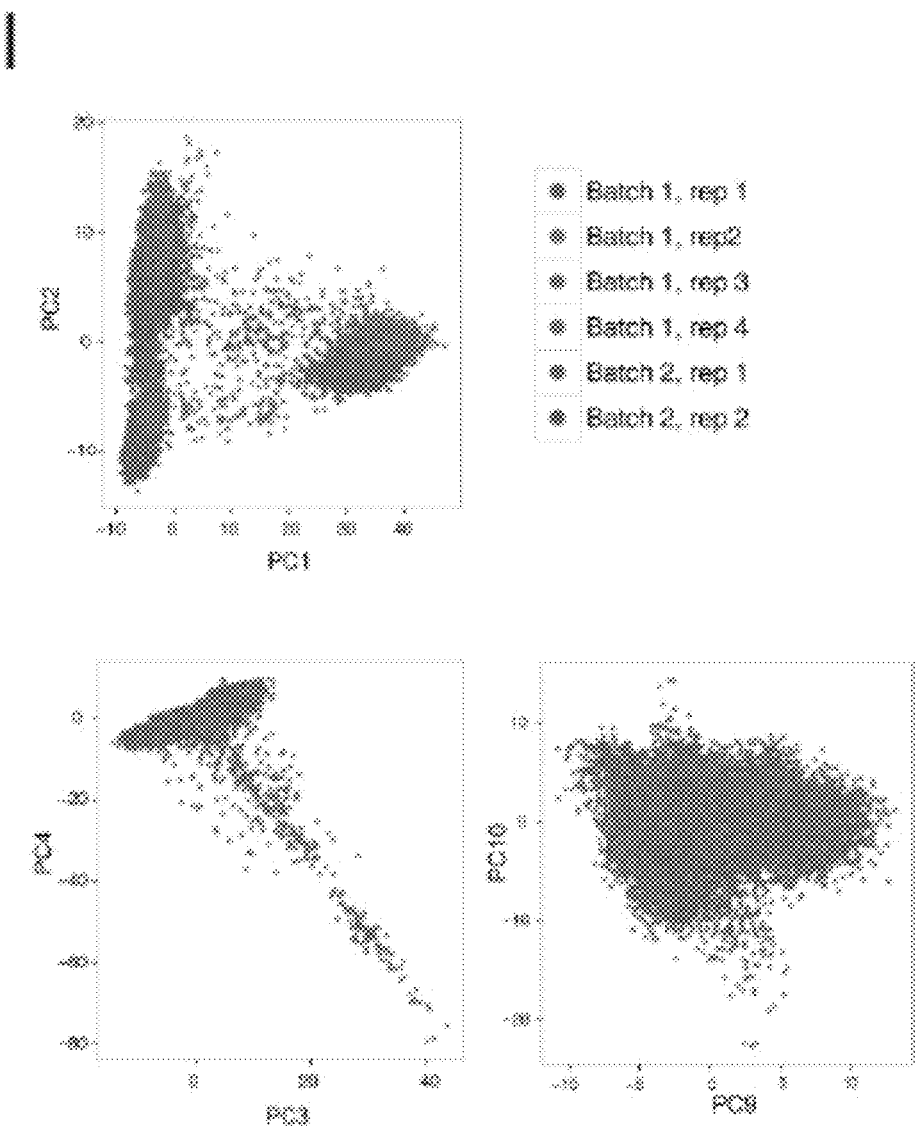
Figure 16:
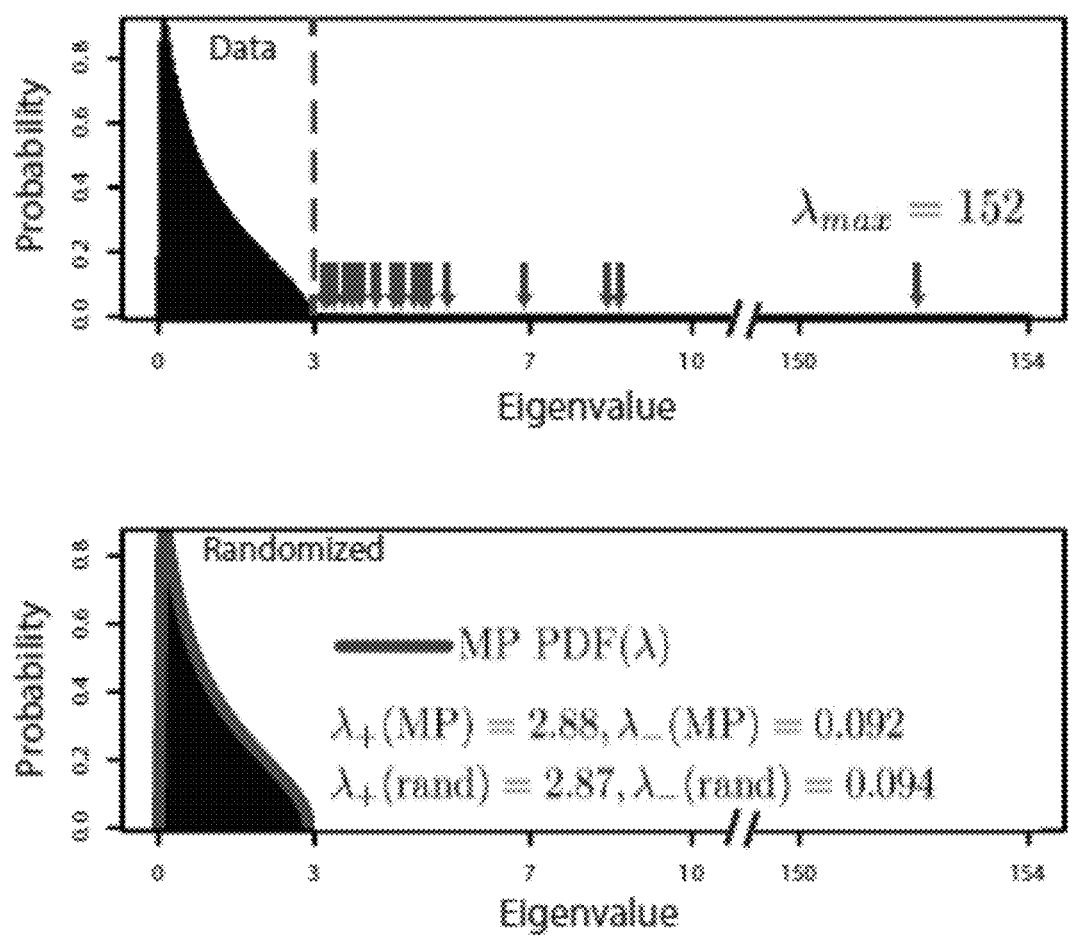
Figure 16:
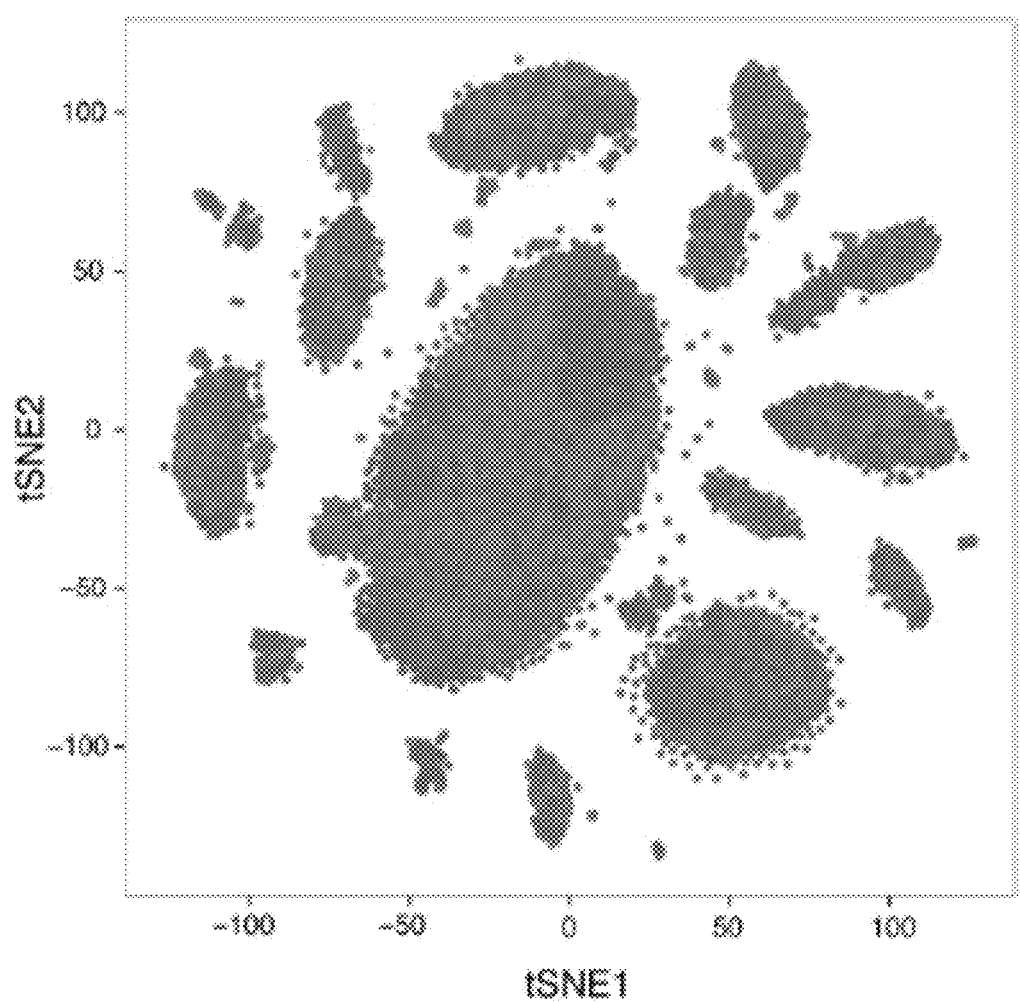

After correcting for batch effects, principal component (PC) analysis was applied, the 37 statistically significant PC scores based on data randomizations (empirical p value<10-3, Panels I and J of FIG. 16) were retained, and the cells were visualized in two dimensions using t-distributed stochastic neighborhood embedding (t-SNE; e.g., FIG. 3-FIG. 5, and Panel K of FIG. 16; (van der Maaten and Hinton, 2008); the 2D representation is used for visualization only).

All Drop-seq experiments were performed at postnatal day (P)17 on GFP+ cells FACS sorted from Tg(Chx10-

EGFP/cre,-ALPP)2C1c transgenic mice (Vsx2-GFP hereafter) bred for two generations to CD1 mice (Charles River) (Rowan and Cepko, 2004). Ten other transgenic strains with cell type-specific reporter expression, along with cre-dependent reporter lines, were used for Smart-seq2 and in vivo validation.

Example 2: Single Cell RNA-Seq

Retinas from the Vsx2-GFP mice were dissected in Hank's balanced salt solution (HBSS) and promptly dissociated using an accelerated DNAse-free protocol (Siegert et al., 2012) with minor modifications. GFP+ cells were collected using FACS. Drop-seq was performed largely as described previously (Macosko et al., 2015). A total of six replicates were prepared from two batches of Vsx2-GFP positive cells collected on different days. Paired-end sequence reads were processed largely as described before (Macosko et al., 2015) with an additional barcode correction step to account for oligonucleotide synthesis errors in the beads. After trimming of the SMART-adapter and polyA sequences, the right read was mapped to the mouse genome (version m38) using STAR v2.4.0a (Dobin et al., 2013). The 12 bp cell barcode on the left read was used to infer the cell of origin of each read, and the 8 bp unique molecular identifier (UMI) on the same read was used to digitally count transcripts. This resulted in a digital gene expression matrix (genes×cells) of transcript counts that was used for clustering. For Smart-seq2 experiments, single cells from the Vsx2-GFP and Kcng4-cre; stop-YFP lines were collected using FACS into separate 96-well plates with 5 µl lysis buffer comprised of Buffer TCL (Qiagen 1031576) plus 1% 2-mercaptoethanol (Sigma 63689). Also about 10,000 cells were collected from each retina from the Vsx2-GFP mice into 350 µl lysis buffer to serve as population RNA-seq controls. Samples were immediately frozen at −80° C. Smart-seq2 followed the published protocol (Picelli et al., 2014) with minor modifications.

Figure 9:
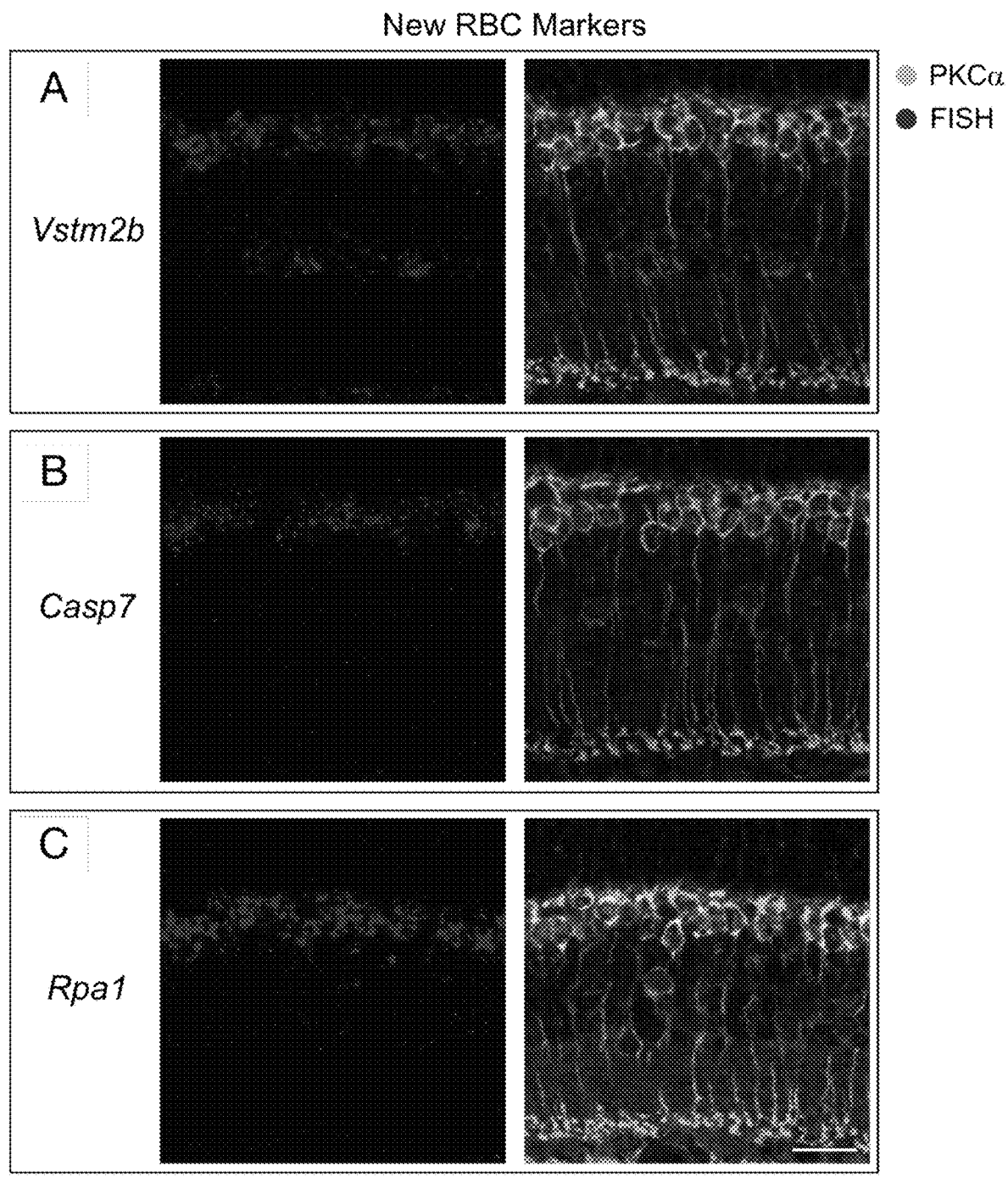
Figure 17:
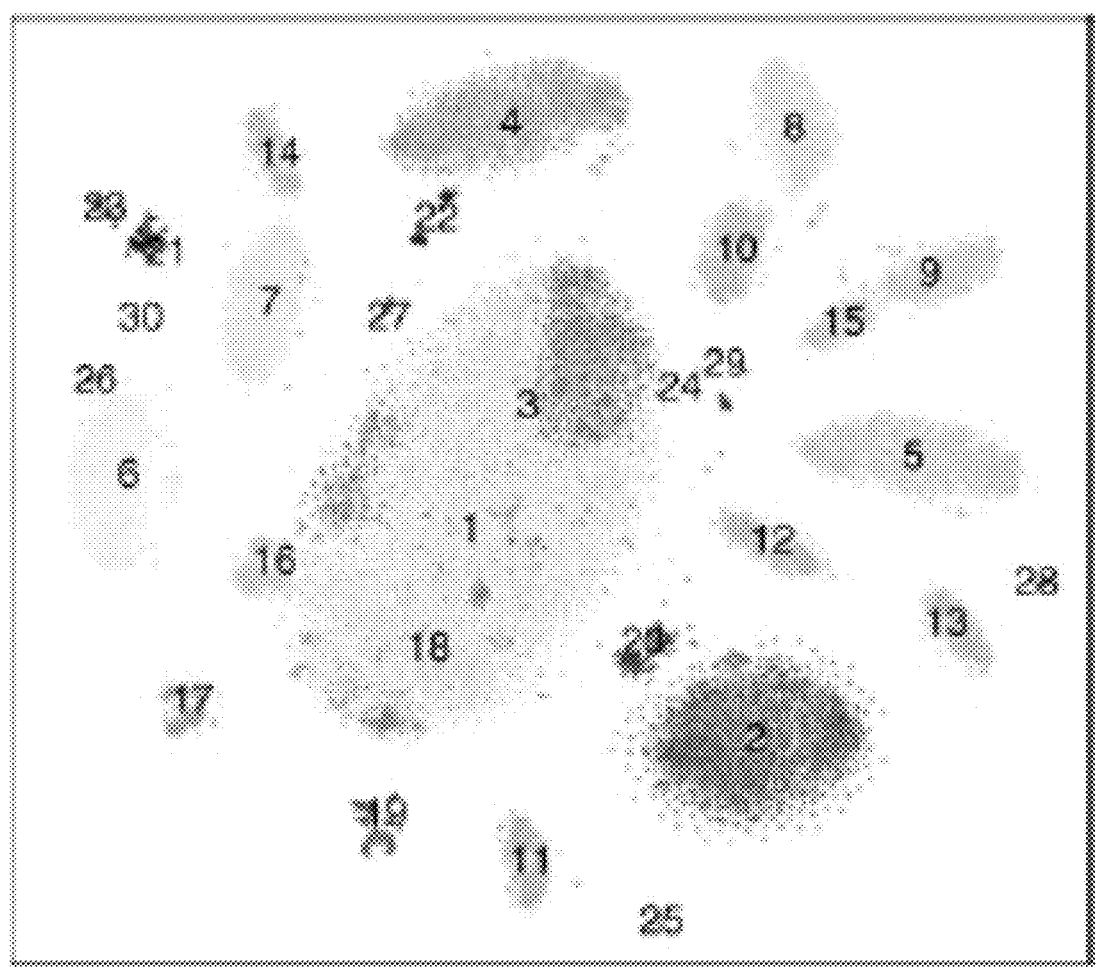
FIG. 17 shows bootstrap analysis of Louvain-Jaccard clusters, and comparison of six clustering methods, related to FIGS. 1-7. Panel A of FIG. 17 shows a clustering output of Louvain-Jaccard, prior to merging proximal clusters. Panel B of FIG. 17 depicts Stability$_k$ and Purity$_k$ scores for Louvain-Jaccard clusters in Panel A of FIG. 17. Panel C of FIG. 17 is a histogram of the number of differentially expressed genes FDR <0.01) found in all pairwise comparisons of clusters in panel A (N=2915 comparisons). In each pairwise comparison, only genes detected in at least 20% of cells in at least one of the two clusters, and exhibiting an effect size >2 were considered. The median number of differentially expressed genes (DE) in a pairwise comparison was 418 (dashed line). Inset shows that a small number of clusters have fewer than 50 DE genes. Panel D of FIG. 17 shows Louvain-Jaccard clusters, after iteratively merging clusters with fewer than 50 DE genes (henceforth referred to as the "post-merge"), identical to FIG. 3. Panel E of FIG. 17 depicts Louvain clusters based on an unweighted k-NN graph, post-merge. Panel F of FIG. 17 shows clustering output of Infomap, without merging. Panel G of FIG. 17 depicts Infomap clusters, post-merge, same as FIG. 4. Panel H of FIG. 17 shows post-merge Louvain-Jaccard clusters, based on significant PCs constructed using a subset of 2000 highly variable genes. Panel I of FIG. 17 shows k-means clustering in PCA space (k=30), without the merging step. Panel J of FIG. 17 depicts density clustering in tSNE space using DBSCAN using the parameters minPts=10, eps=1.8. No merging was performed. Panel K of FIG. 17 shows a Louvain-Jaccard procedure, postmerge, applied on 13,938 cells from Batch 1 (all 4 replicates). Panel L of FIG. 17 depicts an infomap procedure, post-merge, on the same dataset as Panel K of FIG. 17 same as FIG. 5. Panel M of FIG. 17 shows an output of BackSPIN on the same dataset as Panel K of FIG. 17. No merging was performed. Arrows indicate key differences compared to Panel K of FIG. 17 and Panel L of FIG. 17. Panel N of FIG. 17N depicts an infomap procedure, post-merge, applied on a randomly chosen subset of 5000 cells from Batch 1 (sampling across all 4 replicates). Panel O of FIG. 17 is an output of BackSPIN on 5000 cells used in the panel of Panel N of FIG. 17. No merging was performed. Arrows indicate key clusters that were resolved by Infomap/Louvain-Jaccard on the equivalent dataset (Panel N of FIG. 17) but are not resolved by BackSPIN. Panel P of FIG. 17 is an output of the clustering step RaceID on 5000 cells used in panel N. No merging was performed. In the panels of Panel A of FIG. 17 and Panels D-P of FIG. 17, the output of various clustering methods is visualized on the tSNE map shown in FIG. 3 and Panel K of FIG. 16. In the panels of Panels K-P of FIG. 17 only cells represented in the downsampled dataset are shown on the tSNE map.
Figure 17:
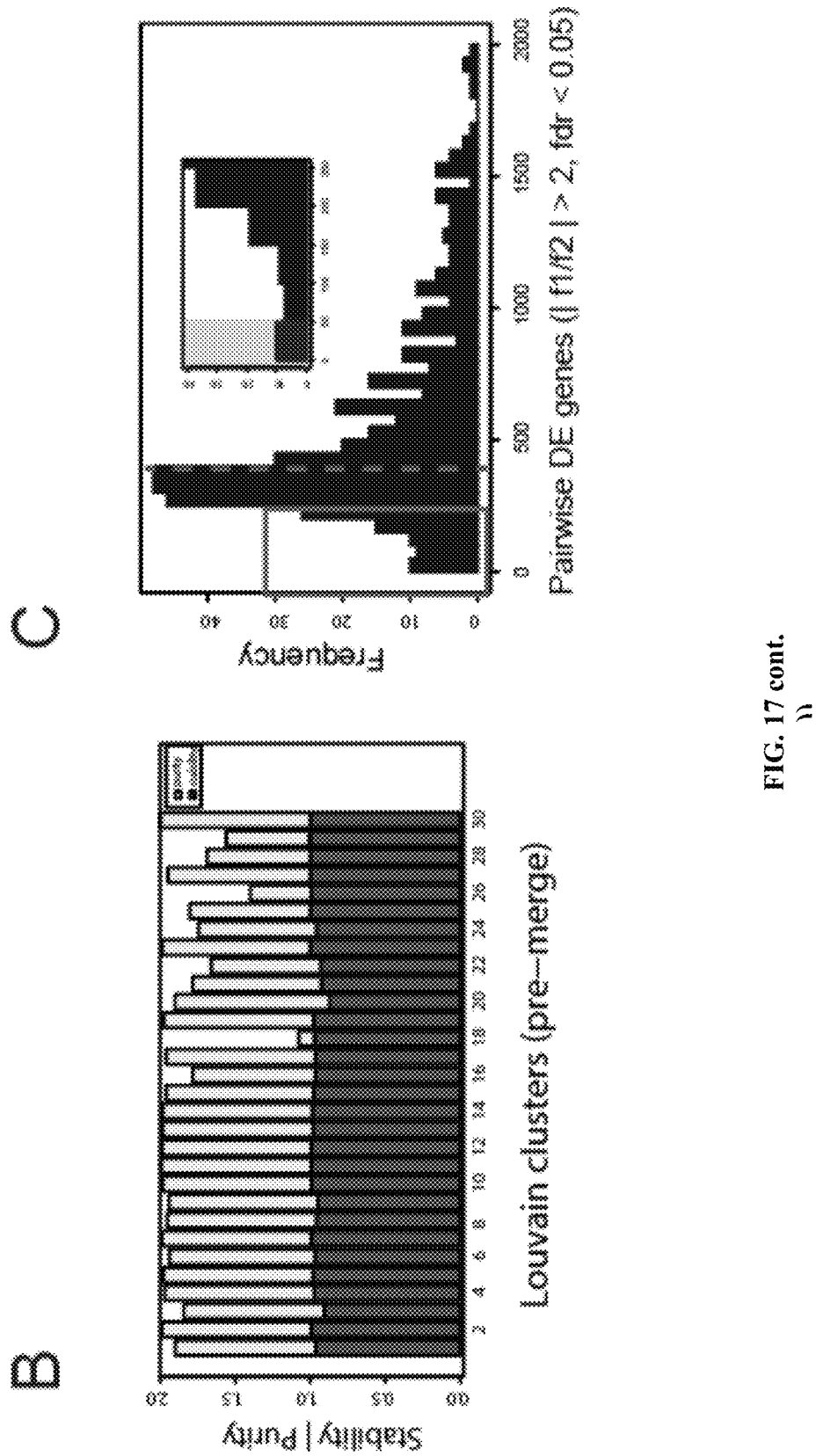
Figure 17:
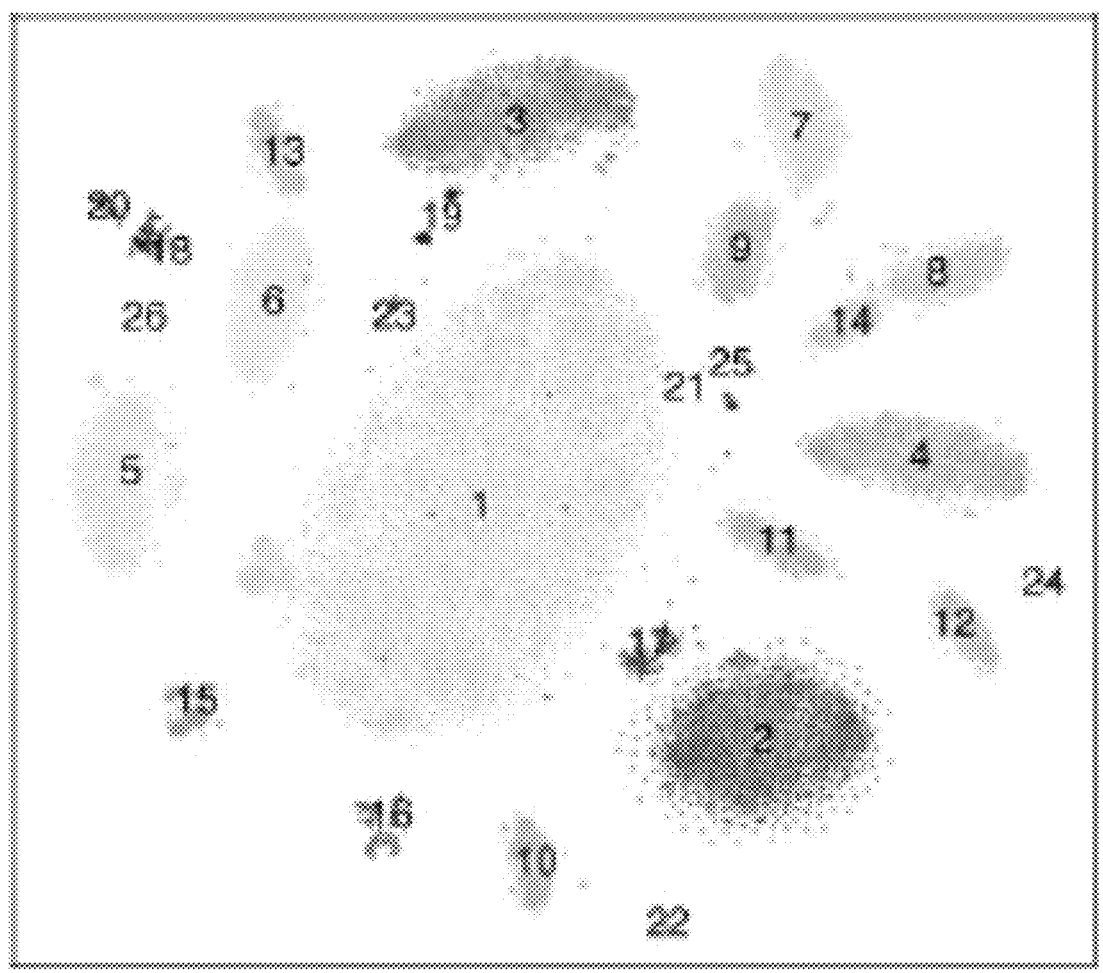
Figure 17:
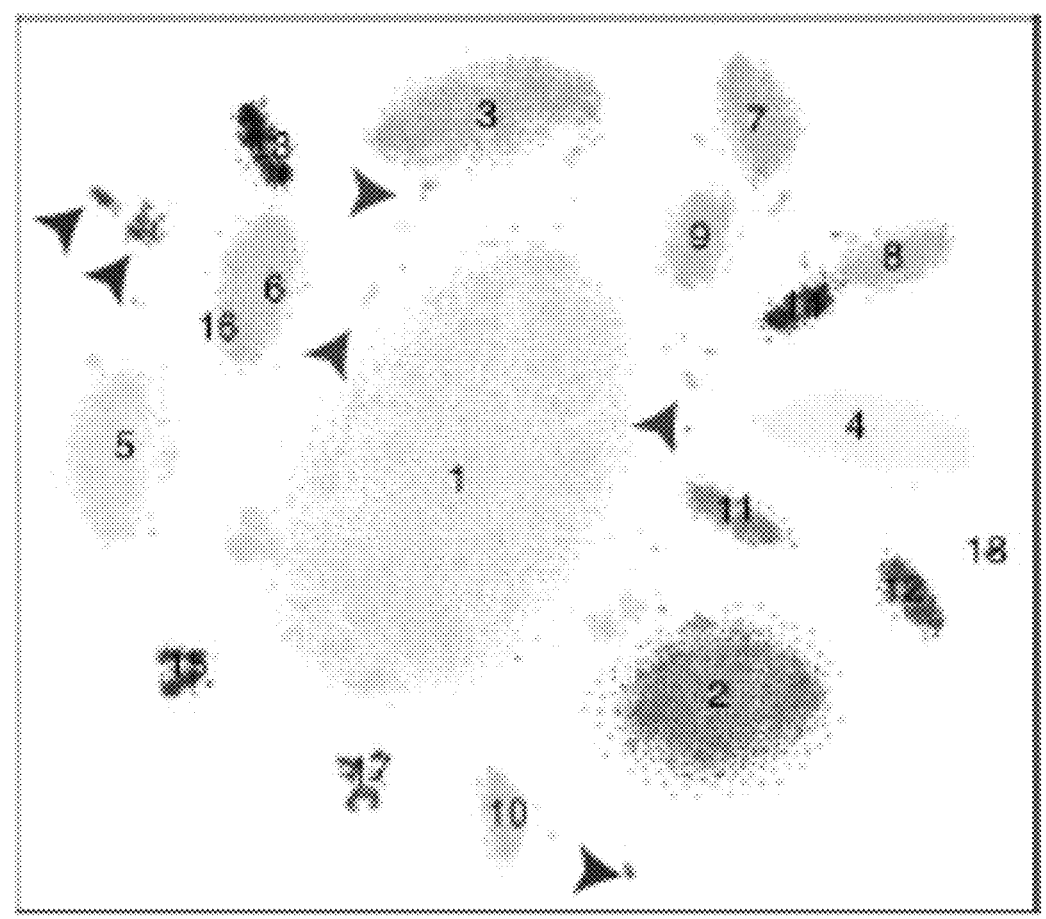
Figure 17:
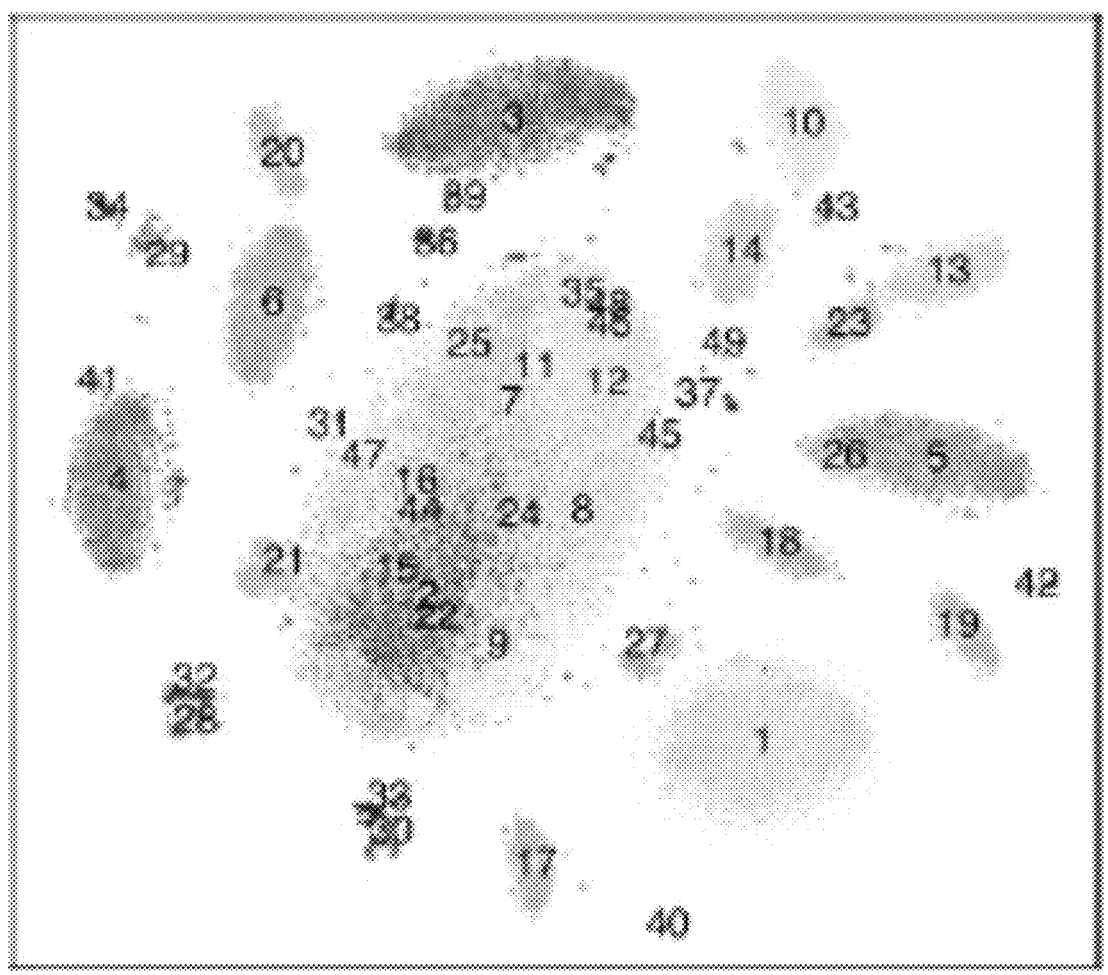
Figure 17:
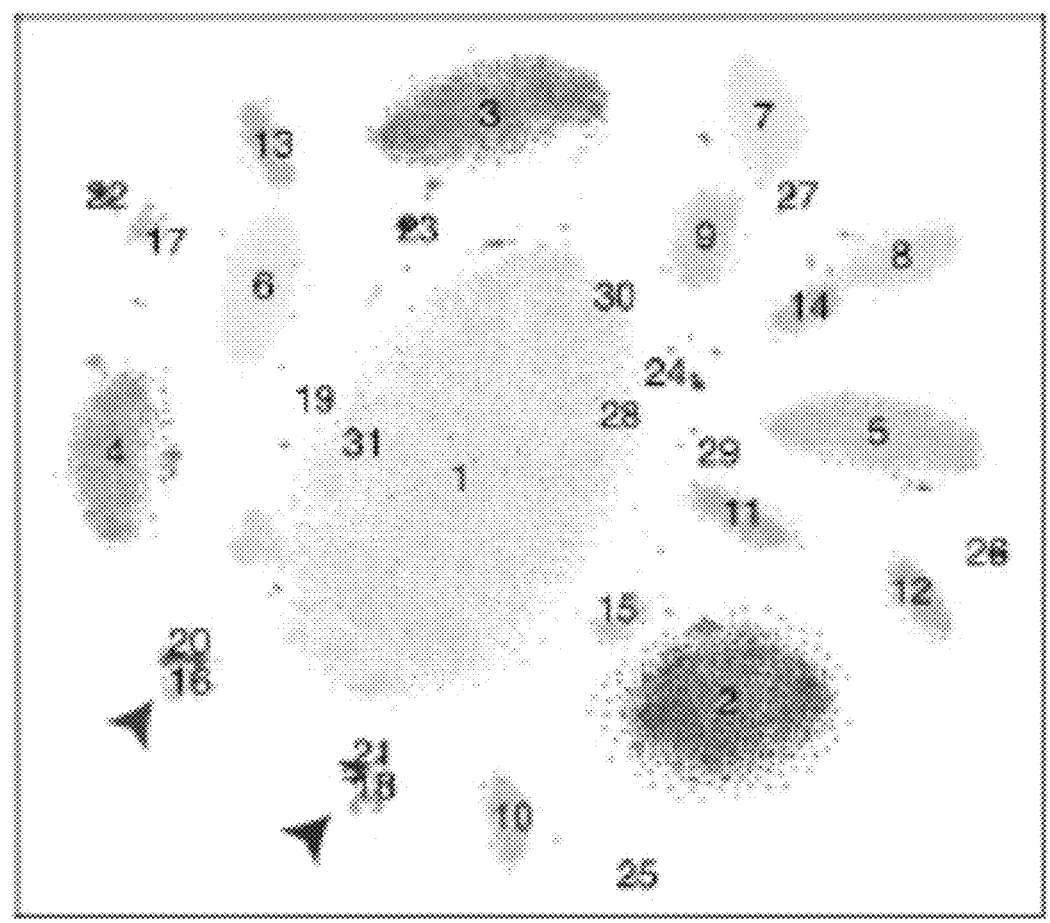
Figure 17:
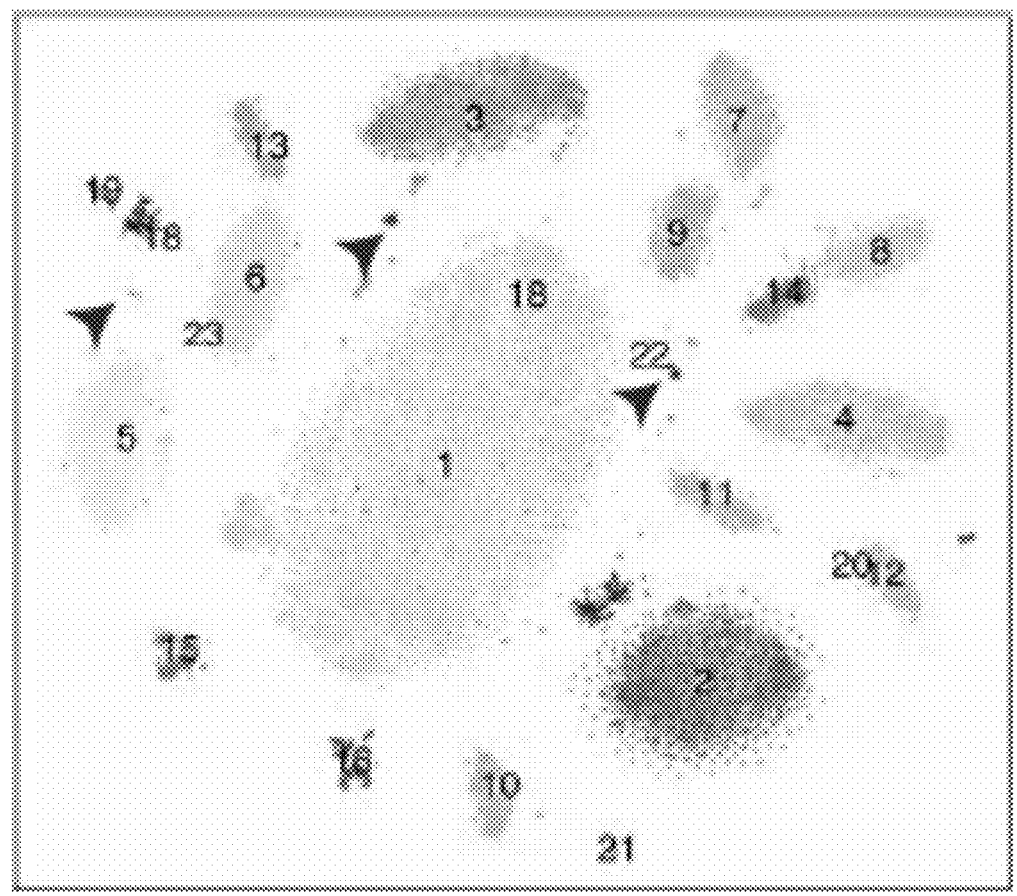
Figure 17:
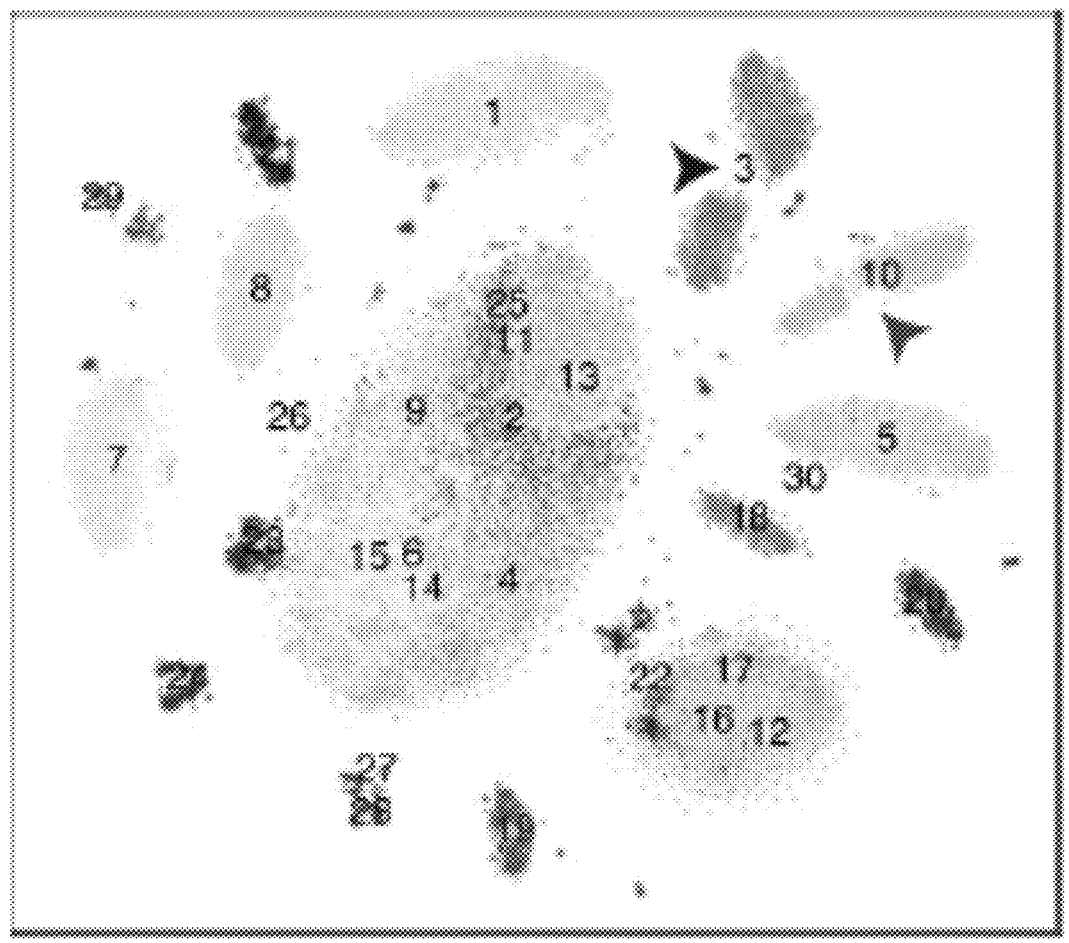
Figure 17:
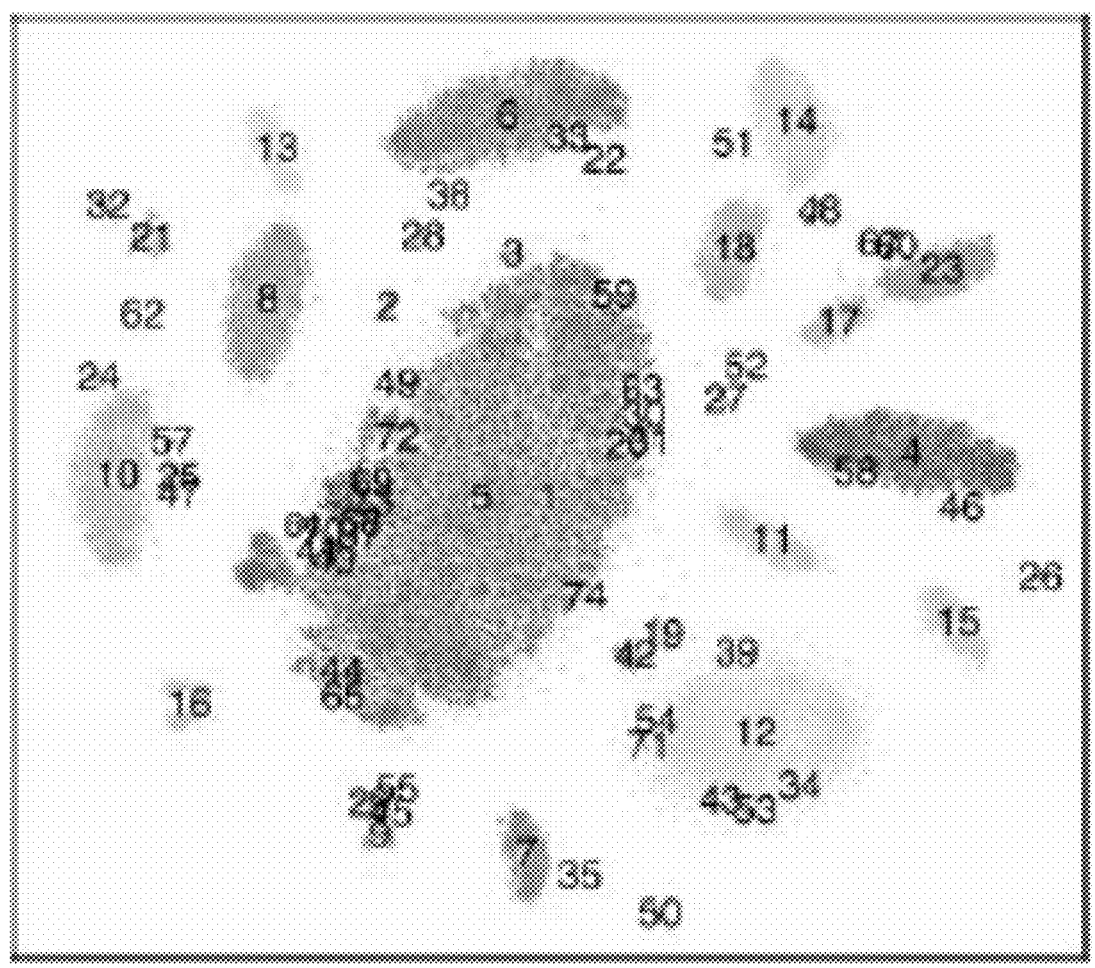
Figure 17:
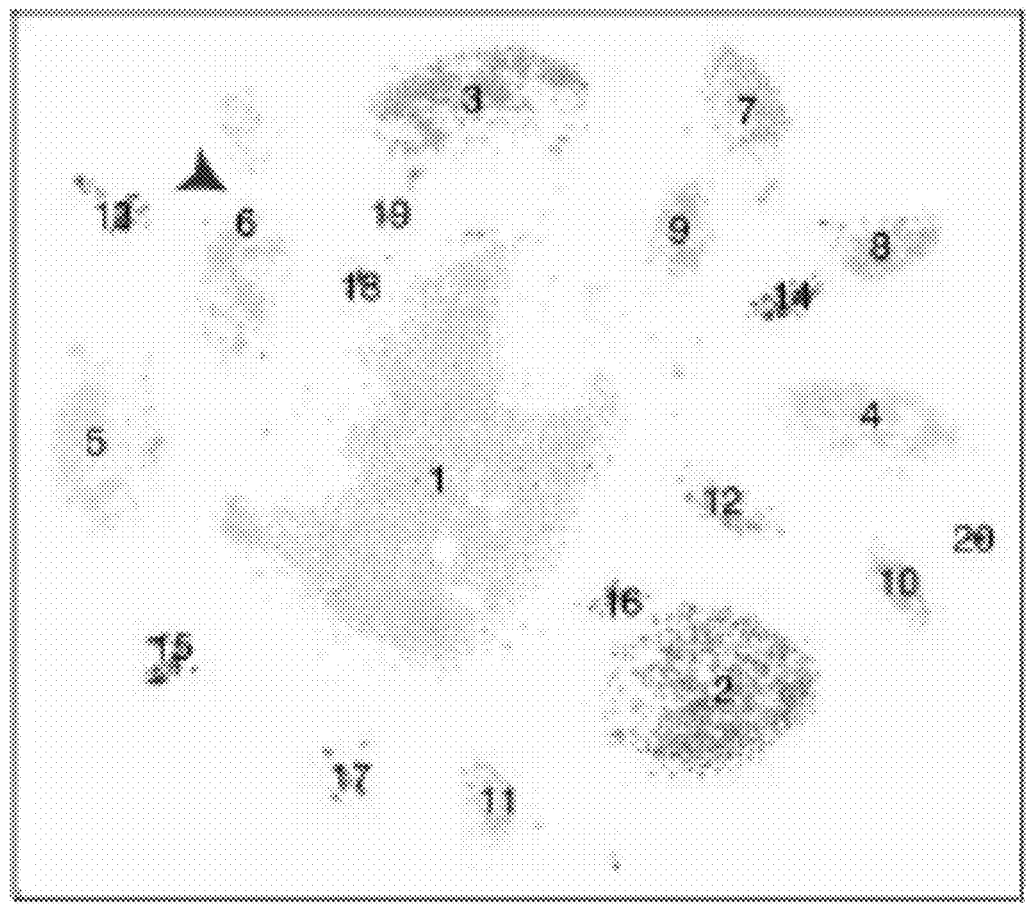
Figure 17:
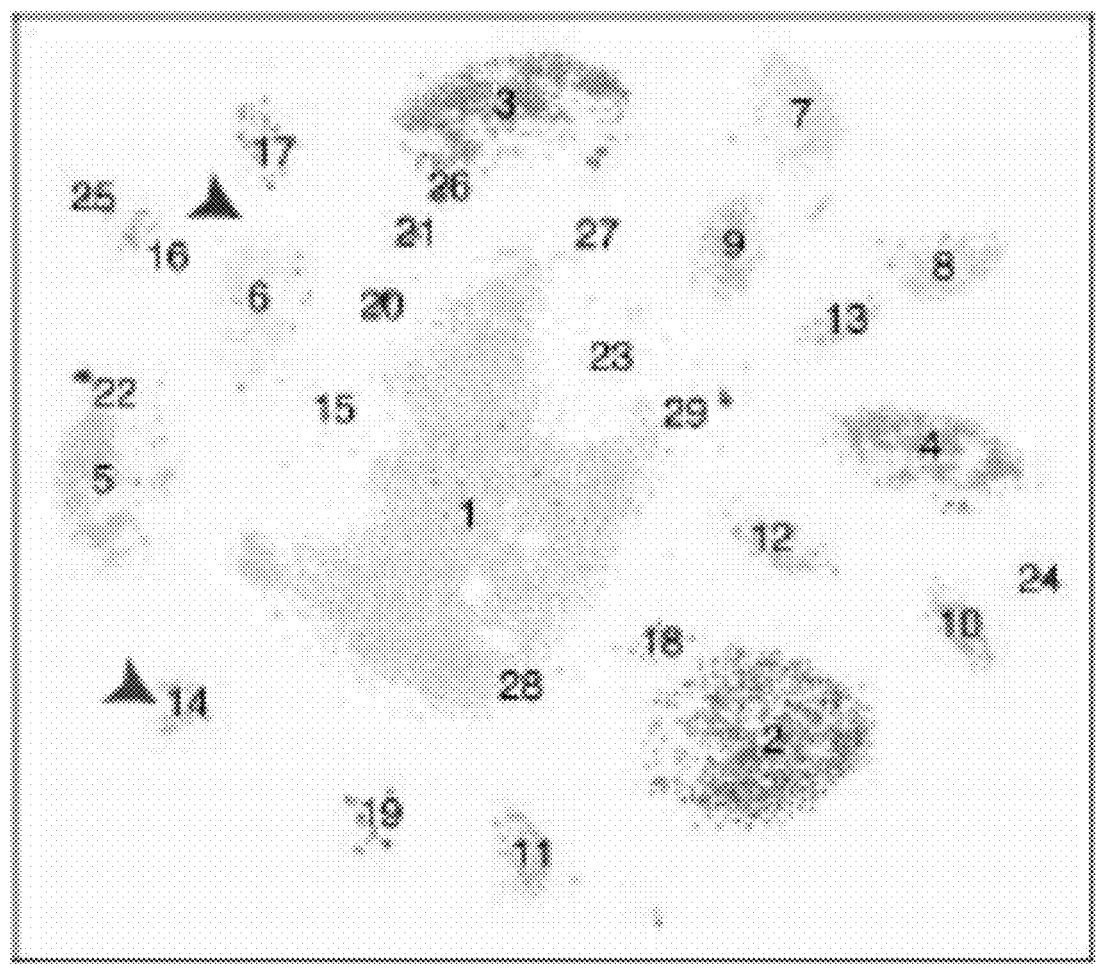
Figure 17:
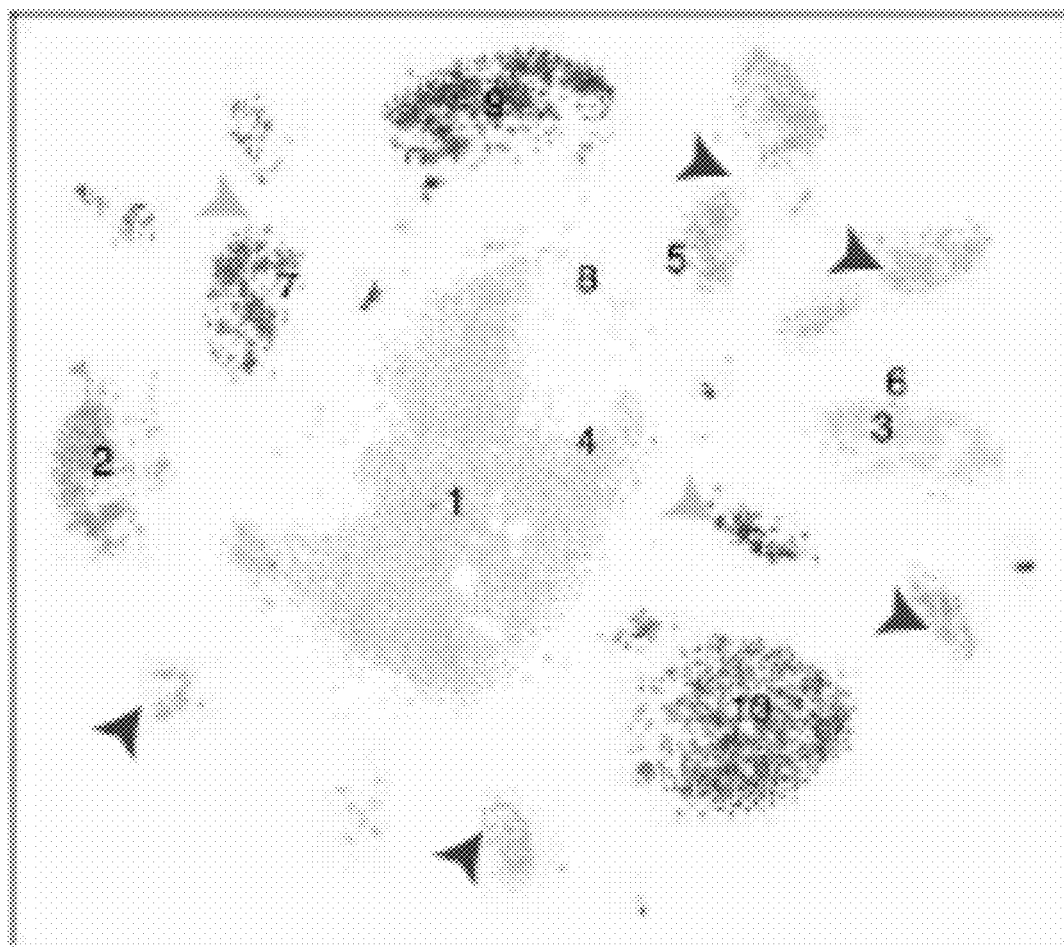
Figure 17:
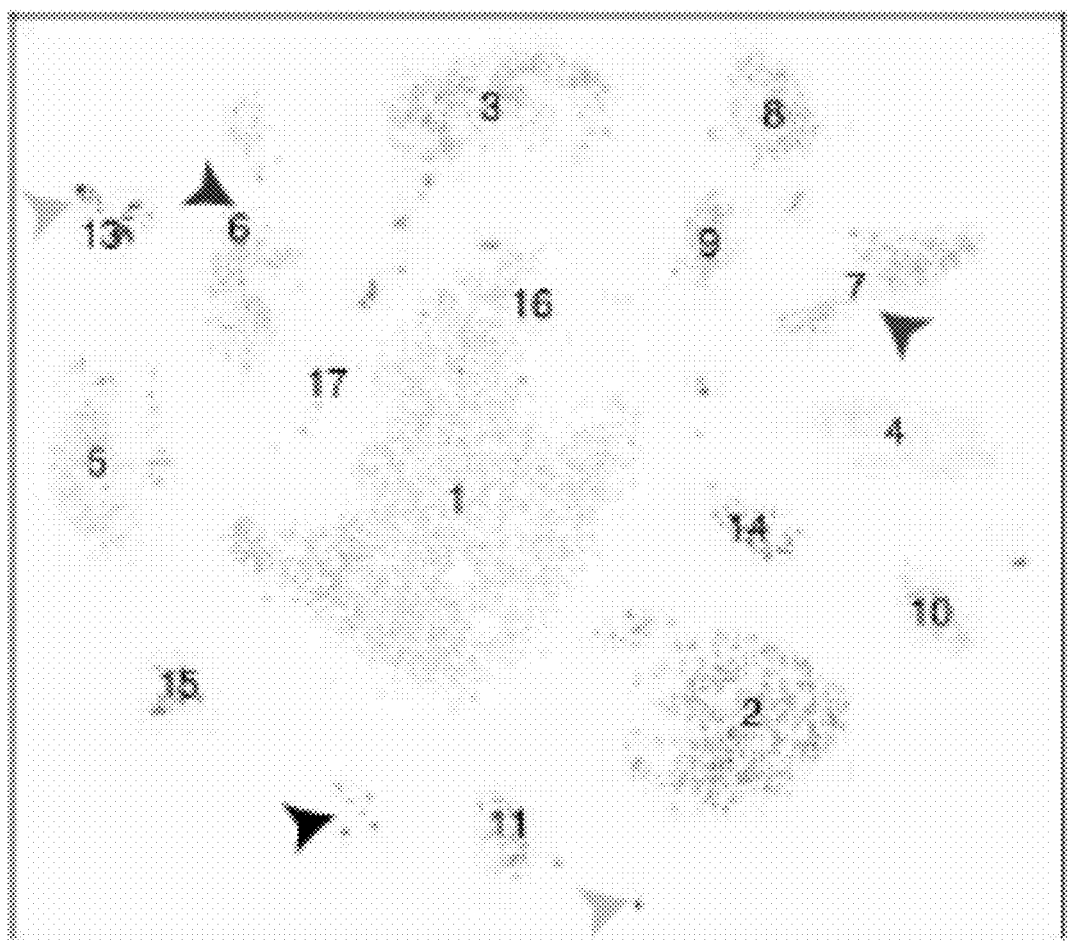
Figure 17:
Figure 17:
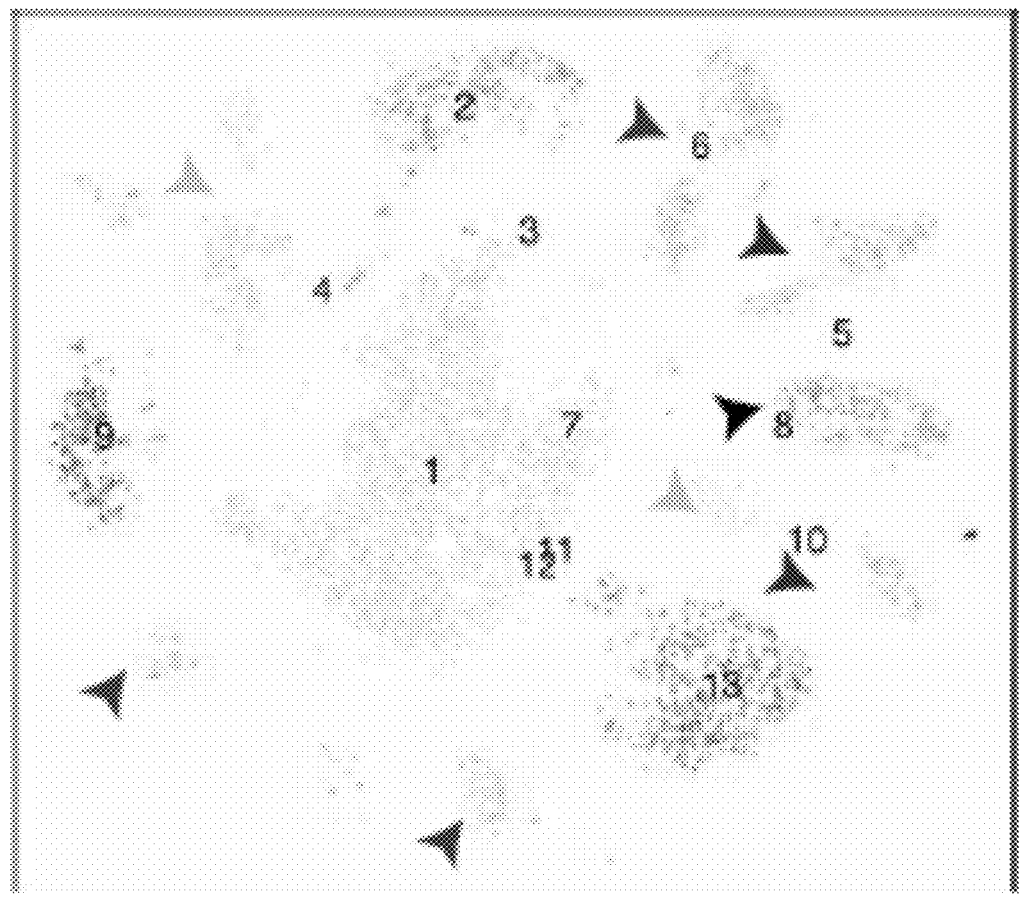
Figure 17:
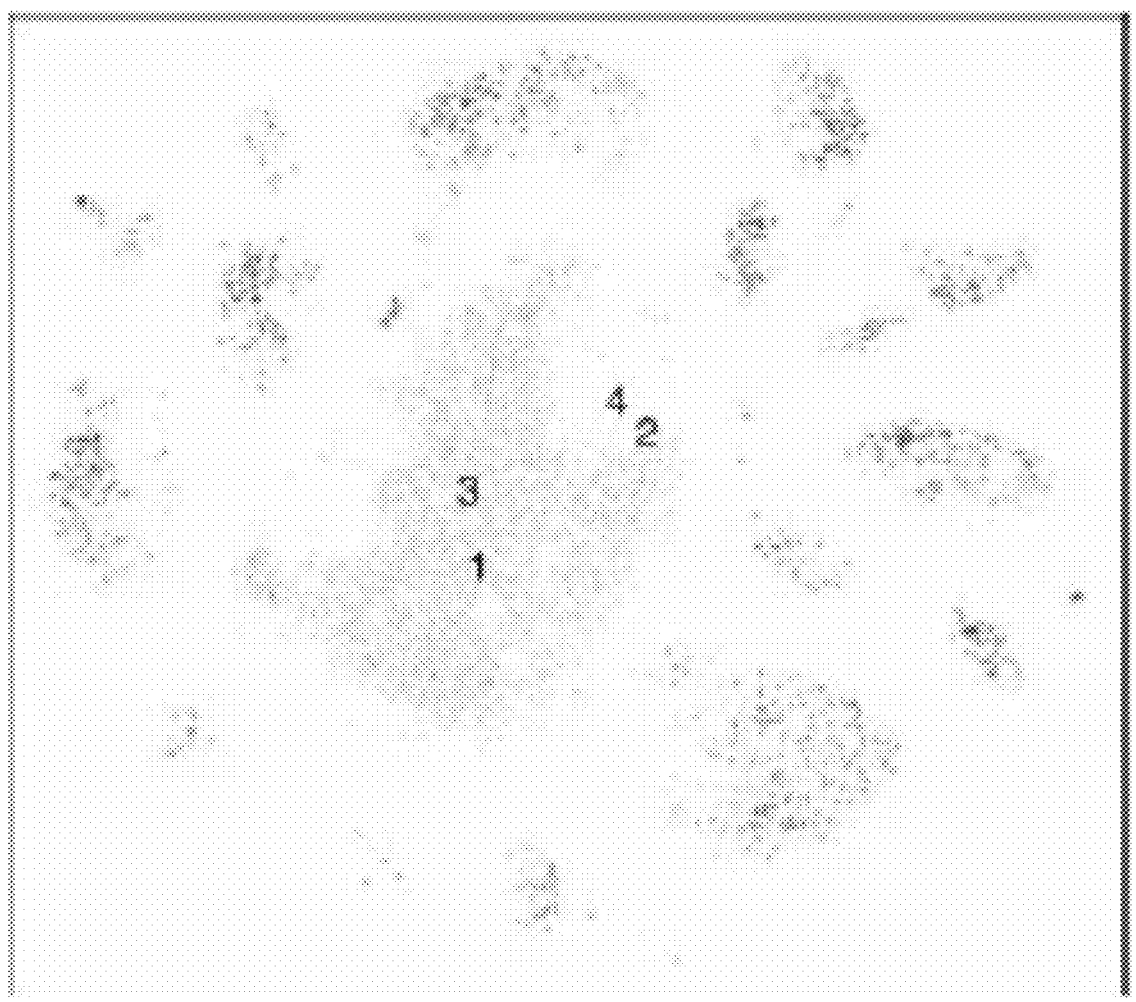

Example 3: Unbiased Graph Clustering Robustly Identifies 26 Putative Cell Type Clusters To identify cell types, first six different computational approaches were tested for clustering cells by their transcriptional profiles (FIG. 17). To avoid over-clustering, the clustering output was refined by merging clusters that did not show at least 50 differentially expressed genes (Panel C of FIG. 9). Of the methods tested, Louvain-Jaccard (Blondel et al., 2008; Levine et al., 2015) and Infomap (Rosvall and Bergstrom, 2008), two graph clustering algorithms, exhibited superior performance as judged by the close correspondence of clusters to the predicted number of BC types and known markers, their ability to accurately resolve clusters when applied on smaller subsets of the dataset, and their computational scalability (FIG. 3). Infomap nominated a larger number of clusters compared to Louvain-Jaccard (Panels A and F of FIG. 9), but most of these differences disappeared once transcriptionally proximal clusters were merged (FIGS. 3 and 4). While subsequent validation efforts were largely focused on output of Louvain-Jaccard, which produced thefewest spurious clusters before the merging step, the increased sensitivity of Infomap was beneficial for cell types present at low frequency, as discussed below. The reproducibility of the clusters was verified under bootstrap (Panel B of FIG. 17), as well as by varying the number of input genes or cells. Similar clusters were obtained when the PCs were constructed using a smaller set of 2,000 highly variable genes rather than the full set of genes (Panel H of FIG. 17), or when the analysis was repeated using only 50% of the cells in the dataset corresponding to a single experiment (13,938 cells from Batch 1; FIG. 5, Panels K and L of FIG. 17). When the number of input cells was reduced to 18% of the dataset (5,000 cells), however, three pairs of closely-related clusters were merged (Panel N of FIG. 17), suggesting that large numbers of cells are important for resolving transcriptionally similar types (as we found previously for amacrine neurons, (Macosko et al., 2015)).

The "cluster stability index" defined as, $$\text{Stability}_k = 1 - (1/500) \Sigma \text{Hi}k/\text{HiTot}$$

$$\sum_{i=1}^{500}$$

where HiTot is the overall Shannon diversity index (entropy) of the cluster distribution of cells in realization i $\{pj\}_{j=1}^{N1}$ and Ni is the number of clusters found in realization i by Louvain-Jaccard, before merging. Then, $$\text{HiTot} = -\Sigma pj \log pj \log(pj)$$

$$\sum_{j=1}^{Hi}$$

k is the Shannon diversity of the cluster distribution of only the cells belonging to cluster k in realization i $\{fjk\}_{j=1}^{Ni}$ $$\text{Hi}k = -\Sigma fj \; k \log (fjk)$$

$$\sum_{j=1}^{Ni}$$

As the formula suggests a cluster is "stable" if Hi k is much less than the background entropy HiTot. The "cluster purity index" is defined as, $$\text{Purity}_k = (1/500) \Sigma |\text{cells}_k \subset \text{cellsclust}(i,k)|/|\text{cellsclust}(i,k)|$$

$$\sum_{i=1}^{500}$$

where, clust(i, k) denotes the cluster in realization i that contains the maximum proportion of cells from the original cluster k. $\text{cells}_k$ denotes the cells that comprise cluster k.

Example 4: Fourteen BC Clusters, Seven of which Align with Known Types

Figure 6:
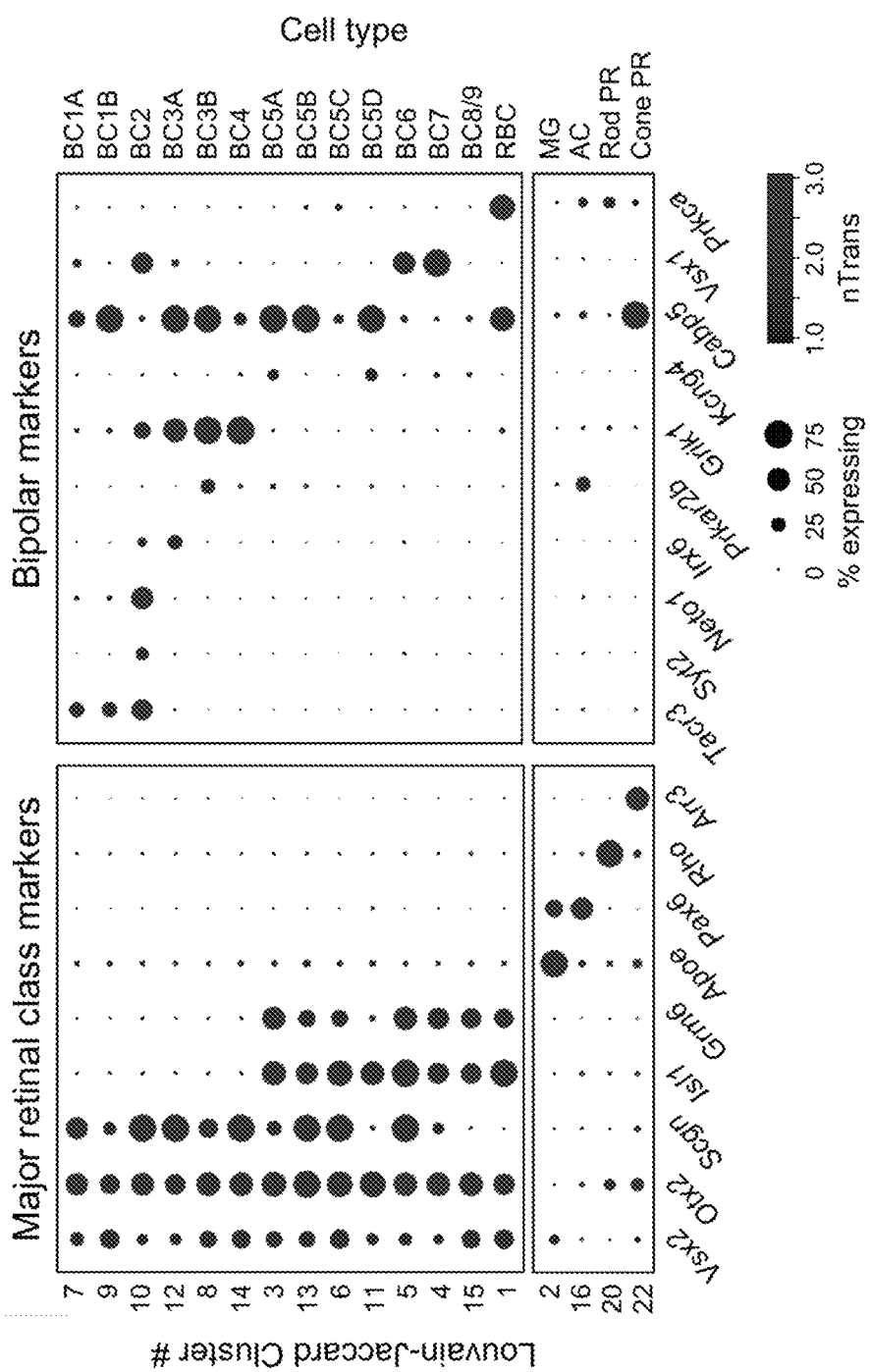

Most of the 26 clusters (FIG. 3) could be tentatively assigned to known retinal types, based on previously established markers (FIG. 6). Fourteen clusters (Cluster 1, and 3-15), each of which contained >300 cells were identifiable as BCs because they robustly expressed the pan-BC markers Vsx2 and Otx2 (Baas et al., 2000; Burmeister et al., 1996), and lacked expression of markers of other classes of retinal neurons. These clusters comprised 84% of all cells analyzed, suggesting that sorting resulted in a 12-fold enrichment of BCs compared to their observed frequency of about 7% in whole retina (Jeon et al., 1998). Müller glia, which also express Vsx2, comprised cluster 2 (n=2,945, 10.5% of cells) and were readily identifiable based on the high expression of Apoe, Glul, Aqp4, and the absence of Otx2 (Hatakeyama et al., 2001; Roesch et al., 2008). Rod photoreceptors (cluster 20), which comprise 70-80% of all retinal cells, accounted for fewer than 2% of our dataset (Jeon et al., 1998). The remaining 10 clusters, together comprising 2% of the population, included cell doublets with mixed signatures (clusters 17-19, 21, 23-26), cone photoreceptors (cluster 22) and amacrine cells (cluster 16). Together, contaminant cells and cell doublets comprised less than 4% of the population. It is a strength of scRNA-seq methods that undesired types can be identified and excluded from further analysis rather than contaminating the transcriptomes of the relevant types.

Figure 7:
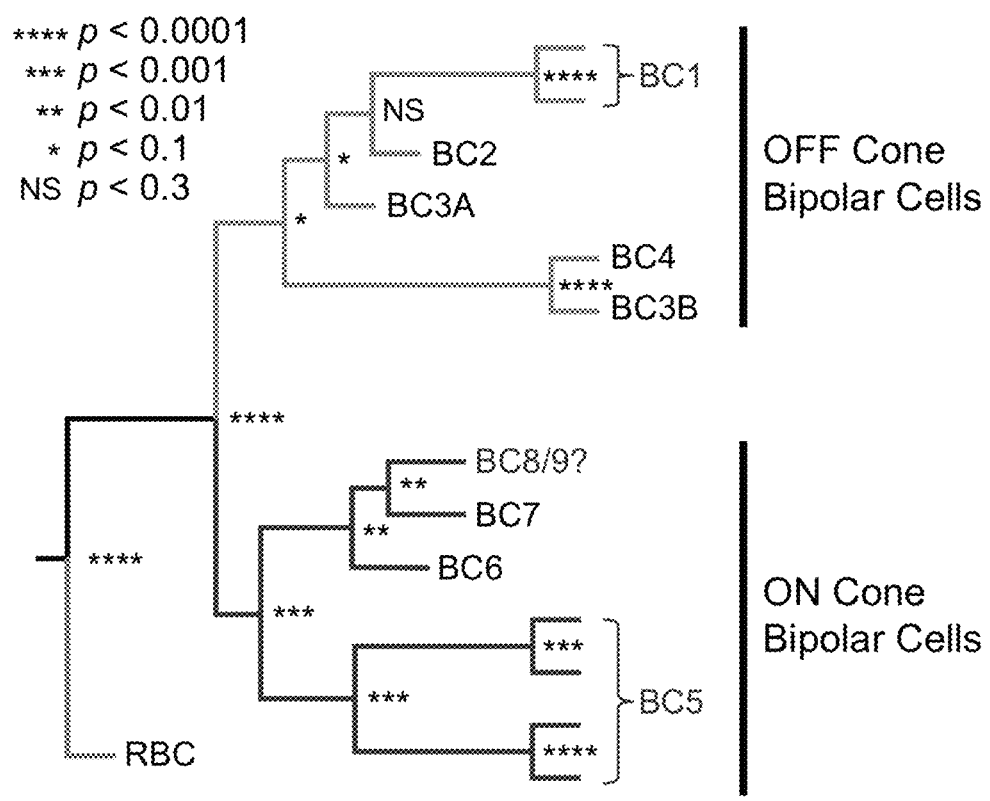

The 14 BC clusters were assigned to types by inspecting the expression of known markers in the clusters. Clusters could be divided into rod and cone BCs based on the presence or absence of RBC markers (Prkca, Car8, Sebox; cluster 1) or the broad cone BC marker, Scgn (clusters 3-15; FIG. 6) (Kim et al., 2008; Puthussery et al., 2010; Vaquero et al., 1996). The cone BC clusters could be further divided into ON (clusters 3-6, 13, 15) and OFF (clusters 7-10, 12, 14) BC types based on the ON bipolar markers Isl1 and/or Grm6 (Elshatory et al., 2007a; Masu et al., 1995; Ueda et al., 1997). Additional known markers allowed for the 1:1 assignment of six clusters (4, 5, 8, 10, 12, and 14) to six matching cone BC types (BC7, BC6, BC3B, BC2, BC3A and BC4, respectively) (FIG. 6). Relationships between the putative BC types, building a dendrogram by hierarchical clustering of the clusters' average expression vectors were evaluated using a resampling method that estimates the confidence level of each split (FIG. 7). Finally, as an additional test of our computational approach, about 5,500 BCs from our previous whole retina Drop-seq study were reanalysed. The improved computational approach enabled resolution of more BC types than was reported in the previous study. However distinctions among transcriptionally similar types were not achieved, presumably due to the smaller number of cells analyzed, and also cross-contamination by transcripts of rod photoreceptor markers, which constituted >65% of cells in the dataset (Panels A-F of FIG. 18). Seven BC clusters had more complex relations to prior knowledge. They were tentatively labeled based on marker expression (FIG. 6) and positions on the dendrogram (FIG. 7). Two of these clusters (7 and 9) expressed genes characteristic of BC1, although previous studies have only reported a single BC1 type. Four clusters (3, 6, 11, and 13) had gene expression suggestive of BC5 identities, whereas only three had been identified previously, including the putative XBC type (Helmstaedter et al., 2013). The smallest BC cluster (15) expressed ON BC genes but no known type specific markers; it was tentatively assigned to BC8/BC9 by a process of elimination.

Example 5: Novel Validated Molecular Markers for Six BC Types

Figure 8:
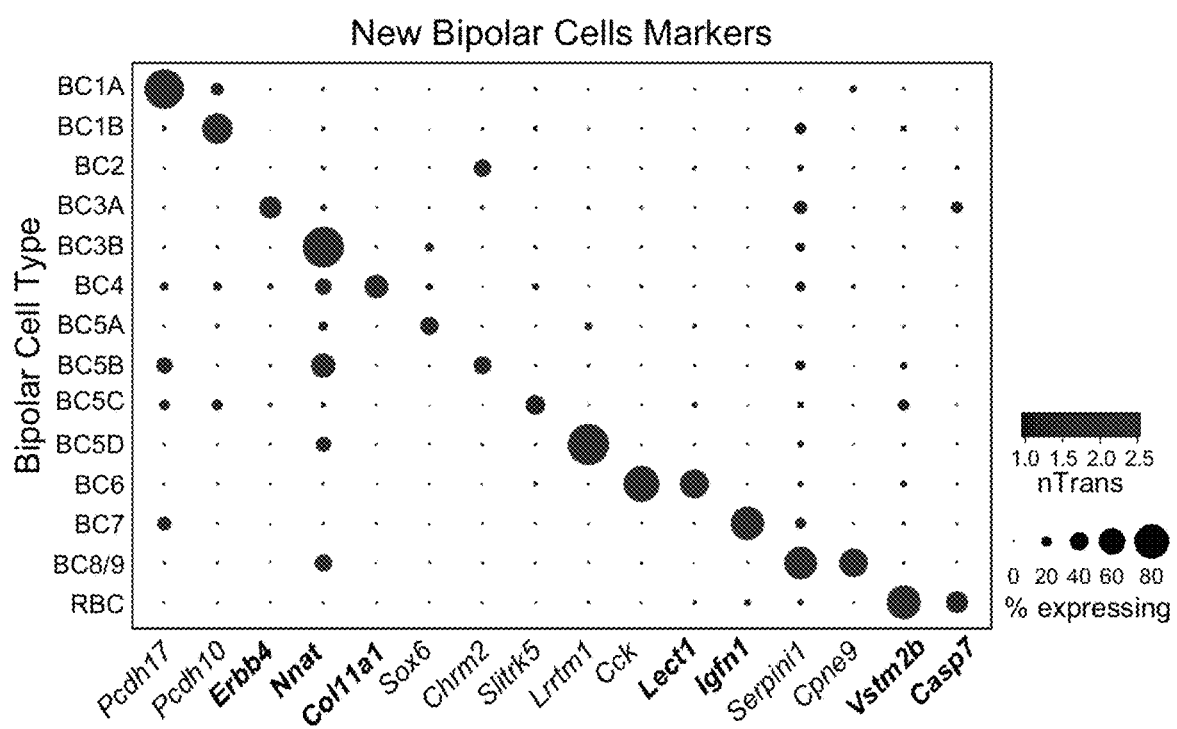
FIGS. 8-10 depict validation of markers for six BC types.
Figure 10:
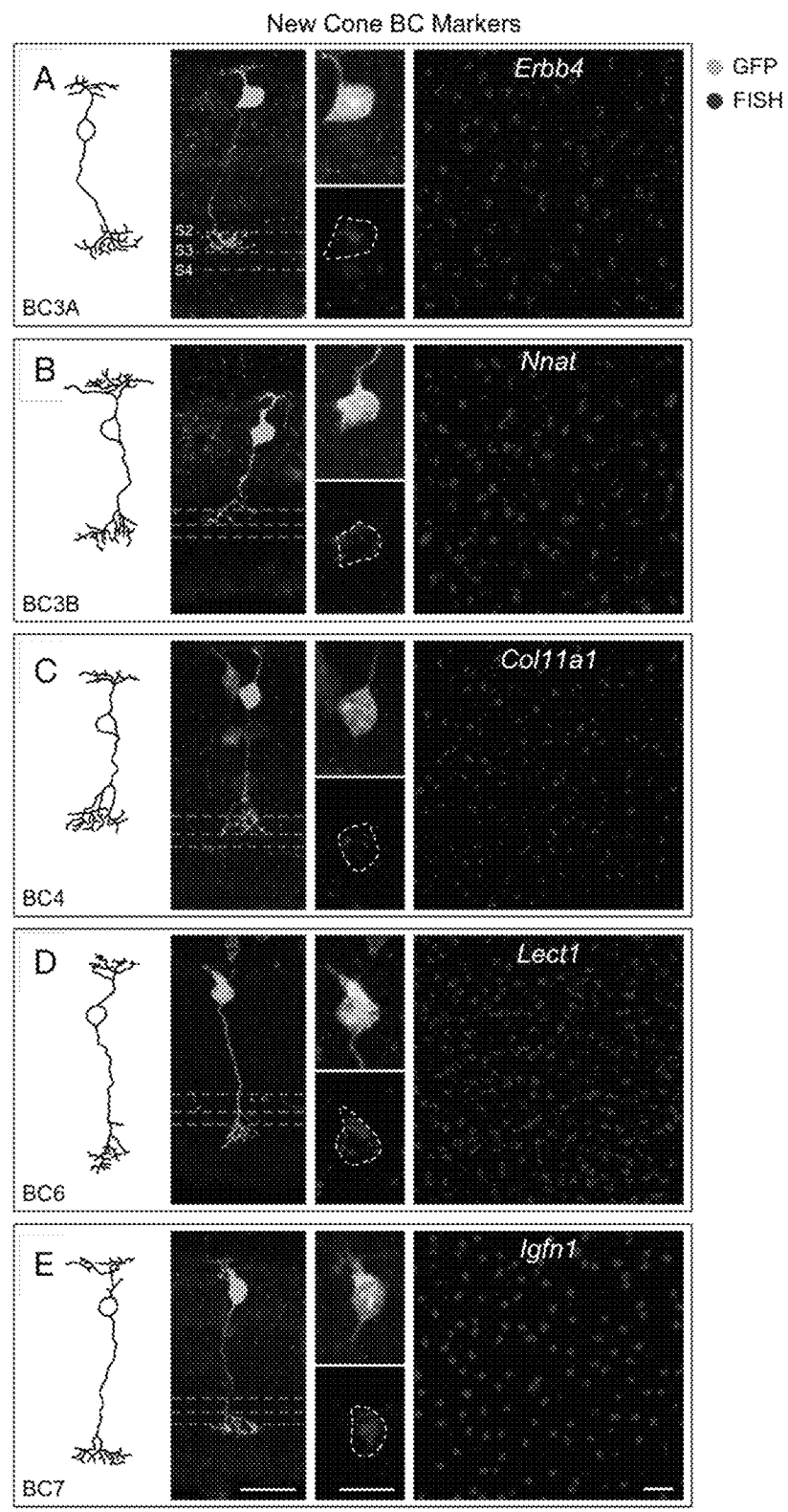
Figure 18:
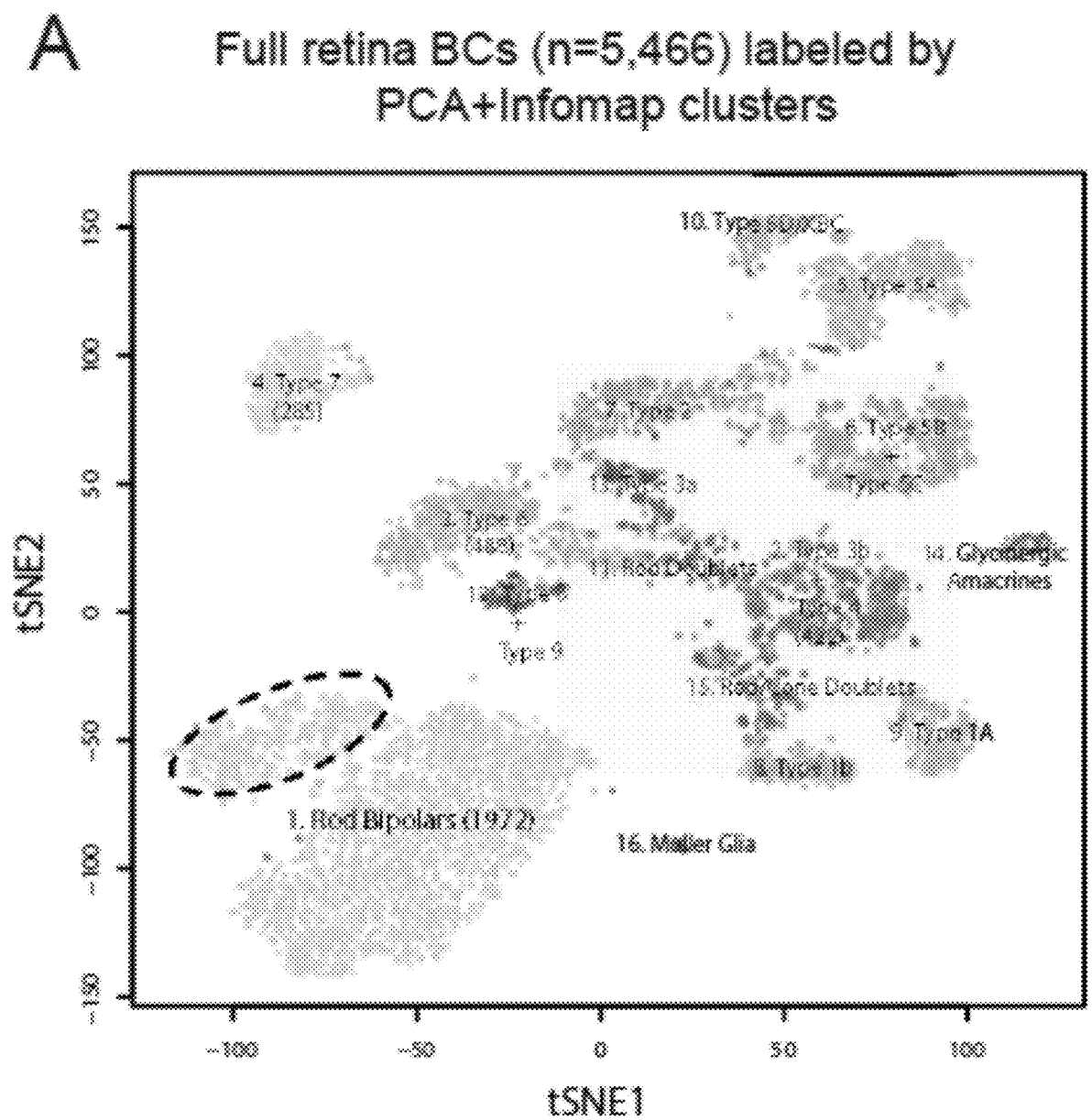
FIG. 18 shows reanalysis with full retina Drop-seq data, comparison with results from this study, and heatmap of differentially expressed genes across BC clusters, related to FIG. 1. Panels A-B of FIG. 18 depict recomputed tSNE representation of 5,466 BCs from full retina Drop-seq data. Cells are colored according to their cluster identity based on Infomap in the panel of Panel A of FIG. 18. In the panel of Panel B of FIG. 18, they are colored according to their original cluster identity in (Macosko et al., 2015), where clustering was performed using tSNE+DBSCAN. Panel C of FIG. 18 is a matrix of Pearson correlation coefficients of cell-averaged gene expression signatures of Infomap clusters in the full retina Drop-seq data shown in the panel of Panel A of FIG. 18 (rows) and final Louvain-Jaccard clusters in the Vsx2-GFP Drop-seq data shown in FIG. 3 (columns). Clusters are labeled according to their tentative types based on top differentially expressed genes. Average expression values for every gene within a sample were computed by first averaging the normalized transcript counts Mij across all the cells, adding 1 and then taking the logarithm. Panel D of FIG. 18 shows a test set performance of random forest model trained on the Vsx2-GFP dataset with Louvain-Jaccard cluster labels. A training set was formed by choosing about 15% of cells from the full dataset labeled according to the Louvain-Jaccard method (FIG. 3). Cells were chosen only from the subset of the data corresponding to 14 BC types, Müller glia, rod photoreceptors, cone photoreceptors and amacrine cells, and the remaining cells from these clusters were held out as the 'test set'. The trained RF model was then used to classify each cell in the test set, and the predicted cluster label (one of 18, columns) was compared to its withheld cluster label (rows), and the result is shown as a confusion matrix. A cell was only assigned a class if >15% of trees in the RF model contributed to the majority vote, else it was deemed 'unclassified'. Panel E of FIG. 18 is a confusion matrix of RF-assigned class (columns) vs. tentative cluster label based on top differentially expressed genes (rows) in the full retina Infomap clusters (rows). A cell was only assigned a class if >15% of trees in the RF model contributed to the majority vote, else it was deemed 'unclassified'. Panel F of FIG. 18 depicts violin plots showing Rho expression in the full retina Infomap clusters (upper) and the Vsx2-GFP final Louvain-Jaccard clusters (lower). Panel G of FIG. 18 shows a heatmap of transcript counts showing differentially expressed genes across the 14 BC (FIG. 3; Note BC8/9 is a single cluster) and MG clusters. Rows correspond to individual genes found to be enriched in individual clusters based on a binomial test (FDR <0.01); columns are individual cells, ordered by cluster. The expression scale is capped at 2 since very few non-zero transcript counts (<20%) are higher than this number.
Figure 18:
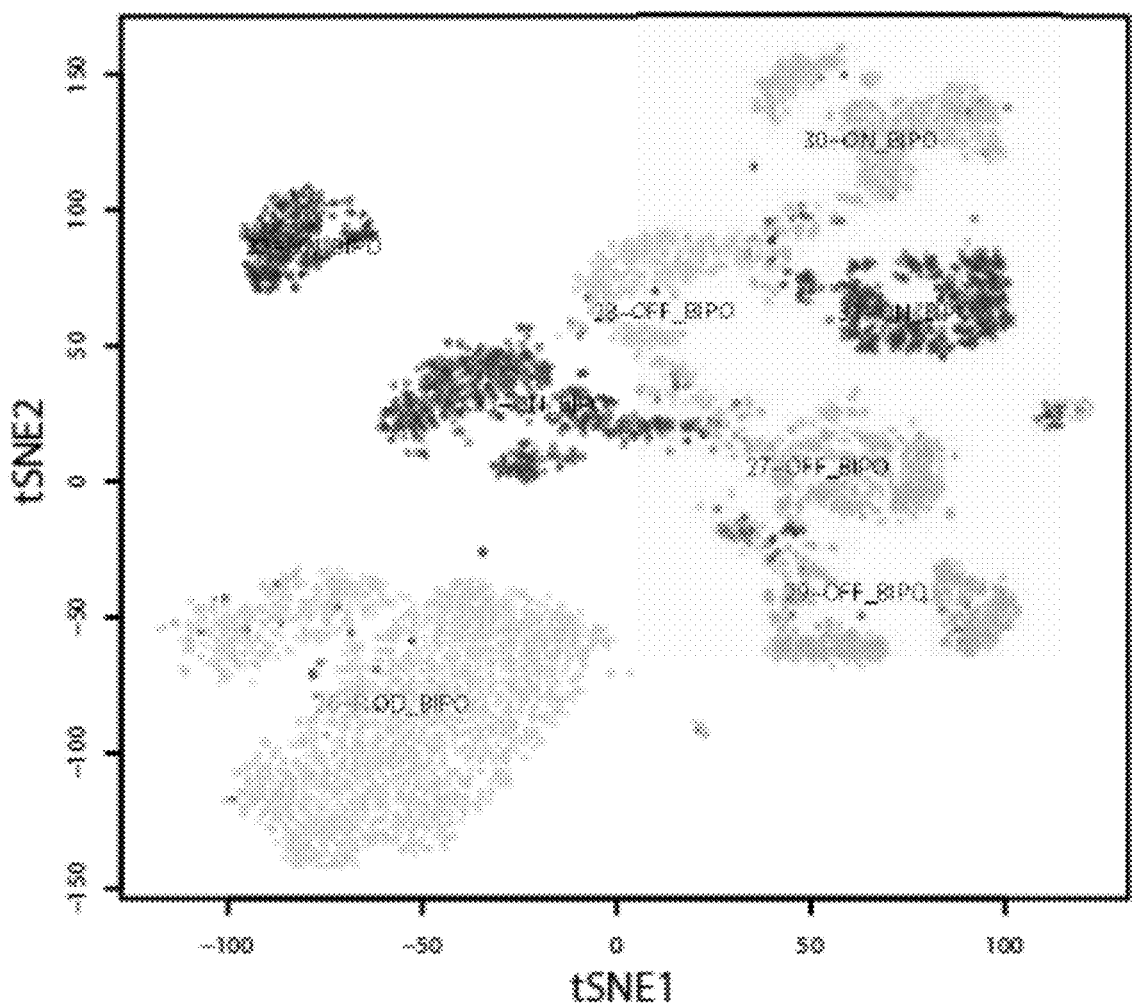
Figure 18:
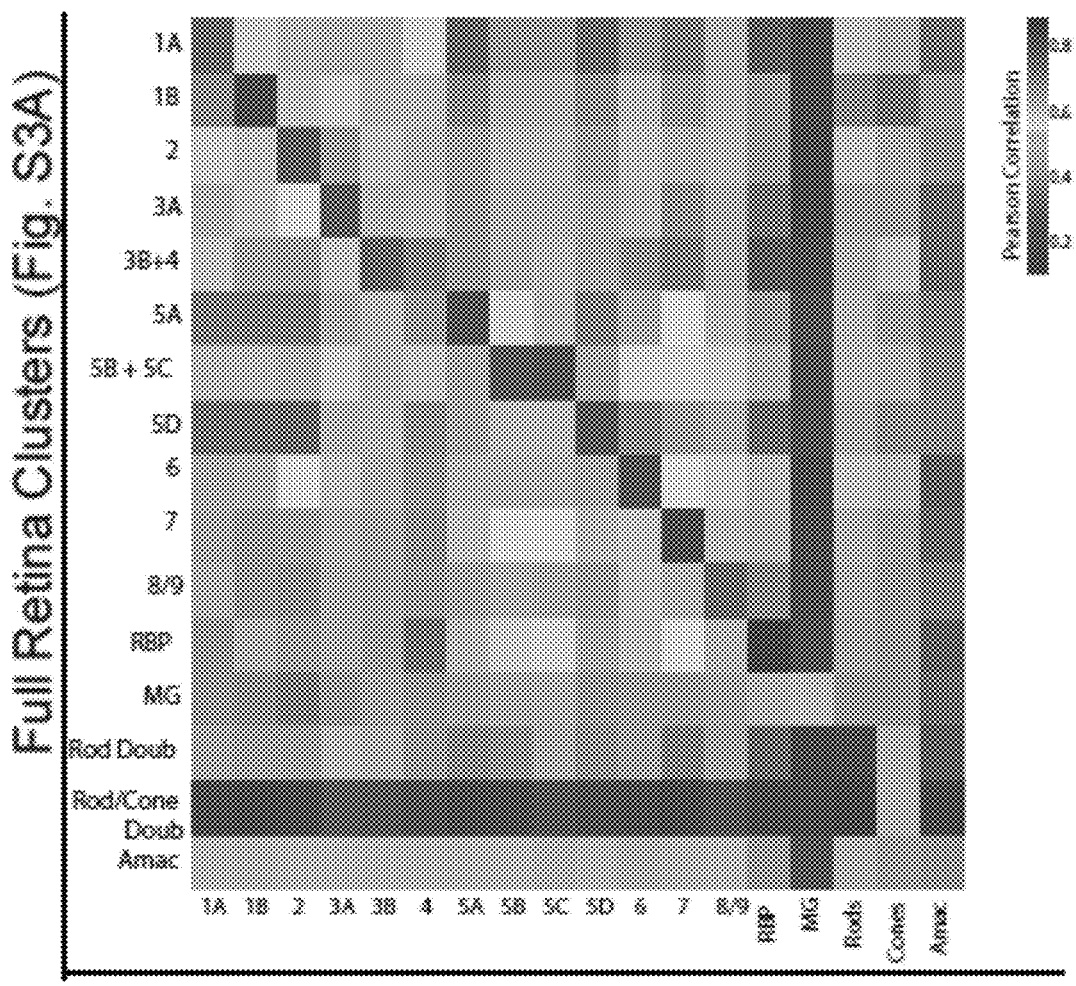
Figure 18:
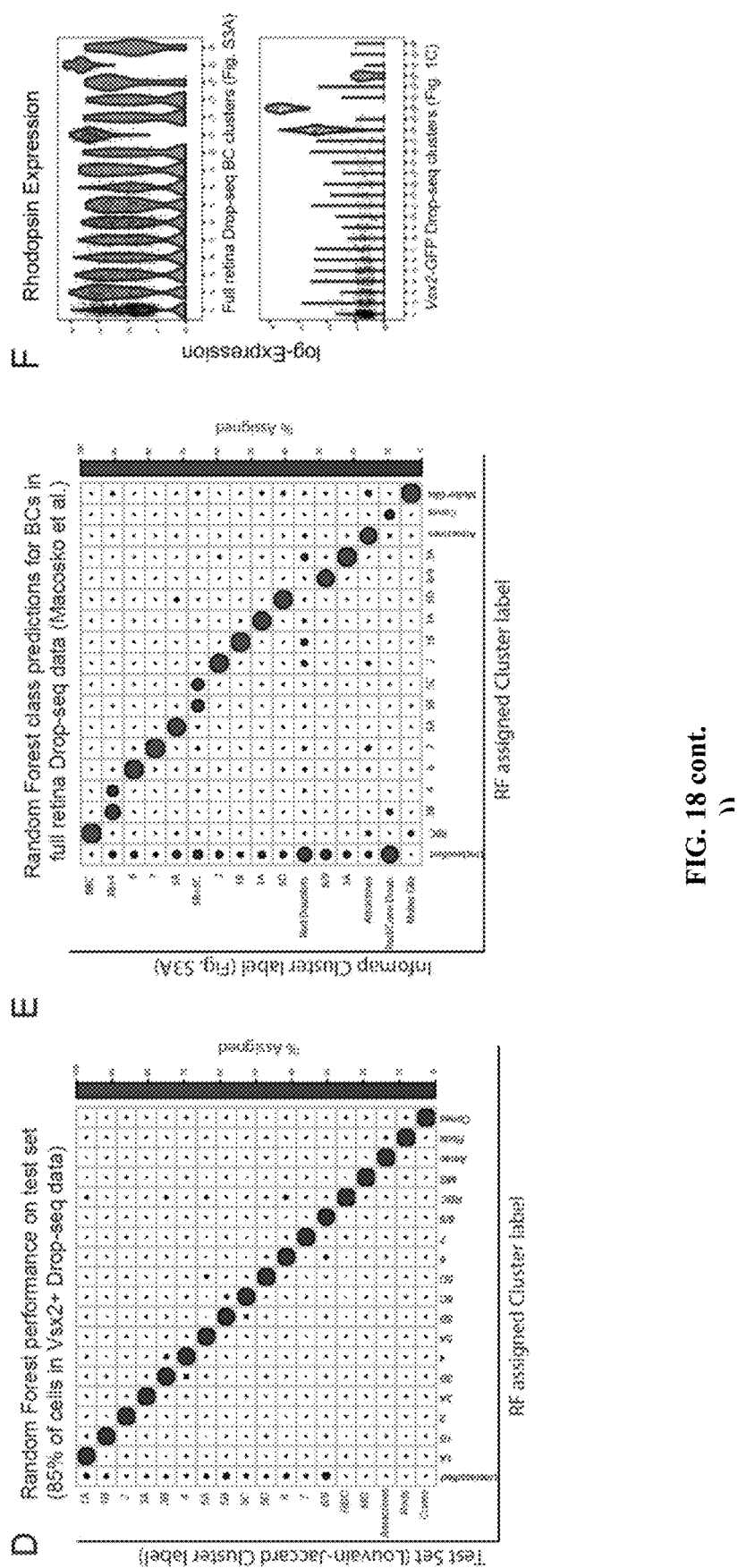
Figure 18:
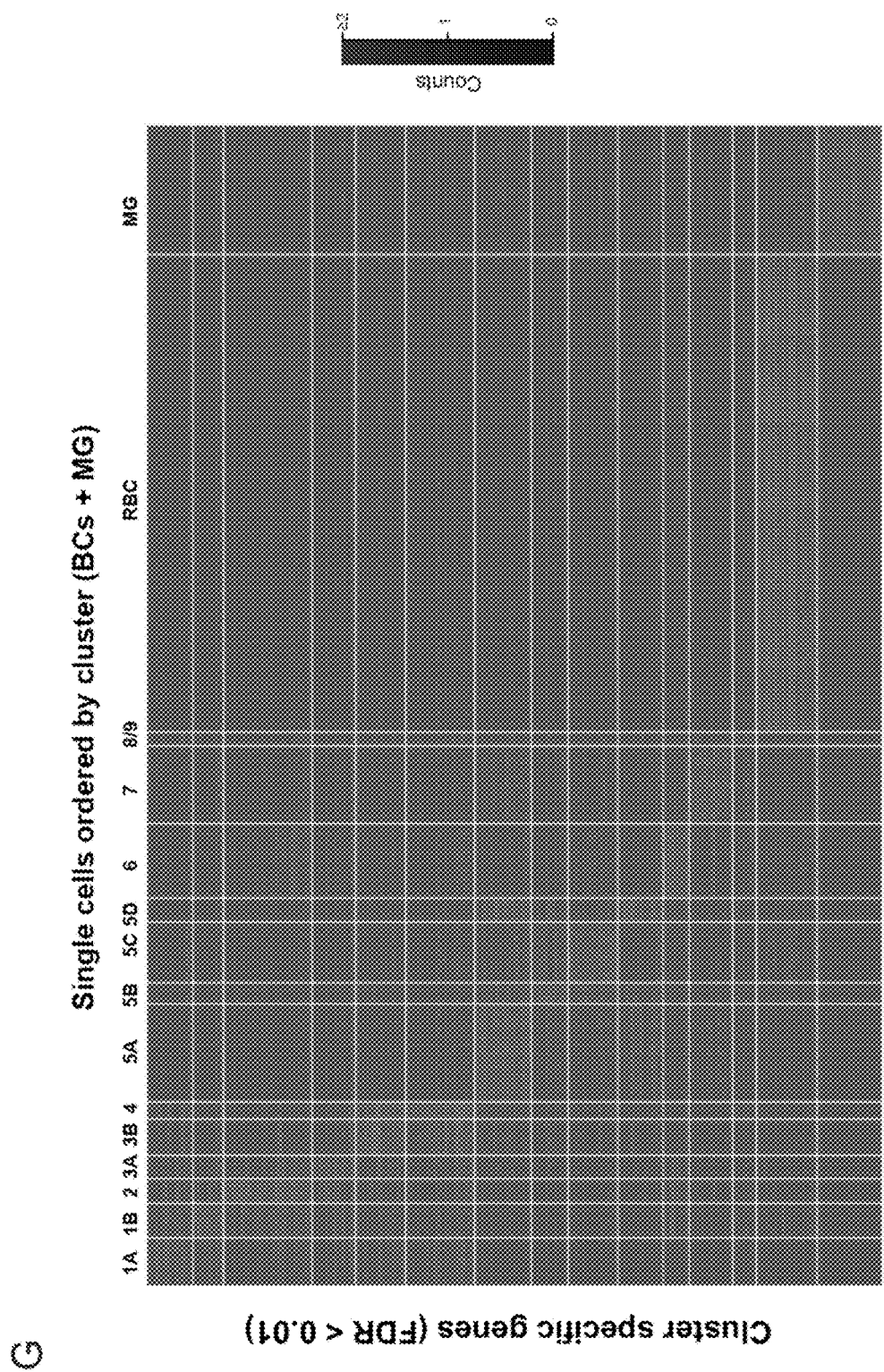
Figure 19:
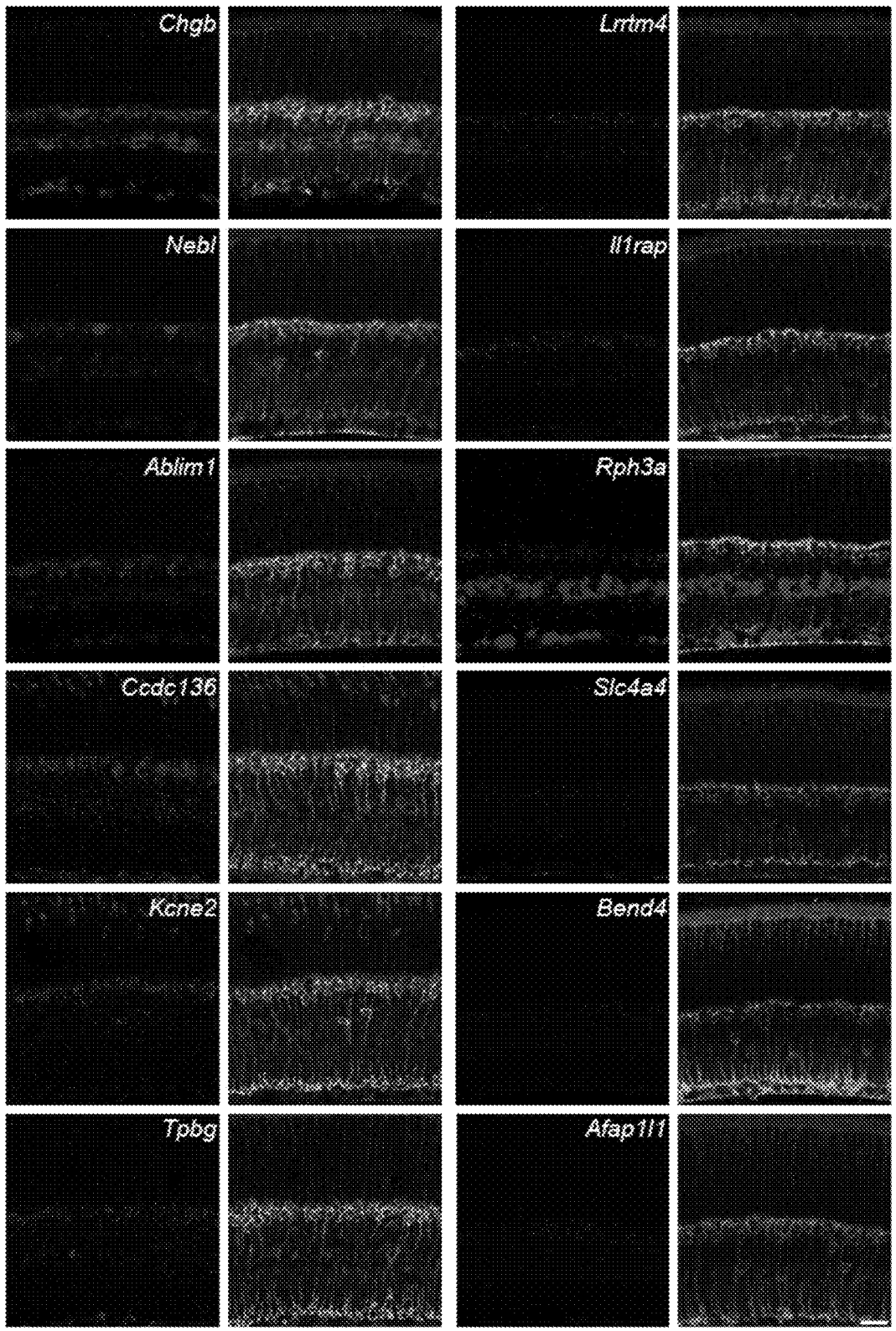
FIG. 19 shows a validation of RBC markers, related to FIGS. 8-10. Panel A of FIG. 19 is a representative panel of FISH labeling for transcripts enriched in RBCs. Colocalization is shown using IHC for the RBC marker PKCα. Panel B of FIG. 19 shows higher magnification view of labeling for low abundance transcripts. Panel C of FIG. 19 is a heat map showing relative expression value (normalized by row) for RBC-enriched transcripts in other retinal cell types in the previous whole retina dataset (Macosko et al., 2013). Enriched transcripts detected in other cell types were consistent with the types of non-RBC cells labeled in the panel of Panel A of FIG. 19. Scale bars, 20 µm (Panel A of FIG. 19) and 10 µm (Panel B of FIG. 19).
Figure 19:
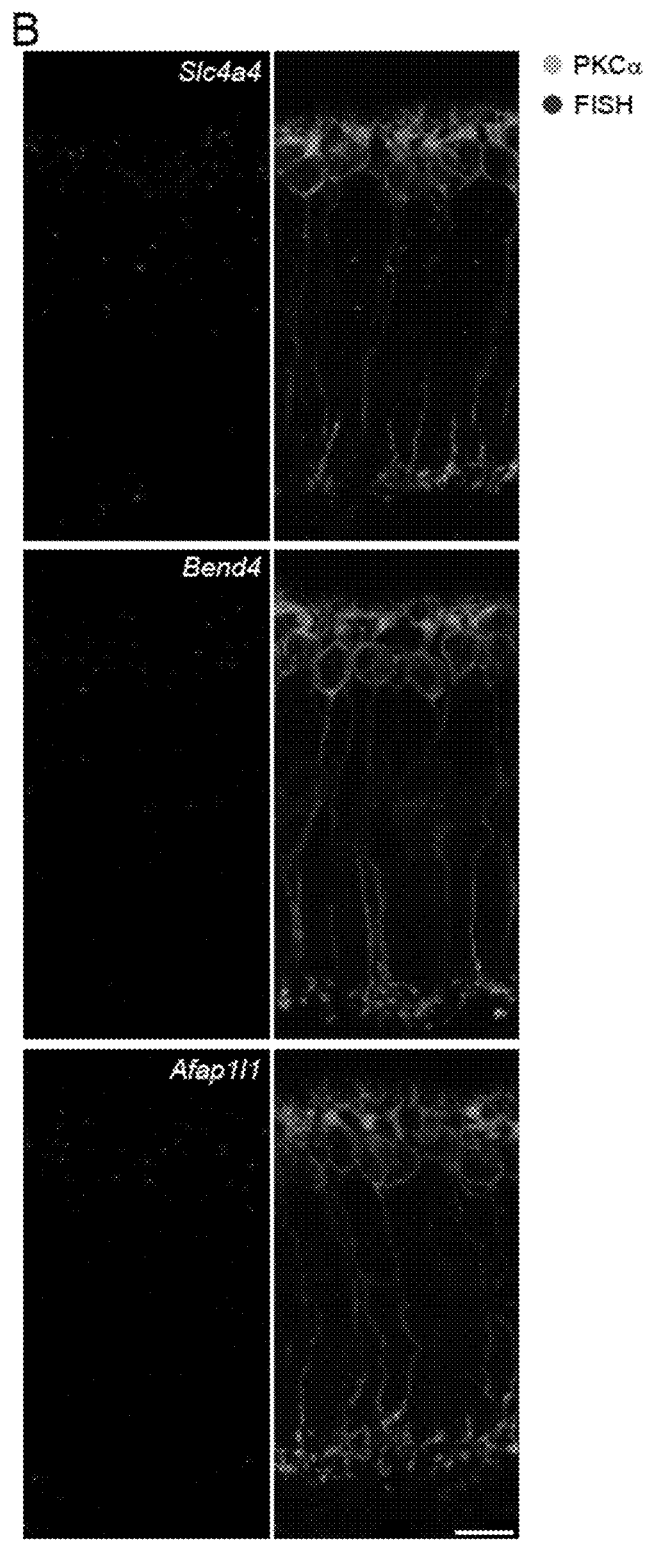
Figure 19:
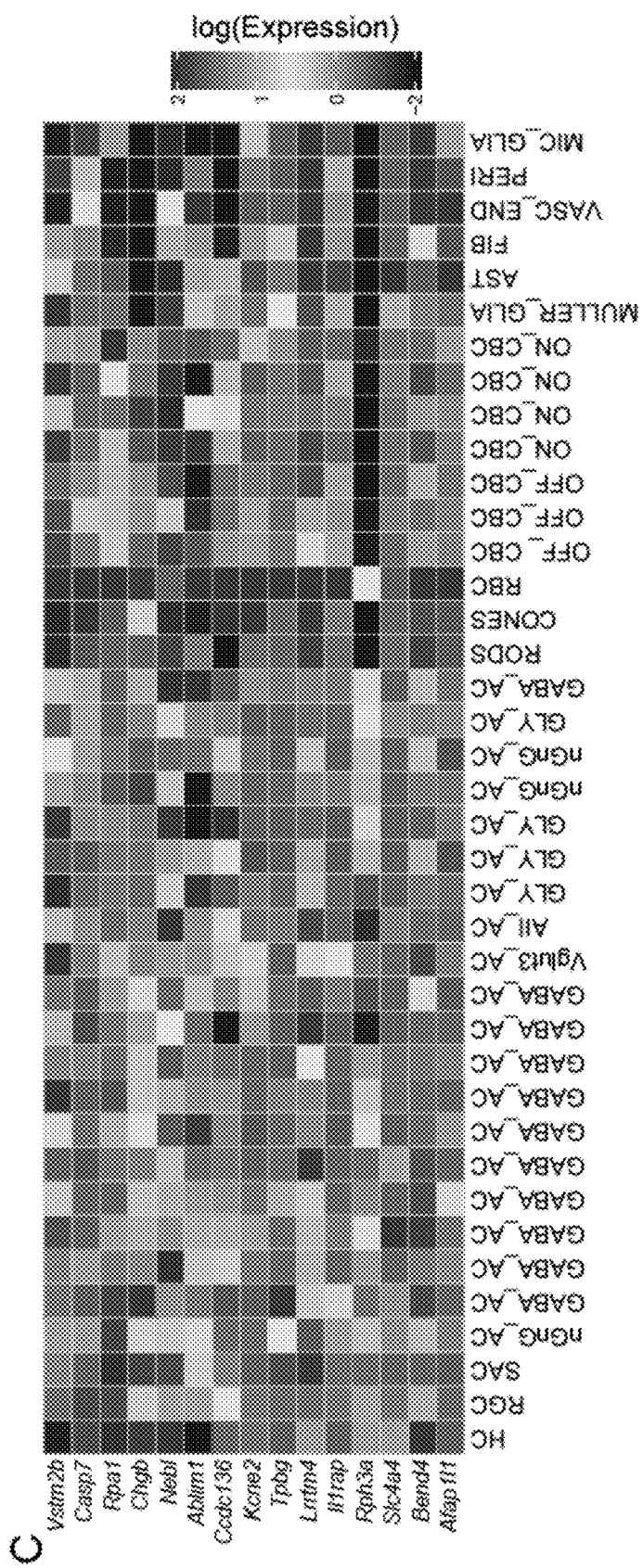
Figure 20:
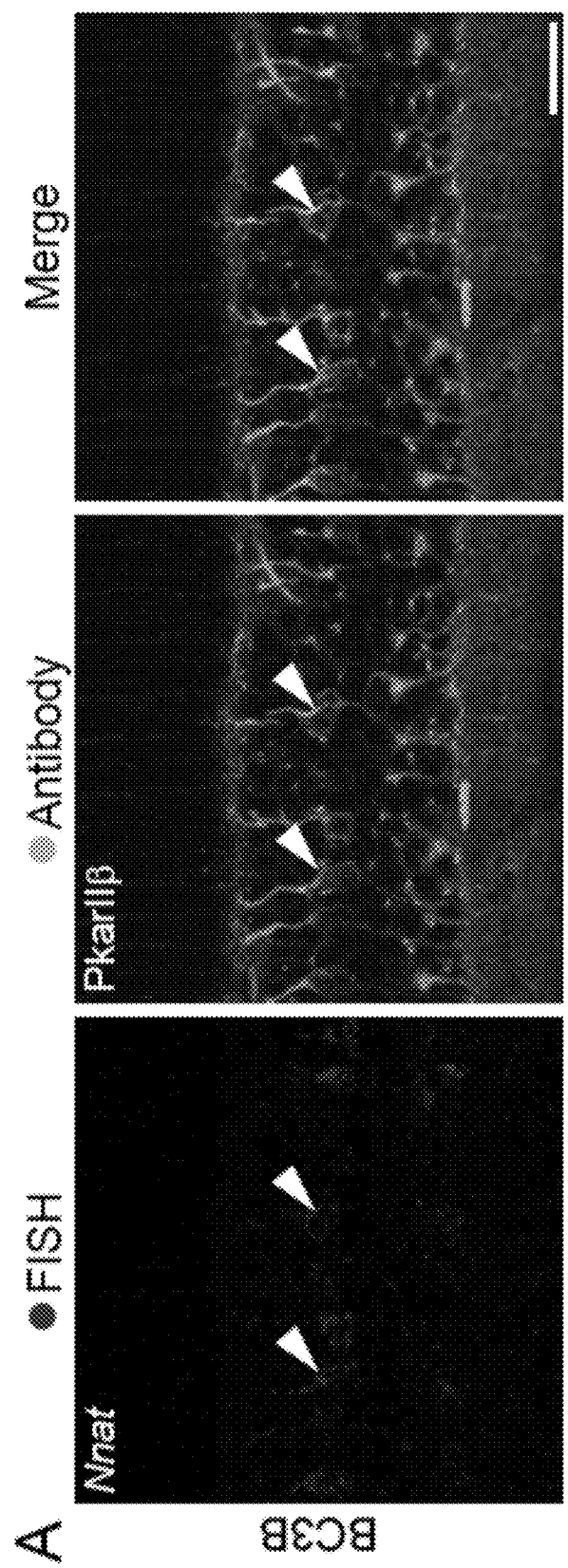
FIG. 20 depicts a validation of genes marking BC3A, 3B, 4, 6, and 7 plus BC2 known marker expression, related to FIGS. 8-10. Panel A of FIG. 20 shows that Nnat is expressed in cells labeled by the BC3B marker PkarIIB. Panels B-C of FIG. 20 depict that Cabp5 is coexpressed with Erbb4 (BC3A marker), but not with Col11a1 (BC4 marker), consistent with Cabp5 expression patterns in these types (FIG. 6). Panel D of FIG. 20 shows that Igfn1 is expressed in cells labeled by the Gustducin-GFP transgenic mouse line, known to brightly label BC7. Panel E of FIG. 20 depicts injection of cre-dependent AAV-stop-YFP into a Cck-cre mouse line labels S5 laminating cells that are positive for Syt2, a marker of BC6 axon terminals, in addition to BC2 cells. Panel F of FIG. 20 shows expression of previously described BC2 markers. Representation as in FIG. 6. Scale bars 20 µm.
Figure 20:
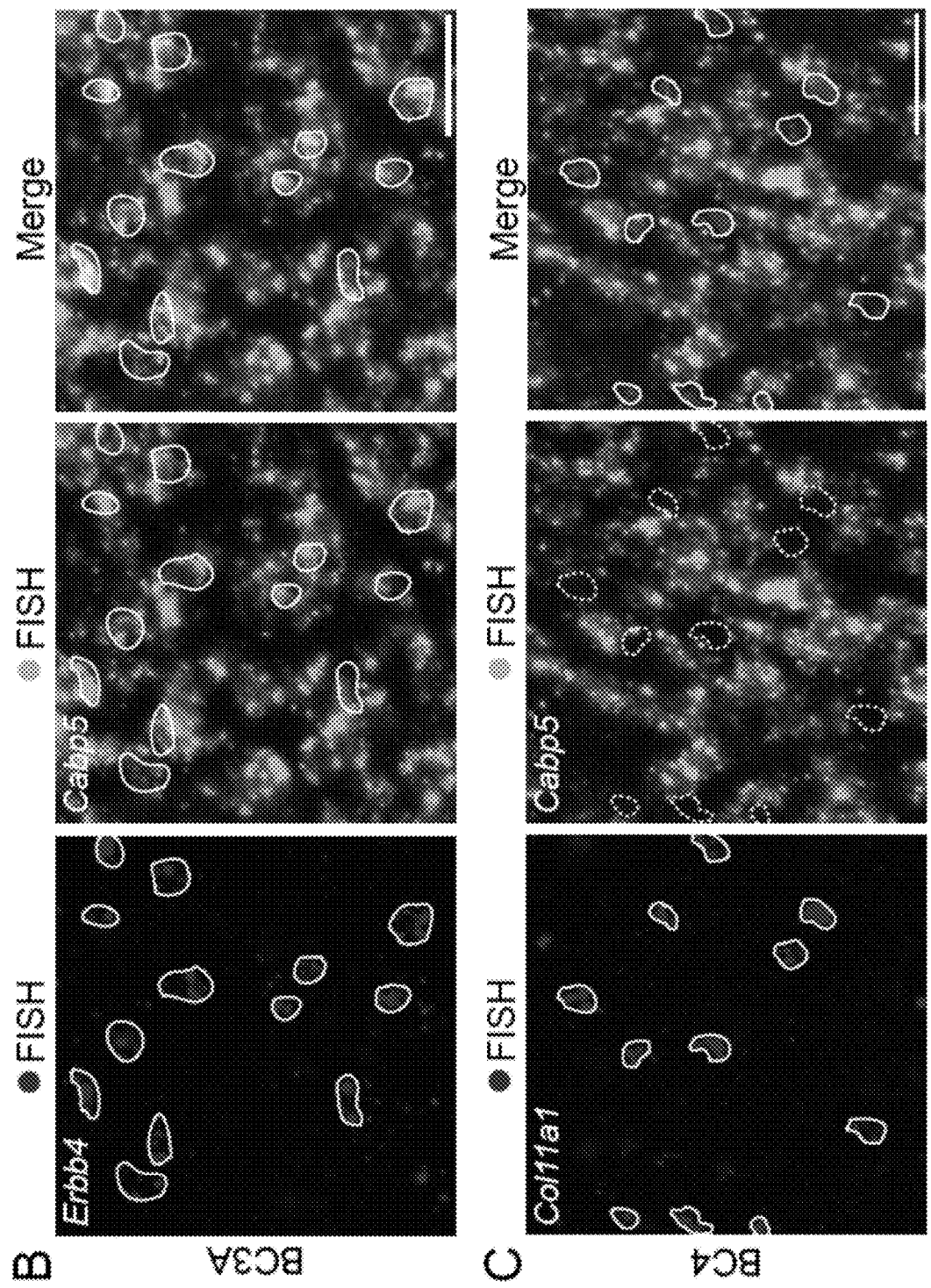
Figure 20:
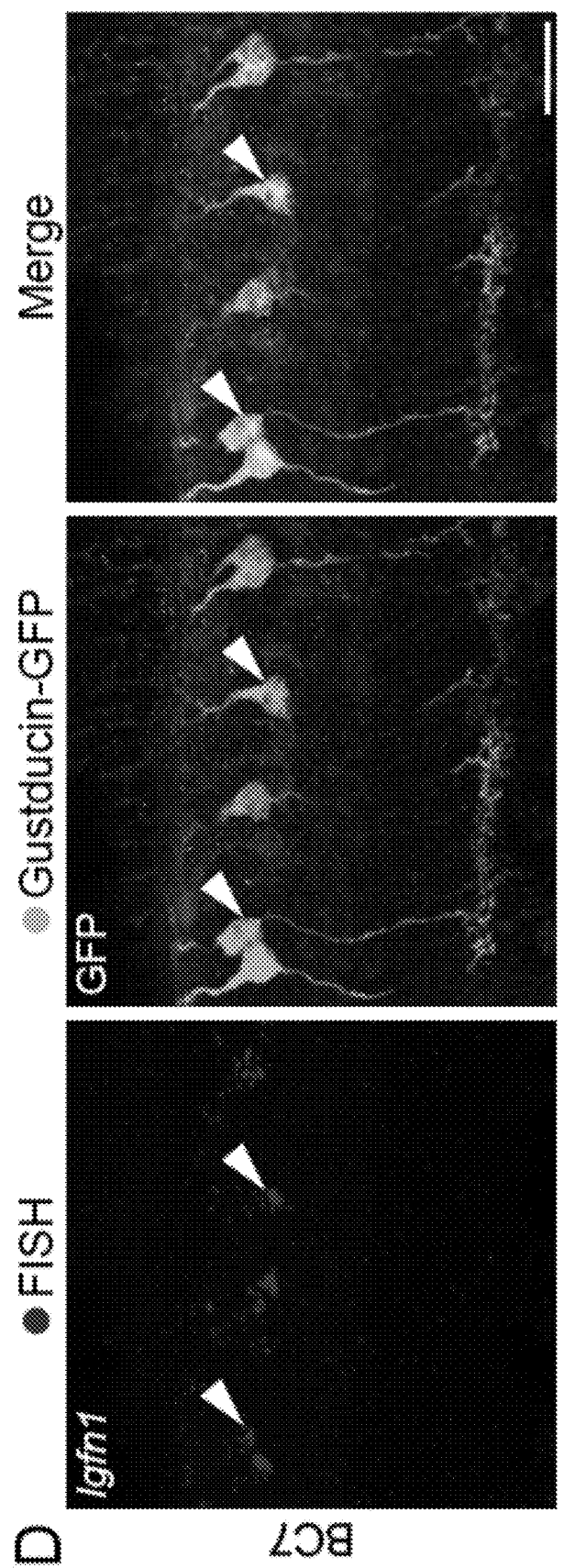
Figure 20:
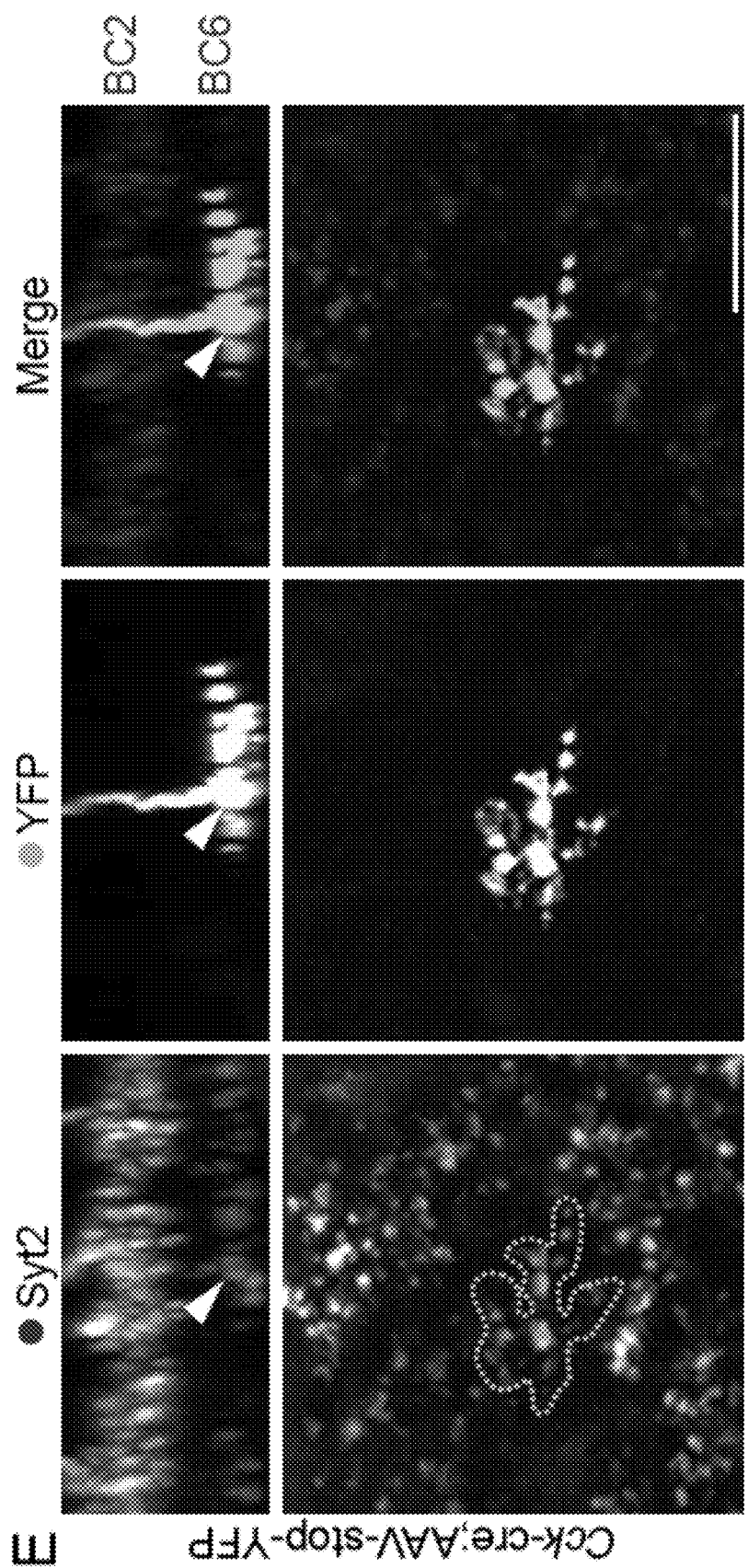

To identify molecular markers for BC types, a binomial test was devised to find differentially expressed genes for each of the corresponding clusters (FIG. 8, Panel G of FIG. 18). To validate predicted markers against cellular morphology, a method for sparse labeling of BCs using a lentivirus with a Vsx2 enhancer to express GFP preferentially in BCs was developed, and combined with fluorescent in situ hybridization (FISH). Additionally, for cell types where another marker was already known, FISH was combined with a specific antibody, double FISH, or a transgenic reporter mouse line. More than 100 genes were identified enriched in the RBC cluster over all other BC types (FDR <0.01). They included all previously reported RBC markers and numerous novel candidates. The expression of 25 candidate genes from this list were validated using FISH in combination with an RBC-specific antibody, PKCα, and found overlap for all 25; multiple examples are shown in Panels B-D of FIG. 9 and Panel A of FIG. 11). The expression of several low abundance genes was also validated, which were selectively expressed by RBCs but detected in <30% of the cells in this cluster (Panels A-C of FIG. 19). These results indicate that despite the low coverage per single-cell library, the ability to sample a large number of cells across multiple types provides sufficient statistical power to accurately identify strongly enriched markers across a wide range of expression levels. Also novel markers for BC types 3A, 3B, 4, 6 and 7 were validated (FIGS. 6 and 8). The morphology of FISH-positive cells revealed by sparse lentiviral labeling was matched to reconstructions from electron microscopy (Helmstaedter et al., 2013) (FIG. 2E-2I, leftmost panels). The inner plexiform layer (IPL), where BC axon terminals ramify, can be divided into five distinct sub-laminae (S1-5) with S1 being closest to the inner nuclear layer (INL), and S5 being closest to the retinal ganglion cell layer (GCL) (FIG. 1). Erbb4, Nnat, Col11a1, Lect1, and Igfn1 labeled cells that corresponded in arbor shape and lamination with BC3A, 3B, 4, 6, and 7 respectively (FIG. 10, middle panels). Further markers for all five types were validated by combinatorial labeling with known markers and use of transgenic lines (Gustducin-GFP and Cck-cre; Panels A-E of FIG. 20). Additional markers for BC2 were not validated, because this type already has many validated markers (Chow et al., 2004; Feng et al., 2006; Fox and Sanes, 2007; Haverkamp et al., 2003; Jin et al., 2010), all of which were enriched in cluster 10 (Panel F of FIG. 20). To facilitate analysis of markers throughout the retina, a modified FISH procedure was devised to examine the distribution of marked cells in retinal whole mounts. This method revealed that the selected markers gave specific patterns of labeled somata across the whole retina, as expected for authentic neuronal types (FIG. 10, rightmost panels). Together, these results identify gene expression patterns of, and validate new markers for six cell types. The remaining seven BC clusters were less readily assigned to known types.

FISH was performed with DIG-labeled or DNP-labeled antisense riboprobes, detected using anti-DIG-HRP or anti-DNP-HRP followed by tyramide amplification, as described (Trimarchi et al., 2007), with some modifications. For FISH on virus-labeled sections, GFP was detected with anti-GFP antibody after probe detection. For whole mount FISH, permeabilization was increased using a freeze/thaw cycle and by elevating proteinase K and detergent concentrations. Immunohistochemical labeling was performed as described in (Duan et al., 2014) and (Krishnaswamy et al., 2015).

Example 6: A New BC1 Variant with Amacrine-Like Morphology

Figure 21:
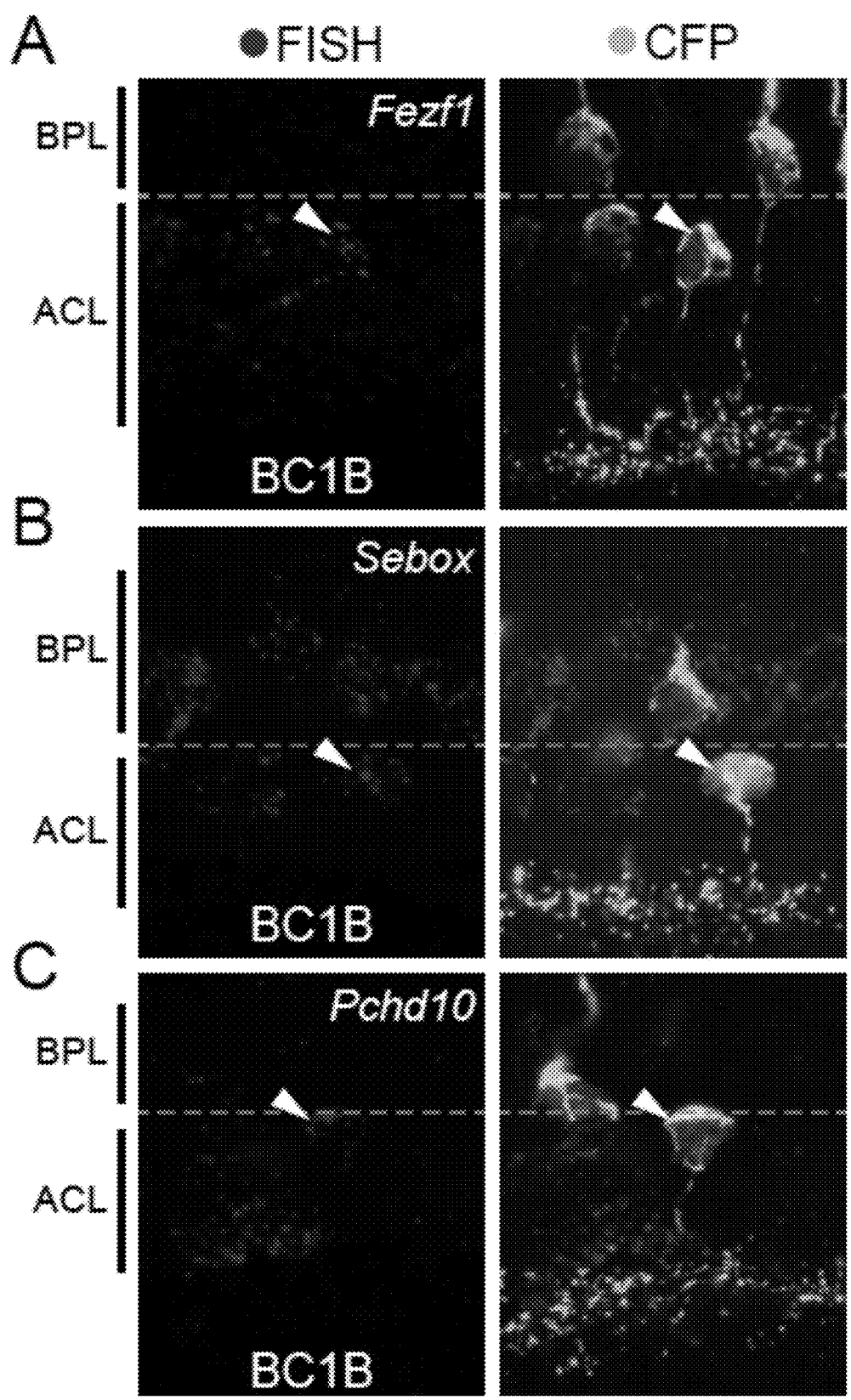
FIG. 21 shows validation of genes marking BC1A and BC1B, morphological transition of BC1B during development, and BC1B markers in mature adult retina, related to FIG. 11. Panels A-F of FIG. 21 depicts FISH labeling of additional markers for BC1A and BC1B. Staining is of P17 tissue from the MitoP-CFP line, with CFP detected using anti-GFP antibody. Panel G of FIG. 21 depicts that Fezf1-cre crossed to a tdTomato cre-reporter mouse line labels BC1B cells, as determined by morphology and IHC for Vsx2. Panel H of FIG. 21 shows that most cells lacking an upward process at P8 are predominantly nGnG amacrine cells (Ppp1r17+, Vsx2-). Panel I of FIG. 21 depicts the BC1B (and BC2) marker Nxph1 labels MitoP-CFP+ cells with an upward process at P8. Panels J-L of FIG. 21 show that the unipolar population persists until at least P100, as assayed by IHC staining for (Panel J of FIG. 21) Otx2, (Panel K of FIG. 21) FISH for Nxph1, (Panel L of FIG. 21) and IHC for Lhx3 and Vsx2. Scale bars indicate 20 µm for main panels and 10 µm for insets.
Figure 21:
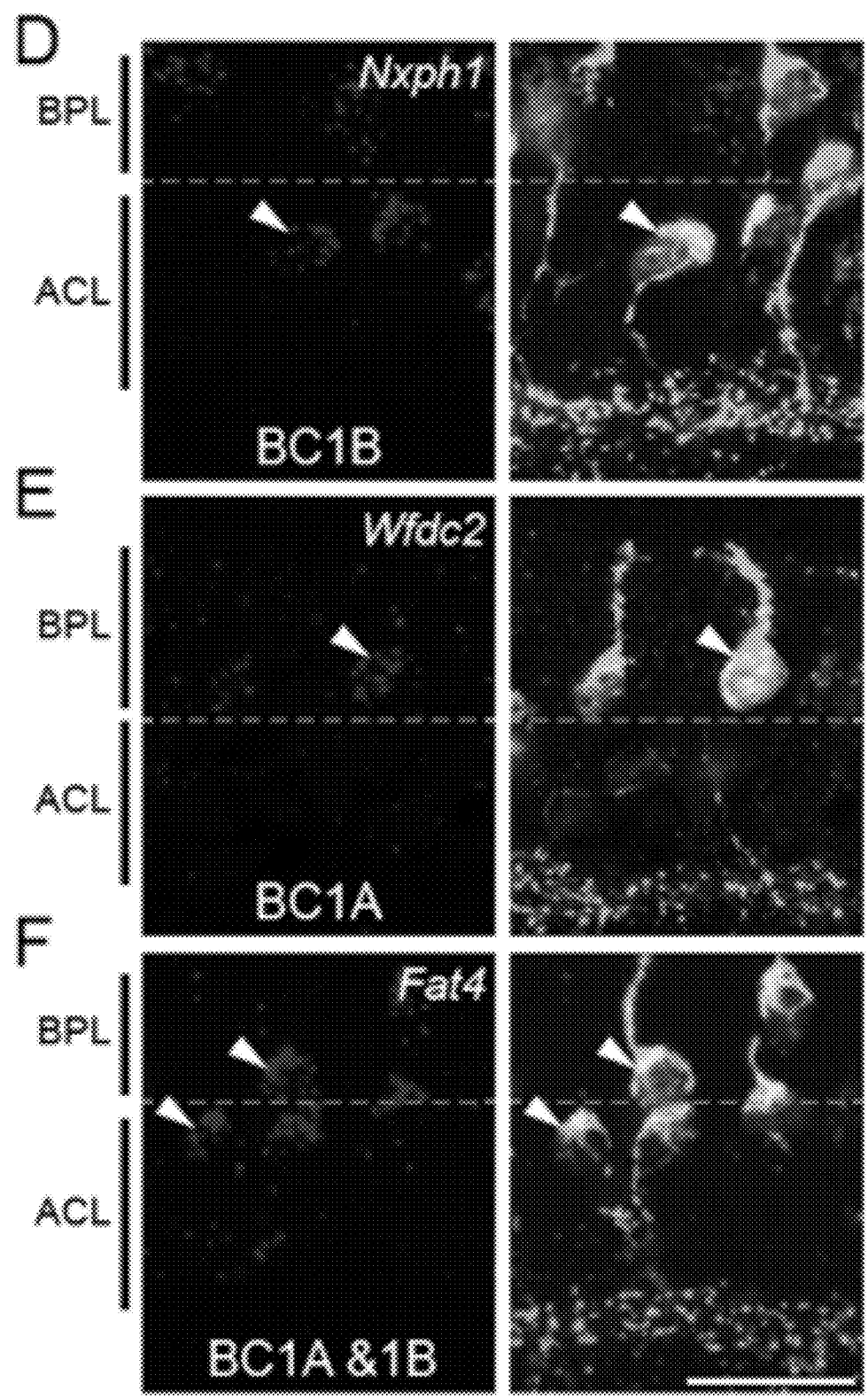
Figure 21:
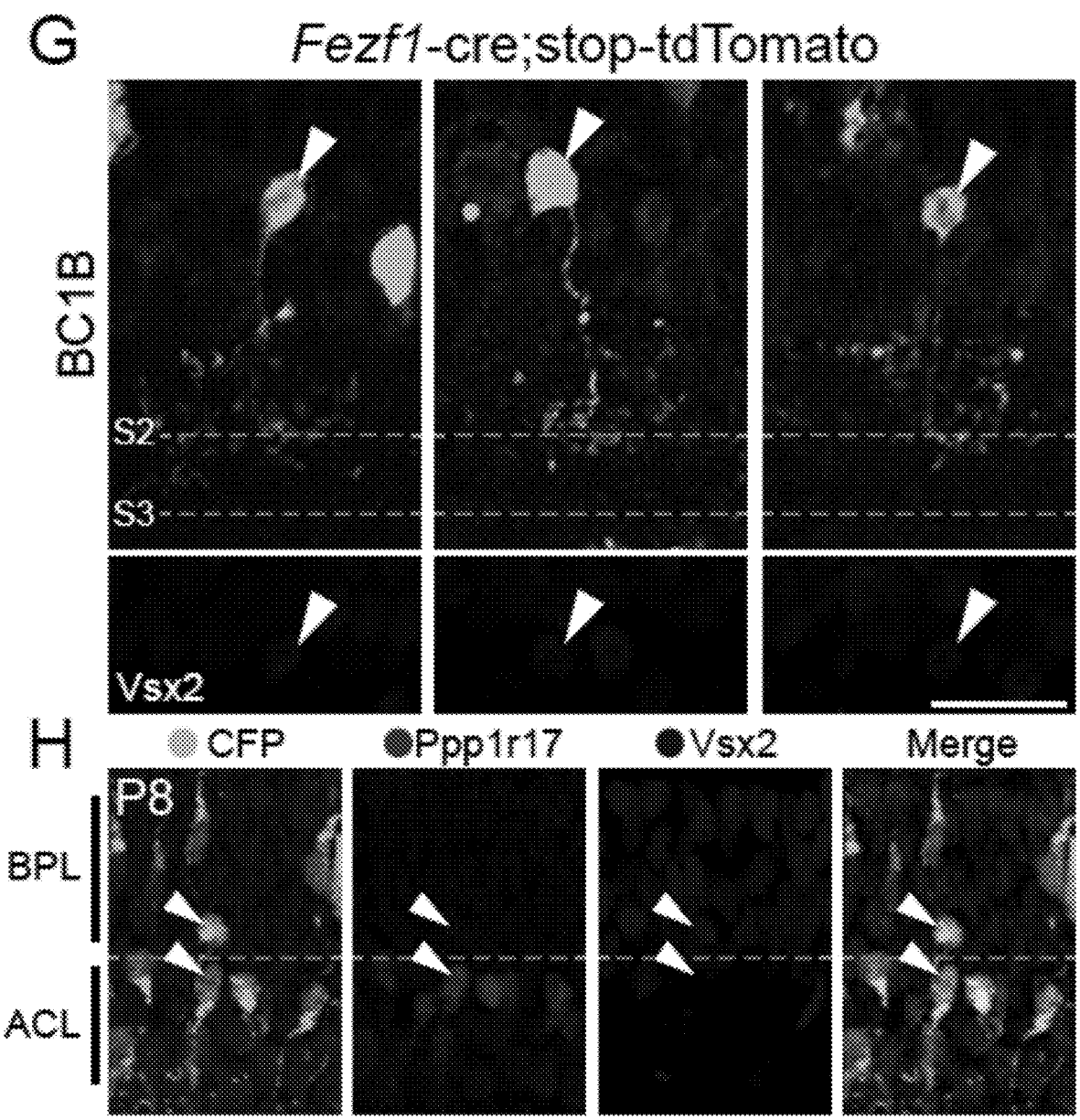
Figure 21:
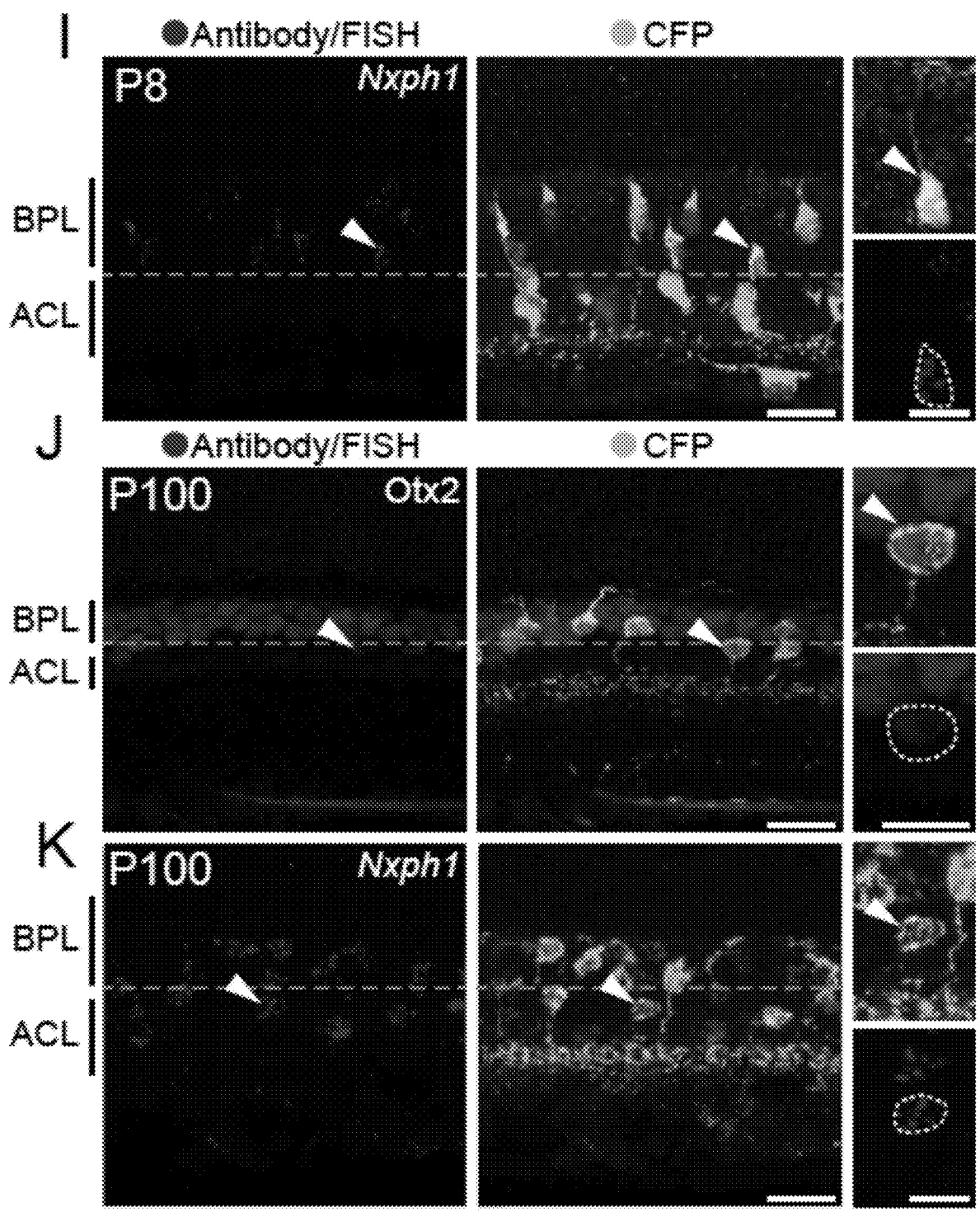
Figure 21:
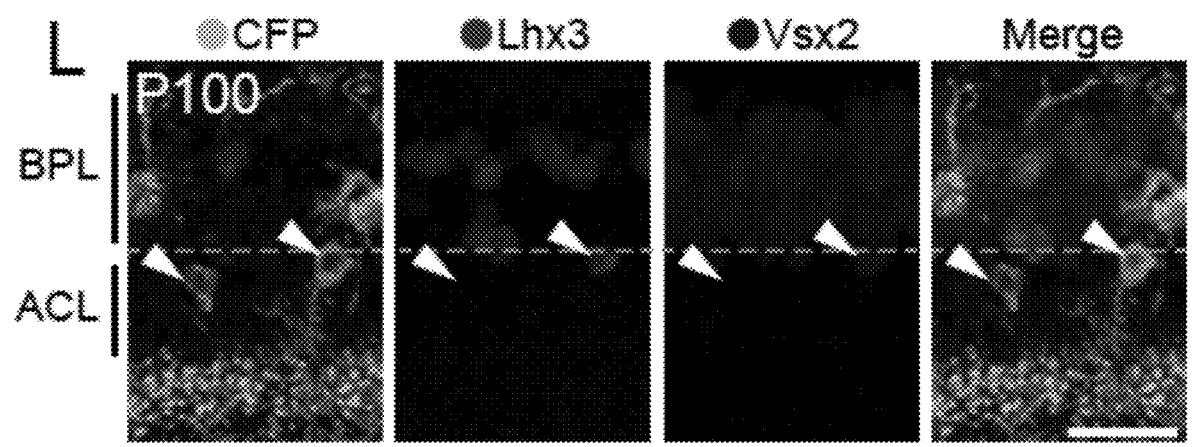

Two clusters (7 and 9) had gene expression signatures characteristic of BC1 (Tacr3+, Rcvrn−, Syt2−). It is referred to them as BC1A and BC1B. This was unexpected as immunohistochemical and electron microscopic studies had previously indicated BC1 to be a single population (Helmstaedter et al., 2013; Wassle et al., 2009). Although BC1A and BC1B were each other's closest relatives (FIG. 7), 139 genes were >2 fold differentially expressed between them (FDR <0.01), suggesting that they represented distinct cell types. Intriguing differences between the clusters included the recognition molecule Pcdh17 and the transcription factor Fezf2 enriched in BC1A, and Pcdh10 and Fezf1 enriched in BC1B (Panel A of FIG. 11). To explore whether BC1A and 1B were morphologically as well as molecularly distinct, the MitoP transgenic line was used, in which CFP is expressed under control of regulatory elements from the Thy1 gene. In this line, CFP is expressed in BC1s and in an amacrine cell type called nGnG (Kay et al., 2011; Schubert et al., 2008). As is the case for other Thy1 lines (Feng et al., 2000; Kim et al., 2010), expression patterns do not reflect those of Thy1, but presumably result from effects of the transgene insertion site. FISH revealed that BC1A and BC1B markers were expressed by CFP-positive cells with distinct shapes and positions (Panel B of FIG. 21 and Panels A-F of FIG. 21). BC1A markers labeled cells with conventional bipolar morphology. Surprisingly, BC1B markers labeled cells that were unipolar, lacking a dendrite extending to the outer plexiform layer (OPL), in which BCs receive synaptic input from photoreceptors. Moreover, the positions of the BC1A and BC1B cell bodies were different: BC1A somata were intermingled with other BCs near the OPL border, whereas BC1B somata were located closer to the IPL, where amacrine cell bodies are positioned. Gene expression data confirmed the bipolar identity of BC1B cells, as they expressed pan-BC markers, but neither pan-amacrine markers nor the nGnG amacrine marker Ppp1r17 (FIG. 6, Panels A and C of FIG. 11). Two additional experiments confirmed the unusual morphology of BC1B cells. First, lentivirus combined with Vsx2 immunolabeling demonstrated the lack of an apical process and revealed the elaboration of axonal arbors in S1 of the IPL, where BC1A and BC2 also arborize (Panels D and E of FIG. 11). Second, a mouse line was analysed in which cre was inserted into the endogenous locus of Fezf1, which is selectively expressed in BC1B (Panel A of FIG. 11). When crossed to a Cre-dependent reporter, this line labeled Vsx2+ unipolar cells with BC1B morphology and lamination pattern (Panel G of FIG. 21). Moreover, L. Della Santina and R. O. Wong (personal communication) have recently observed cells that likely correspond to BC1B in another transgenic line, and confirmed that their synaptic ultrastructure is characteristic of BC axon terminals. It is speculated that these unipolar cells were previously categorized as amacrine cells in EM reconstructions (Panel F of FIG. 11). As BC1B cells have bipolar-amacrine hybrid properties, we asked whether their developmental origins resembled those of amacrine cells or BCs. We used the MitoP line in combination with an antibody against Lhx3, which is expressed by BC1B but not BC1A cells (Panel A of FIG. 11). At P8, two sets of CFP+ cells in the outer part of the INL were observed, where all conventional BCs reside: some were Lhx3− Vsx2+(BC1A) and others were Lhx3+ Vsx2+(BC1B), but both had a bipolar morphology (Panel G of FIG. 11). The majority of CFP+ cells lacking an upward process at this age were nGnG amacrine cells (Panel H of FIG. 21). Intermediate BC1B cells transitioning from a bipolar to unipolar morphology were also observed at this age, positioned within the amacrine cell layer but with a short apical process not yet fully retracted (Panels G and H of FIG. 11). This result was confirmed using a second marker, Nxph1, which also distinguishes BC1A from BC1B (Panel I of FIG. 21). Thus, both BC1 types originate with a bipolar morphology, but BC1B cells lose their apical process and translocate to the amacrine layer (Panel H of FIG. 11). Notably, these unipolar cells are not a transient population, as they continue to express pan-bipolar and BC1B markers until at least P100 (Panels J-L of FIG. 21).

Example 7: Four Distinct BC5 Types

Figure 12:
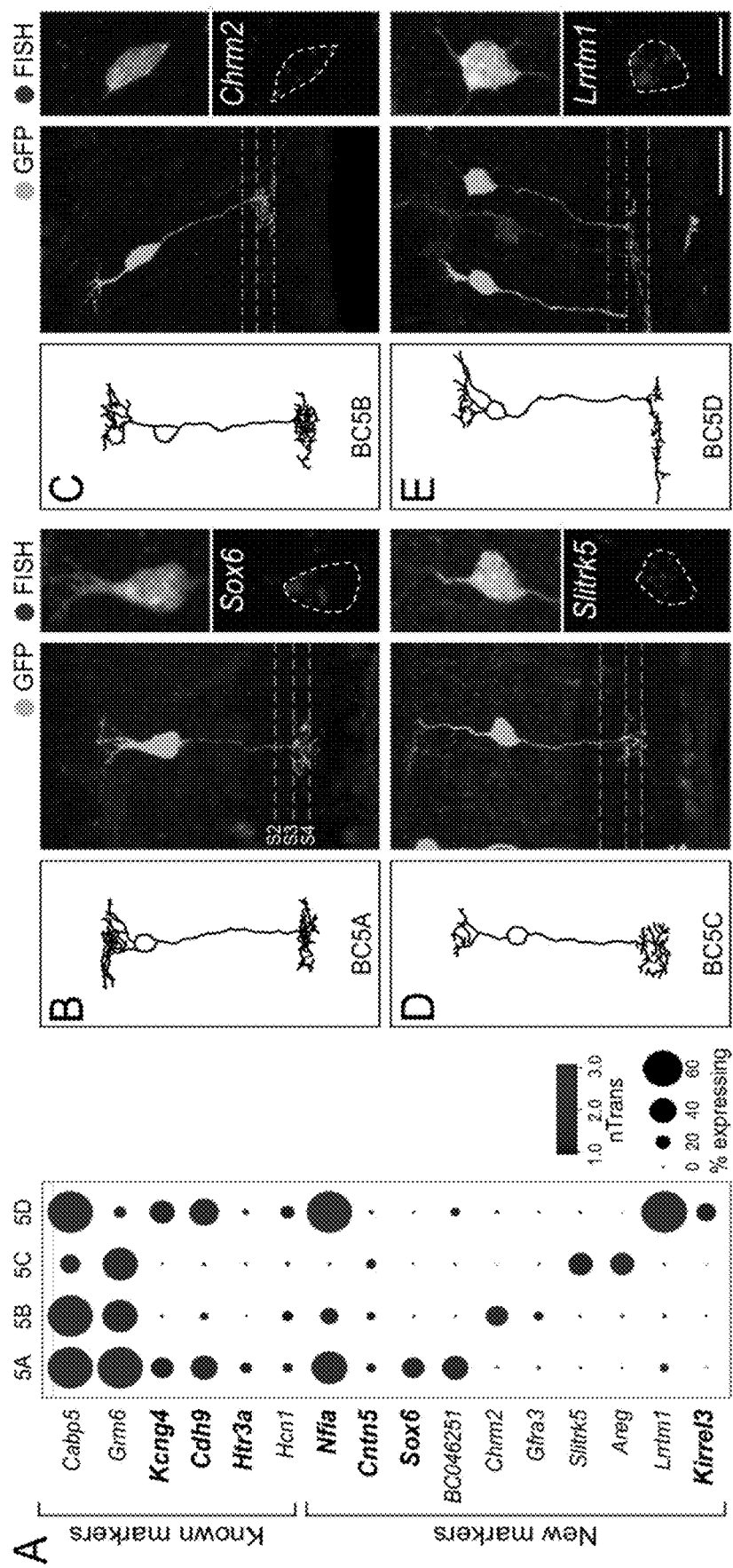
FIG. 12 shows four BC5 types with distinct morphology and gene expression. Panel A of FIG. 12 depicts expression patterns of known and novel BC5 genes across BC5A-BC5D clusters. Representation as shown in FIG. 6. Panels B-E of FIG. 12 show FISH+lentiviral labeling for BC5A-BC5D markers from Panel A of FIG. 12. Insets show localization of FISH within GFP+ cell body. Noise reduction applied to GFP+ lentivirus labeled cells as in FIGS. 8-10. Panels F-J of FIG. 12 show BC5 types labeled in transgenic lines that report on genes highlighted in Panels A-F of FIG. 12. Kcng4-cre; stop-YFP retina whole-mounts labeled with GFP and Sox6 show colocalization in BC5A cells (Panel G of FIG. 12G). Kcng4-cre; Cdh9-lacZ retinal cross section labeled for lacZ and cre show near complete co-localization (Panel H of FIG. 12). BC5D cells are GFP+ and PkarIIβ- in Kirrel3-GFP retinas. GFP-low and PkarIIβ+ cells correspond to BC3B Panel I of FIG. 12. Kcng4-cre; Htr3a-GFP retinal cross section labeled for GFP and cre show near complete co-localization (Panel J of FIG. 12). Kcng4-cre; stop-YFP; Cntn5-lacZ retinas labeled for YFP, lacZ, and Nfia combinatorially mark BC5A-5C. Panels K-L of FIG. 12 and FIG. 12 show that Kcng4-cre; Cntn5-lacZ retinas infected with AAV-stop-GFP marks BC5A (green and orange cells) and BC5D (cyan cell) that display morphology of these BC types. Terminals are shown from the side (left) and en face (right). Panel L of FIG. 12 depicts that GFP and lacZ labeling of axon stalks distinguishes BC5A (lacZ+) from BC5D (lacZ-). Dashed lines drawn from choline acetyltransferase (ChAT) labeling of S2 and S4. Scale bars indicate 20 µm for main panels and 10 µm for insets. Panel M of FIG. 12 depicts that Bulk RNA-seq of FAC sorted Htr3a-GFP cells show BC5A and BC5D markers robustly expressed, but BC5B and BC5C markers are absent.
Figure 12:
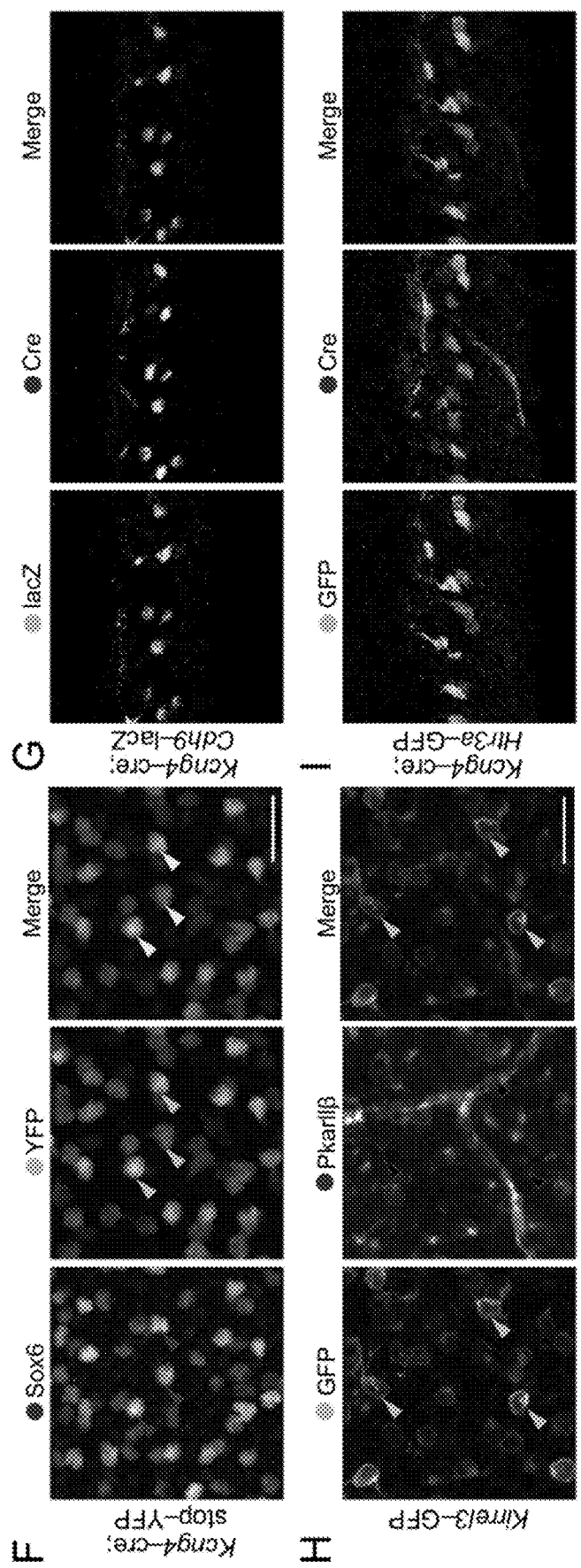
Figure 12:
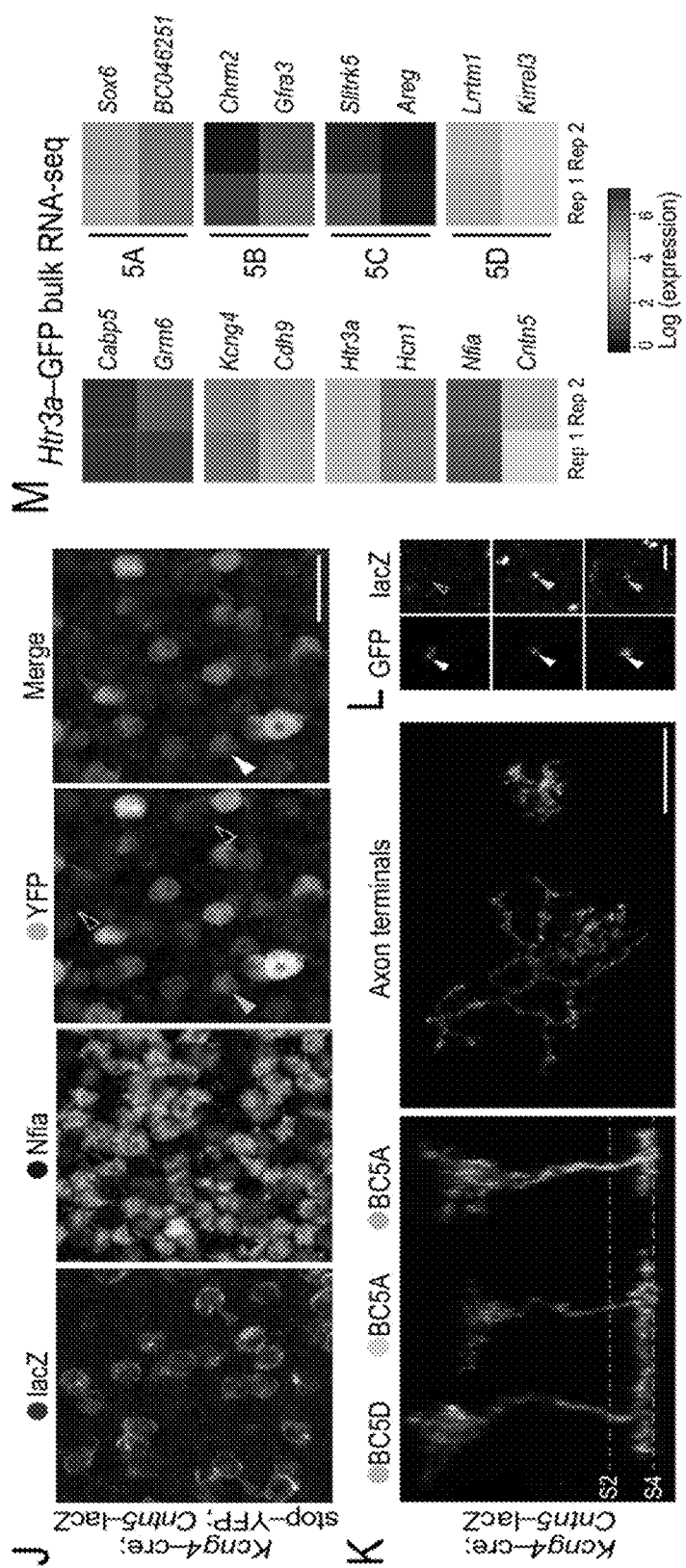

To date, molecular studies have revealed only a single BC5 type in mice (Wassle et al., 2009), but morphological and physiological analyses have shown the existence of two BC5-like populations and an additional type, provisionally called XBC, that laminates in proximity to BC5 (Euler et al., 2014; Hellmer et al., 2016; Helmstaedter et al., 2013; Ichinose et al., 2014). A transcriptomic analysis revealed the presence of four prospective BC5 clusters (FIG. 7), which were termed BC5A-D, as they were closely related to each other; each expressed one or more markers known to be expressed in BC5 cells (FIG. 4A) (Duan et al., 2014; Haverkamp et al., 2003; Hellmer et al., 2016; Wassle et al., 2009). Using the lentivirus/FISH method, it was found that BC5A-D axons all arborized between S3 and S4, characteristic of canonical BC5s, but displayed morphological distinctions (Panels B-E of FIG. 12). Cells labeled by the BC5A marker, Sox6, and the BC5B marker, Chrm2, had similar axonal arbors, but only the former extended large dendritic stalks to the OPL, a feature consistent with the ultrastructurally defined type 5A. Slitrk5, a marker for BC5C, labeled cells with bistratified axons. Finally, the BC5D marker Lrrtm1 localized to cells with wide, thin arbors consistent with those of XBCs (Helmstaedter et al., 2013). To gain further insight into the diversity of BC5s, five transgenic or knock-in lines were analyzed that report on the expression of genes enriched in specific BC5 types (Panel A of FIG. 12). In each case results validated patterns predicted from Dropseq. (1) Retinas from the Kcng4-cre; stop-YFP line immunostained with an antibody to Sox6 revealed a large double-labeled population (Panel F of FIG. 12), consistent with co-expression of Kcng4 and Sox6 in BC5A (Panel A of FIG. 12). (2) In retinas from a Kirrel3-GFP line, a sparse population of GFP-positive cells was observed that had a mosaic-like spacing with an exclusion zone of 17.6 greater than the cell soma size of about 8 and a density of 1,001 cells/mm2 (±34 SEM), consistent with a single sparse type with a wide arbor. This density and spacing are characteristic of BC5D, the only BC5 type that expresses Kirrel3 (Panels A and H of FIG. 12). (3) Cntn5 was expressed in BC5A-C. Each of these types were distinguished using Cntn5-tau-lacZ; Kcng4-cre; stop-YFP triple transgenic mice and then immunolabeled for antibodies to lacZ, YFP and Nfia, the latter being expressed in BC5A, B and D (Panels A and J of FIG. 12): BC5A was lacZ+ YFP+ Nfia+, BC5B was lacZ+ YFP− Nfia+, and BC5C was lacZ+ YFP− Nfia− (Panel J of FIG. 12). (4) Infection of Kcng4-cre; Cntn5-tau-lacZ retinas with a Cre dependent reporter virus sparsely labeled BC5A (Kcng4+, Cntn5+) and BC5D (Kcng4+, Cntn5-) (Panels K and L of FIG. 12). (5) Cdh9 was expressed in the BC5A and BC5D clusters, and immunostaining in Kcng4-cre; Cdh9-lacZ retinas showed a near complete overlap (Panel G of FIG. 12); see also (Duan et al., 2014)). (6) Expression of Htr3a and Kcng4 in both BC5A and BC5D (Panel A of FIG. 12), was verified by immunostaining for Cre and GFP in Kcng4-Cre; Htr3a-GFP retinas (Panel I of FIG. 12), confirming results of Duan et al (2014). (7) Bulk RNA-seq of GFP-positive cells from the Htr3a-GFP line confirmed the specific expression of predicted BC5A and BC5D but not BC5B or BC5C markers (FIG. 4M Panel M of FIG. 12). Together, these results provide a definitive division of BC5 into four groups, and a set of transgenic lines with which they can be marked.

For sparse labeling of BCs, lentiviral or AAV vectors we used. A FUGW (Lois et al., 2002) lentivirus genome plasmid was used as the backbone to insert an enhancer element upstream of the Vsx2 gene, shown in mouse to drive strong expression in bipolar cells (Emerson and Cepko, 2011). The element was placed upstream of an SV40 promoter followed by GFP. Concentrated lentivirus or cre-dependent Brainbow AAV (Cai et al., 2013) was injected subretinally into pups at P1.

Example 8: BC8 and 9 Identified Through an Alternative Unsupervised Method

Figure 13:
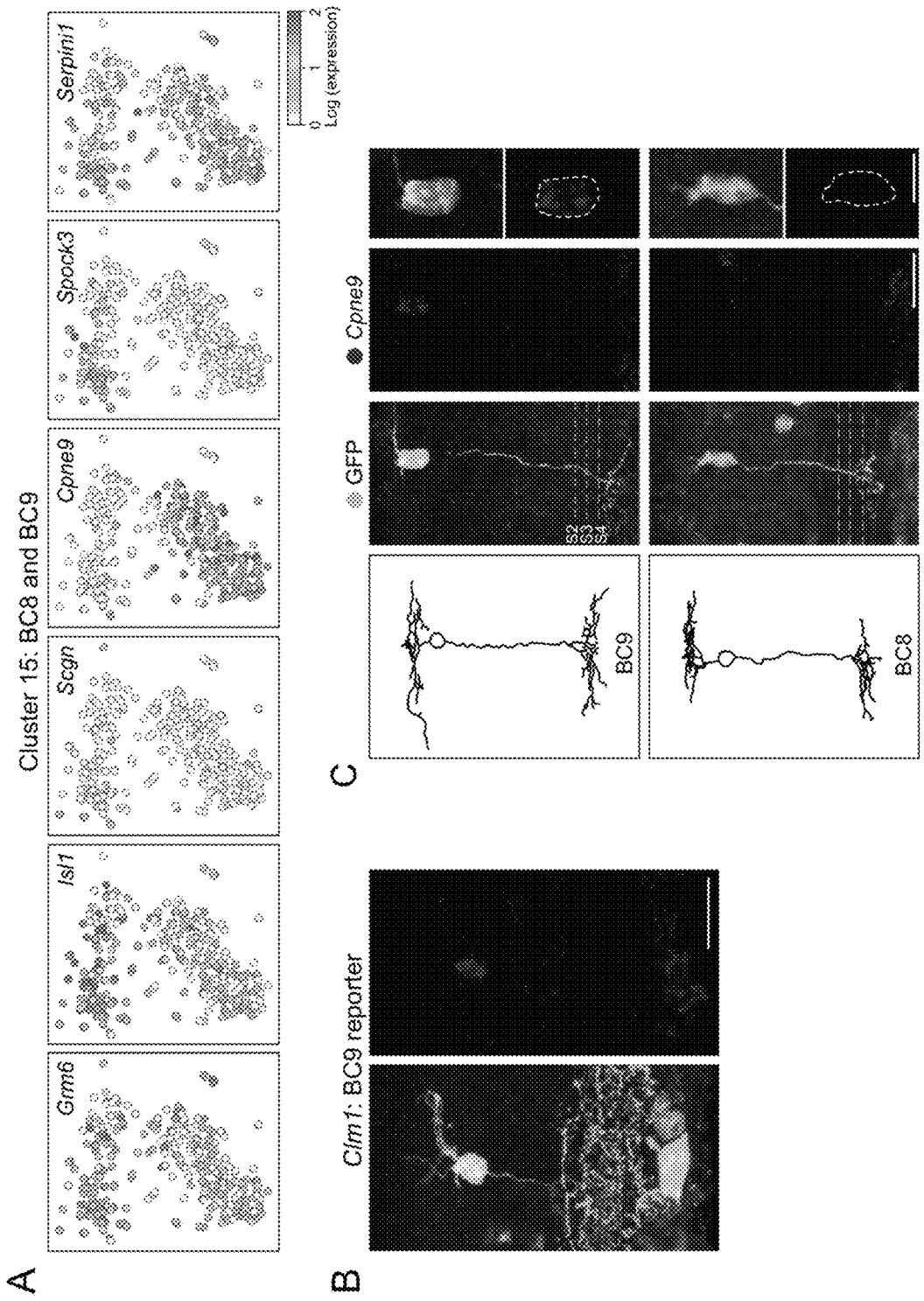
FIG. 13 depicts that BC8 and BC9 are closely related but separable by unsupervised methods. Panel A of FIG. 13A is a magnified view of cluster 15 on the tSNE map in Panel C of FIG. 3 which shows two subpopulations. Individual cells are colored by expression levels of ON cone BC genes (Grm6, Isl1, Scgn) and Cluster 15 enriched genes (Cpne9, Spock3, Serpini1). Panel B of FIG. 13 shows that BC9 cells labeled by the Clm-1 transgenic line are Cpne9+. Panel C of FIG. 13 shows that single cells labeled by lentivirus combined with FISH. Cpne9 is expressed in some but not all BCs with wide axonal arbors laminating at low IPL depth, consistent with the presence of two populations, BC9 (Cpne9+) and BC8 (Cpne9-). Insets show FISH and GFP labeling of the cell body. Noise reduction applied to GFP+ lentivirus labeled cells as in FIGS. 8-10. Panels D-E of FIG. 13 depicts that soma spacing in Cpne9 labeled retinal whole-mounts is indicative of Cpne9 marking a single type. Panel E of FIG. 13 shows a density recovery profile derived from whole-mount (Panel D of FIG. 13), revealing uniform spacing with an exclusion zone of 14.3 µm, which is absent in density matched simulations of randomly distributed, non-overlapping cells of similar size. Panel F of FIG. 13 shows that retinal whole-mounts with double FISH labeling for Cpne9 and Serpini1, reveals two populations, Cpne9+ Serpini1+(BC9, indicated by solid outlines) and Cpne9- Serpini1+(BC8, indicated by dashed outlines). Scale bars indicate 20 µm for main panels and 10 µm for insets.
Figure 13:
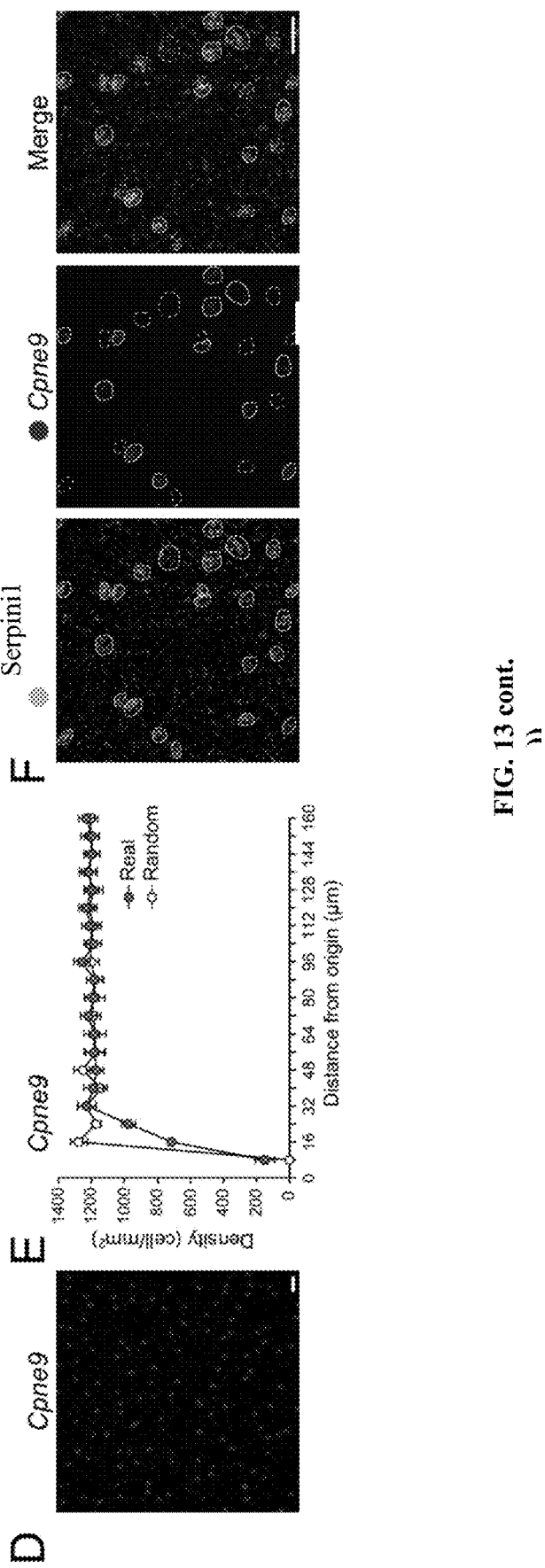

Cluster 15 expressed markers of ON cone BCs (Grm6+, Isl1+, and Prkca−), but no known markers of specific BC types (FIG. 6 and Panel A of FIG. 13). ON BC8 and 9 were the only known BC types that remained unaccounted for, and no endogenous markers of either type have been identified. It was therefore investigated whether this cluster contained either or both of these types. Close inspection of cluster 15 revealed two unique properties compared to the other 13 BC clusters. First, it exhibited a substructure, comprising two visibly separate groups of cells on the t-SNE map, suggesting the possibility of sub-populations (FIG. 3 and Panel A of FIG. 13). Second, although the Louvain-Jaccard algorithm identified it as a single cluster, the Infomap algorithm identified the two groups as distinct clusters (FIG. 4), even after merging of expression-proximal clusters. These clusters exhibited 71 differentially expressed genes (>2-fold expression difference FDR <0.01). Third, the most specific marker for this cluster, Cpne9, was expressed exclusively in one of the two putative sub-populations within cluster 15, while another marker, Spock3 (also expressed in BC6), was expressed in the other subpopulation (Panel A of FIG. 13). Neither Grm6 nor Isl1 exhibited this bias, suggesting both subpopulations consist of ON cone BCs. Fourth, the absence of Scgn from either subpopulation is consistent with their being BC8 and BC9, which have previously been described to be Scgn– (Euler et al., 2014; Puthussery et al., 2010). Taken together, these observations suggested that cluster 15 contains both BC8 and BC9, with Cpne9 marking one type and Spock3 the other. Serpini1, robustly enriched in cluster 15, was a shared marker of both types (FIG. 8 and Panel A of FIG. 13). To determine which subcluster corresponded to which BC type, the Thy1-Clomeleon-1 (Clm-1) line was used, previously described to specifically label BC9 cells (Breuninger et al., 2011; Haverkamp et al., 2005). Bipolar cells that expressed clomeleon (a GFP variant) also expressed Cpne9, indicating this to be a marker for BC9 (Panel B of FIG. 13). Cpne9+ BC9 cells using the FISH+lentiviral method were also identified; here, cells with BC8/9-like morphology that were Cpne9-, consistent with their being BC8 were additionally detected (Panel C of FIG. 13). Analysis of the spatial patterning of Cpne9+ somas in retinal whole mount revealed that the cells of this population exhibit an exclusion zone of 14.3 an average distance at which no other Cpne9+ cells are positioned (Panels D and E of FIG. 13). This minimum spacing distance between cells, greater than what could be determined by soma size alone, is consistent with this being a single cell type. Moreover, two-color FISH identified two populations of Serpini1+ cells, some of which were Cpne9+ (BC9) and others that were Cpne9– (BC8) (Panel F of FIG. 13). Based on these results, it was concluded that Serpini1+ Cpne9- and Serpini1+ Cpne9+ BCs would correspond to BC8 and 9, respectively. Taken together, the histological validation of a computationally derived molecular taxonomy unifies molecular signatures with morphological distinctions for BCs (Panels A and B of FIG. 14). More generally, these results serve as a proof-of-principle that large-scale, unbiased transcriptomic profiling at the single-cell level can enable robust classification of neuronal types in a heterogeneous class and discover novel types.

Figure 22:
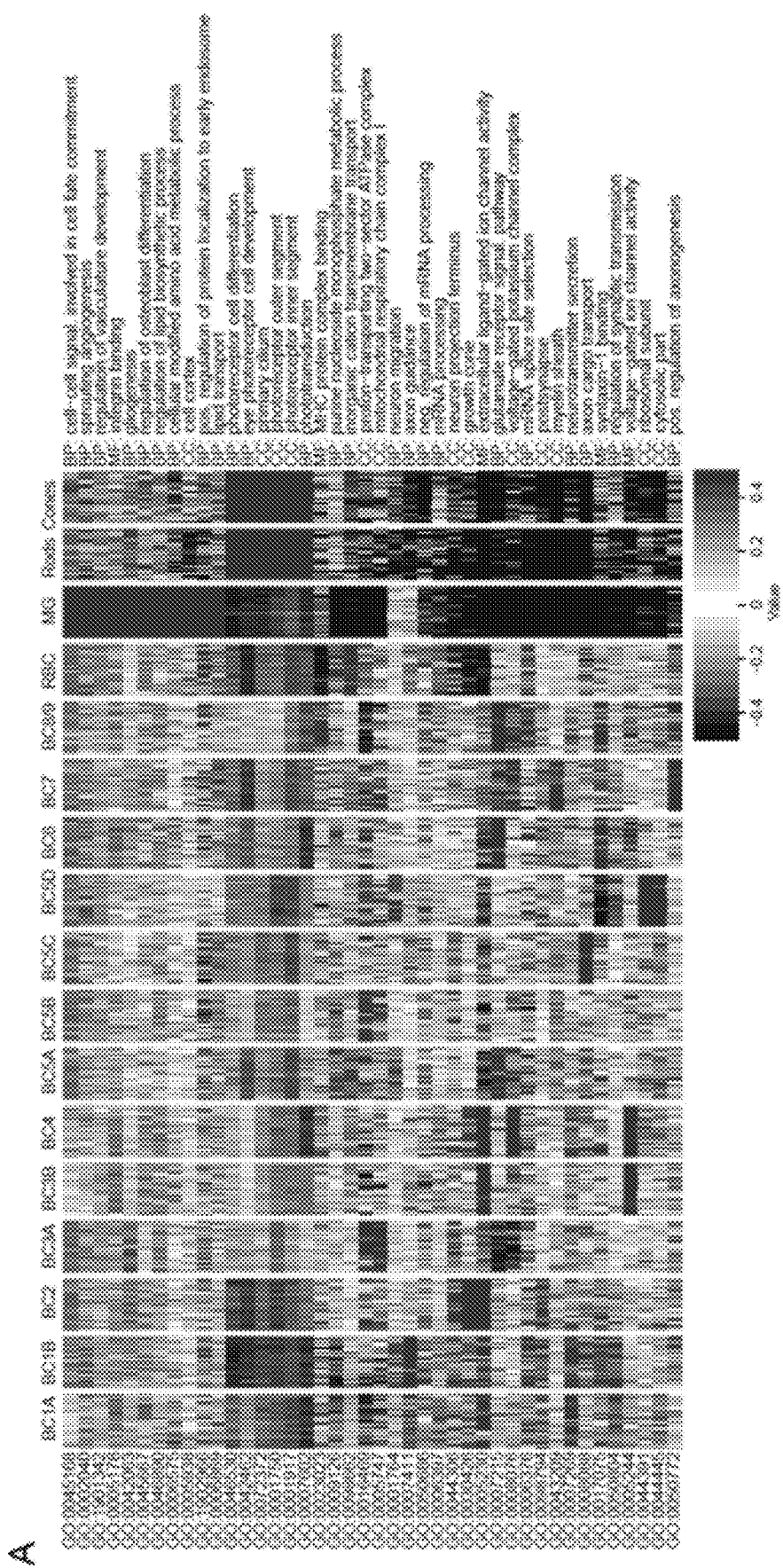
FIG. 22 shows an analysis of gene sets in BCs, related to FIG. 14. Panel A of FIG. 22 shows enriched GO-terms in BC, Müller glia, rod photoreceptors, and cone photoreceptors. GO category names and IDs are indicated as row names (Panels B-E of FIG. 22). FISH+lentiviral labeling for Grm6 in BC5A-D, note the lower expression of Grm6 in BC5D in Panel E of FIG. 22. Panel F of FIG. 22 depicts double FISH in retinal whole-mounts with the BC5D marker Lrrtm1 (red) and ON BC marker Grm6 (green) validates the low Grm6 expression in this putative ON BC type. Noise reduction applied to GFP+ lentivirus labeled cells as in FIGS. 8-10. Scale bars indicate 20 µm for main panels and 10 µm for insets.
Figure 22:
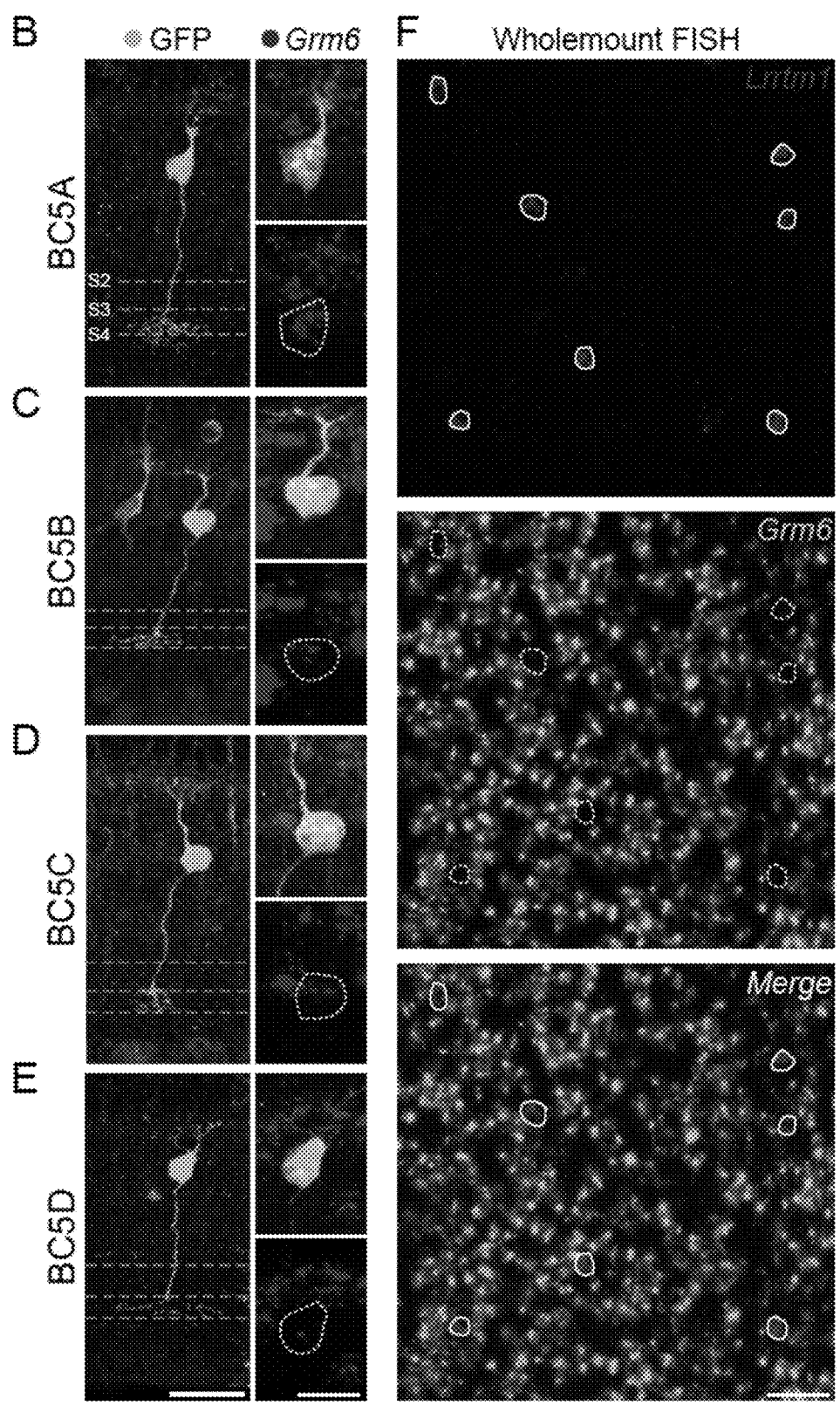

Example 9: Transcriptional Programs Underlie Functional Differences Among BC Types A primary motivation for transcriptionally profiling neuronal types within a class is to gain insight into functional or developmental differences among them. As a first step, the genes driving the top principal components for enriched functional categories as defined by Gene Ontology (GO) were tested (Wagner, 2015) (Panel C of FIG. 14). Top enriched categories in BC types included gene sets consistent with BC function and development ($p<10-6$, XL-minimum hypergeometric test), such as positive regulation of axonogenesis (GO:0050772)", "glutamate receptor signaling pathway (GO:0007215)", and "voltage-gated potassium channel complex (GO:0008076)" (as shown for example in Table 1 below). These categories exhibited modest differences among BC clusters, consistent with the common origin and function of these cell types. There were, however, notable exceptions: (1) "extracellular ligand-gated ion channel activity (GO:0005230)" was enriched in OFF cell types reflecting the usage of ionotropic glutamate receptors by these types; and (2) "neuron migration (GO:0001764)" was moderately enriched in BC1B, consistent with the translocation of this BC type from the bipolar cell layer to the amacrine cell layer. As expected, these categories differed substantially from those enriched in Müller glia and photoreceptors (Panel A of FIG. 22). These data are likely to be a rich source of information about BC development and function. Next expression of genes that encode neurotransmitters receptors were analysed (Panels D and E of FIG. 14). Patterns of glutamate and acetylcholine receptors were noteworthy.

Table 1 shows significant GO-PCA signatures.

Glutamate receptors: There are four main classes of synaptic glutamate receptors: NMDA (Grin1, 2a-d, 3a-b), AMPA (trial-4), and Kainate (Grik1-5), which are ionotropic (glutamate-gated channels) and metabotropic (Grm1-8; glutamate-activated G protein coupled receptors). All BCs respond to glutamate, which is released from photoreceptors in the dark. OFF BCs use ionotropic receptors that lead to depolarization by glutamate; thus, they hyperpolarize in response to illumination. A recent study reported that all OFF BCs are inhibited by a Grik-specific antagonist, indicating that they use Grik rather than Gria or Grin receptors (Borghuis et al., 2014). In contrast, ON BCs use the metabotropic receptor mGluR6 (Grm6), which leads to hyperpolarization by glutamate; thus, they depolarize in response to illumination. Patterns of glutamate receptors were generally consistent with this prior knowledge (FIG. 6D), but there were five exceptions. First, BC1A showed little, if any, Grik-class receptor expression. Thus, BC1A may use AMPA receptors, while BC2-4 may use predominately kainate receptors, consistent with recent studies (Ichinose and Hellmer, 2016; Puller et al., 2013). Second, the AMPA receptor Gria2 is expressed by all cone BC types, including BC1B, but not by RBCs. Non-canonical expression of ionotropic glutamate receptors in ON cone BCs has been observed previously in mammalian BCs, but the physiological role of these receptors has yet to be determined (Vardi et al., 1998). Third, although NMDA receptors have not been identified to play a role in glutamate response in BCs, Grin2b and 3a were detected in several BC types, albeit at low levels. Fourth, although all ON BCs expressed Grm6, expression was detected at much lower levels in BC5D, a result we confirmed by in situ hybridization (Panels B-F of FIG. 22). Thus BC5D may exhibit unconventional responses to light. Fifth, Trpm1, Gng13, and Nyx, which encode Grm6-associated proteins, are expressed not only by ON BCs but also by some OFF BCs (Panel D of FIG. 14).

Acetylcholine receptors: BC2 and BC3A provide direct input to the direction-selective circuit in the retina, synapsing with OFF starburst amacrine cells (SACs) and the OFF dendrites of ON-OFF direction-selective ganglion cells (ooDSGCs); BC5A and likely other BC5 types synapse on ON SACs and the ON dendrites of ooDSGCs (Duan et al., 2014; Helmstaedter et al., 2013; Kim et al., 2014). SACs are the sole source of acetylcholine (ACh) in the retina, but the role of ACh in the mature retina is not well understood (Taylor and Smith, 2012). BC2 and BC3A both express the nicotinic acetylcholine receptors Chrnb3 and Chrna6, and BC2 and BC5B express the muscarinic receptor Chrm2 (Panel E of FIG. 14). This pattern raises the possibility that SACs provide cholinergic feedback to the BCs that innervate them, and that the feedback from ON and OFF SACs is qualitatively different. The expression of potassium channels was analysed (Panel F of FIG. 14), based on evidence that variations in potassium currents across BC types underlie some of the differences in response properties (Ma et al., 2005). The Ca2+-activated K channel Kcnma1 was highly and broadly expressed, consistent with a previous report (Tanimoto et al., 2012). In contrast, several other K subunit types were expressed more selectively, including voltage-gated, inward rectifying G-protein activated, and pH-dependent, with varied expression patterns across BC types: Kcnab1, Kcnj9, and Kcnk3, respectively. Numerous transcription factors were differentially expressed across types, including factors expressed in single (Fezf1, Ebf1, Irx3) or small sets of types (Fezf2, Zfhx4, Vsx1, Six3, Nfib, Meis2, Nfia, Neurod2) (Panel G of FIG. 14). Some of these transcription factors have been reported to play roles in BC specification and/or maintenance (Cheng et al., 2005; Elshatory et al., 2007b; Feng et al., 2006; Jin et al., 2010; Star et al., 2012) but others remain to be studied. Aside from the previously described Isl1 (Elshatory et al., 2007a), factors whose expression correlates strictly with the ON/OFF division were not found. Nor were factors identified which were entirely specific to RBCs or other well-supported subdivisions of types in the dendrogram (e.g., BC5s, BC1A/1B). These complex patterns highlight the importance of combinatorial transcription factor codes in regulating type-specific gene expression. Finally, the expression pattern of adhesion/recognition molecules across types were investigated. Consistent with their role in establishing type-specific connections and lamination patterns, some of these genes showed expression in single types (Ptprt, C1ql3, Kirrel3, Tpbg) or small sets of types (Nxph1, Ntng1, Lsamp, Cdhr1). The cell surface receptor Amyloid beta. A4 protein (App) appears to be a robust pan-cone BC marker. Interestingly, genes from the same family typically had unique or non-overlapping expression patterns across types (Pcdh7, 9, 10, and 17, Ncam1 and 2, Slitrk5 and 6, Lrrtm1 and 3, Fam19a3 and 4, Cdh8, 9 and 11, and Cadm1-3) (Panel H of FIG. 14). A caveat is that profiling was done at P17, after major aspects of neuronal differentiation and circuit formation are complete; analysis at earlier time points would likely reveal additional, selectively expressed transcription factors and recognition molecules.

Example 10: Fewer, Deeply Sequenced Single-Cell Libraries do not Enable Better Classification Given limiting resources (time and money), it is important to achieve an optimal balance between the number of single-cell libraries sequenced and the sequencing depth per library. A primary advantage of Drop-seq (Macosko et al., 2015) and other massively parallel methods (Klein et al., 2015) is the ability to rapidly generate many single-cell libraries at a low per-library cost. Based on the previous experience with retinal classification (Macosko et al., 2015), the Drop-seq single-cell libraries were sequenced at a shallow depth of 8,200 mapped reads per cell. For the 27,499 cells analyzed in this study, this meant an "effective" combined library and sequencing cost of 34 cents per cell, accounting for the cost of low-quality libraries that were excluded from the analysis. To answer the question, if a better quality of classification had been reached if fewer cells were sequenced at a greater depth per cell for equivalent cost, GFP+ cells from the Vsx2-GFP line were collected in individual wells and 288 single cell libraries were prepared (3 retinae, 96 cells each) using Smart-seq2, a plate-based near full-length RNA-seq method (Picelli et al., 2014). In addition, bulk population controls consisting of about 10,000 GFP+ cells from each of the three retinae were collected with the single cells, and processed using Smart-seq2 (Panels A and B of FIG. 15). 229 single cells were analyzed that passed quality filters; they were sequenced to a median depth of 835,000 mapped reads per cell or ~100× deeper than Drop-seq cells; the cumulative depth of these 229 libraries (mapped reads) was equivalent to 23,300 Drop-seq libraries or approximately 83% of our dataset. However, the per-cell effective library+ sequencing cost of the Smart-seq2 cells was $18 (55× greater than Drop-seq), such that the overall cost of 229 single cells was equivalent to about 12,200 Drop-seq cells. Then Drop-seq and Smart-seq2 data sets were compared in several ways. Gene expression profiles averaged across the 229 Smart-seq2 single cell libraries were significantly correlated with average expression in cells profiled by Drop-seq (Pearson r=0.72; Panel C of FIG. 15), albeit weaker compared to their correlation with bulk libraries (Panel B of FIG. 15). Next, sensitivity of transcript detection was assessed by computing the fraction of cells where a transcript was detected as a function of the transcript's population expression level. As expected, the higher sequencing depth per cell in Smartseq2 enabled better detection of lowly expressed transcripts, compared to Drop-seq (Panel D of FIG. 15). To test whether this was related to sequencing depth or was a limitation intrinsic to Drop-seq, such as low transcript capture on beads, we re-sequenced about 200 single-cell libraries from one Drop-seq replicate at 50× greater depth (400,000 mapped reads per cell). Deeper sequencing greatly improved the transcript detection efficiency in Drop-seq libraries, and was comparable to Smart-seq2 libraries downsampled to a similar depth (Panel D of FIG. 15). Next the performance of fewer, deeply sequenced cells in cell type identification was examined. Clustering the 229 single cells using an approach similar to that used for the Drop-seq data generated 8 clusters (Panel E of FIG. 15). Clusters of RBCs, Müller glia and BCSA cells were easily distinguishable because of their numbers and transcriptional distinctiveness, but many other clusters expressed signatures of multiple BC types. We classified individual cells within these clusters using a random forest (RF) model (Panel E of FIG. 15, labels) trained on Drop-seq bipolar signatures (Panel D of FIG. 18). The predicted labels of individual cells showed that a majority of the mixed clusters were comprised of two bipolar types that were each other's closest relative (e.g. BC1A-1B, BC3B-4 and BC5B-5C). Importantly, none of the cells were classified as BC3A or BCSD cells, likely because these (1.7-1.9% in Drop-seq data) were not sampled in the dataset. In contrast, these type were identified in Drop-seq datasets containing 5000 shallow coverage cells (Panel N of FIG. 17 and Panel A of FIG. 18). These results suggest that a greater sequencing depth per cell is insufficient to compensate for the under representation of cell types, which forms a critical barrier in the ability to resolve distinct gene expression states. Next, using the finer cell-type labels assigned by the RF model, the top 30 differentially expressed genes for each BC type in the Smart-seq2 data were obtained using a bimodal test (McDavid et al., 2013). Nearly 60% of these markers had also been nominated as differentially expressed in the Drop-seq analysis (Panel F of FIG. 15), suggesting consistency between the results obtained from the Drop-seq and Smart-seq2 libraries. The proportion of gene discrepancies was larger for Smart-seq2 clusters with extremely small numbers of cells, suggesting that these might be false positives because of low statistical power. To determine whether our ability to cluster Smart-seq2 data was limited by numbers of cells, we collected YFP-positive BCs from retinas of Kcng4-Cre mice crossed to a stop-YFP Cre-dependent reporter, prepared 384 scRNA-Seq libraries using Smart-seq2, and analyzed the 309 libraries that passed quality filters. Unbiased clustering identified four large clusters in the data (Panel G of FIG. 15), and examination of top differentially expressed genes suggested that three of these clusters corresponded to BC5A (n=110), BC5D (n=60), and BC7 (n=43), consistent with Kcng4 expression (FIG. 6). A fourth cluster (n=82) consisted of likely rod-BC5 doublets. Also each cell was independently classified by the RF model trained on the Vsx2 Drop-seq clusters. Encouragingly, the predictions of the RF model were largely consistent with the cluster assignment for the majority of the cells in the BC5A, BC5D, and BC7 clusters (Panel G of FIG. 15 labels); as expected, the RF model failed to assign unequivocal classes for >90% of the cells in the rod-BC5 doublet cluster). Furthermore, consistent with Kcng4 expression in the Drop-seq dataset, none of the cells were classified as BC5B or BC5C, and genes that mark these BC5 types (Slitrk5 and Chrm2), were not appreciably detected in the data, while BC5A and BC5D markers were expressed (Panels H and I of FIG. 15). No other BC type, including rod BCs, were represented by >2 cells (Panel G of FIG. 15). These results demonstrate the importance of distributing a given number of reads over a large number of cells in order to accurately resolve cell type.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

We claim:
1. A method of identifying a cell or cell marker, comprising
 a) isolating target cells by label-free imaging flow cytometry;
 b) quantifying gene expression in the target cells by single cell sequencing,
  wherein sequenced transcript reads are obtained from RNA sequencing of 20,000 or more single cells from a biological sample, wherein the sequencing depth is about 10,000 or less reads per cell;
 c) clustering the target cells based on the gene expression by application of one or more algorithms;
 d) determining a transcription signature for each cluster based at least in part on identifying differentially expressed genes between two or more clusters and between each cluster and the remaining cells as background by applying an unsupervised machine-learning model; and
 e) validating gene expression against cellular morphology.

2. The method of claim 1, wherein the transcription signature identifies a bipolar cell type.

3. The method of claim 2, wherein the transcription signature identifies a rod bipolar cell, or one of the following cone bipolar cells: BC1A, BC1B, BC2, BC3A, BC3B, BC4, BC5A, BC5B, BC5C, BC5D (XBC), BC6, BC7, BC8, and BC9.

4. The method of claim 3, wherein the transcription signature identifies a bipolar cell and comprises at least one of Pcdh17, Pcdh10, Erbb4, Nnat, Col11a1, Sox6, Chrm2, Slitrk5, Lrrtm1, Cck, Lect1, Igfn1, Serpini1, Cpne9, Vstm2b, Casp7, Vsx1, Vsx2, Otx2, Scgn, Slc1a2, Slc6a9, Pax6, Tfap2a, Stx1b, Tacr3, Bhlhe23, Fat4, Fezf1, Fezf2, Wfdc2, Mylk, Hs3st2, Wls, Nxph1, Lhx3, Cabp5, Grm6, Kcng4, Cdh9, Htr3a, Hcn1, Hcn4, Nfia, Cntn5, BC046251, Gfra3, Areg, Kirrel3, Isl1, Spock3, Serpini1, Prkca, Car8, Sebox, Apoe, GluI, Aqp4, Cabp5, Syt2, Grik1, Prkar2b, Rcvrrn, Irx6, Gad1, Rho, Pdc, Nr1, Pde6a, Pde6h, Arr3, Opn1mw, and Opn1sw.

5. The method of claim 1, wherein validating gene expression against cellular morphology comprises sparsely labeling the cell to enhance the expression of a fluorescent protein in the cell and combining the sparse labeling with fluorescent in situ hybridization (FISH) to validate the marker against cellular morphology in step e).

6. The method of claim 5, wherein FISH is combined with a specific antibody, double FISH, or a transgenic reporter mouse line directed to a previously identified marker in the cell.

7. The method of claim 1, wherein the unsupervised machine-learning model is a k-means model, a mixture model, a hierarchical clustering model, an anomaly detection model, a neural network model, an expectation-maximization (EM) model, a method of moments model, or a blind signal separation technique.

8. A method of determining transcription signatures for cell types or cell sub-types, comprising:
 isolating a population of cells by label-free imaging flow cytometry;
 identifying cell types and/or cell sub-types by applying one or more clustering algorithms to a set of sequenced transcript reads from the population of cells,
  wherein the sequenced transcript reads are obtained from RNA sequencing of 20,000 or more single cells from a biological sample, wherein the sequencing depth is about 10,000 or less reads per cell,
  wherein each resulting cluster of sequenced transcript reads identifies a particular cell type or cell sub-type; and
 determining a transcription signature for each identified cell type or cell sub-type based at least in part on identifying differentially expressed transcripts between the identified cell type or cell sub-type by applying an unsupervised machine-learning model.

9. The method of claim 8, wherein the unsupervised machine learning model is a k-means model, a mixture model, a hierarchical clustering model, an anomaly detection model, a neural network model, an expectation-maximization (EM) model, a method of moments model, or a blind signal separation technique.

10. The method of claim 8, wherein the cell type and/or sub-types are retinal cell types and/or sub-types.

11. The method of claim 10, wherein the transcription signature identifies a rod bipolar cell, or one of the following cone bipolar cells; BC1A, BC1B, BC2, BC3A, BC3B, BC4, BC5A, BC5B, BC5C, BC5D, (XBC), BC6, BC7, BC8, and BC9.

12. The method of claim 11, wherein the transcription signature identifies a bipolar cell and comprises at least one of Pcdh17, Pcdh10, Erbb4, Nnat, Col11a1, Sox6, Chrm2, Slitrk5, Lrrtm1, Cck, Lect1, Igfn1, Serpini1, Cpne9, Vstm2b, Casp7, Vsx1, Vsx2, Otx2, Scgn, Slc1a2, Slc6a9, Pax6, Tfap2a, Stx1b, Tacr3, Bhlhe23, Fat4, Fezf1, Fezf2, Wfdc2, My1k, Hs3st2, W1 s, Nxph1, Lhx3, Cabp5, Grm6, Kcng4, Cdh9, Htr3a, Hcn1, Hcn4, Nfia, Cntn5, BC046251, Gfra3, Areg, Kirrel3, Isl1, Spock3, Serpini1, Prkca, Car8, Sebox, Apoe, GluI, Aqp4, Cabp5, Syt2, Grik1, Prkar2b, Rcvrrn, Irx6, Gad1, Rho, Pdc, Nrl, Pde6a, Pde6h, Arr3, Opn1mw, and Opn1sw.

* * * * *